(12) United States Patent
Loverix et al.

(10) Patent No.: US 10,023,647 B2
(45) Date of Patent: Jul. 17, 2018

(54) POLYPEPTIDES CAPABLE OF CELLULAR INTERNALIZATION

(71) Applicant: COMPLIX NV, Diepenbeek (BE)

(72) Inventors: Stefan Loverix, Ternat (BE); Philippe Alard, Merelbeke (BE); Sabrina Deroo, Roussy-le-Village (FR); Klaartje Somers, Kortessem (BE); Ignace Lasters, Antwerp (BE); Johan Desmet, Kortrijk (BE)

(73) Assignee: COMPLIX NV, Diepenbeek (BE)

( * ) Notice: Subject to any disclaimer, the term of this patent is extended or adjusted under 35 U.S.C. 154(b) by 114 days.

(21) Appl. No.: 14/437,063

(22) PCT Filed: Oct. 22, 2013

(86) PCT No.: PCT/EP2013/072050
§ 371 (c)(1),
(2) Date: Apr. 20, 2015

(87) PCT Pub. No.: WO2014/064092
PCT Pub. Date: May 1, 2014

(65) Prior Publication Data
US 2015/0266968 A1     Sep. 24, 2015

Related U.S. Application Data

(60) Provisional application No. 61/716,783, filed on Oct. 22, 2012.

(30) Foreign Application Priority Data

Oct. 22, 2012  (EP) .................................... 12189485

(51) Int. Cl.
| | |
|---|---|
| C07K 1/00 | (2006.01) |
| C07K 16/30 | (2006.01) |
| C07K 16/18 | (2006.01) |
| C07K 14/47 | (2006.01) |
| C07K 16/24 | (2006.01) |
| A61K 38/17 | (2006.01) |
| A61K 38/00 | (2006.01) |

(52) U.S. Cl.
CPC .......... *C07K 16/30* (2013.01); *A61K 38/1761* (2013.01); *C07K 14/4747* (2013.01); *C07K 16/18* (2013.01); *C07K 16/244* (2013.01); *A61K 38/00* (2013.01); *C07K 2317/77* (2013.01); *C07K 2318/20* (2013.01); *C07K 2319/10* (2013.01); *C07K 2319/40* (2013.01); *C07K 2319/73* (2013.01)

(58) Field of Classification Search
None
See application file for complete search history.

(56) References Cited

U.S. PATENT DOCUMENTS

2014/0363434 A1*  12/2014  Lasters .................. C07K 16/10
                                                        424/134.1

FOREIGN PATENT DOCUMENTS

| EP | 2161278 A1 | 10/2010 |
|---|---|---|
| WO | 2006000034 A1 | 1/2006 |
| WO | 2007113687 A2 | 10/2007 |
| WO | 2010066740 A1 | 6/2010 |
| WO | 2010068684 A2 | 6/2010 |
| WO | 2010129023 A2 | 11/2010 |
| WO | 2011003935 A1 | 1/2011 |
| WO | 2011003936 A1 | 1/2011 |
| WO | 2012092970 A1 | 7/2012 |
| WO | 2012092971 A1 | 7/2012 |
| WO | 2012093013 A1 | 7/2012 |
| WO | 2012093172 A1 | 7/2012 |

OTHER PUBLICATIONS

PCT/EP2013/072050 International Search Report and Written Opinion dated Feb. 10, 2014, 12 pages.
PCT/EP2013/072050 International Preliminary Report on Patentability dated Oct. 8, 2014, 17 pages.

* cited by examiner

*Primary Examiner* — Shulamith H Shafer
(74) *Attorney, Agent, or Firm* — Lathrop Gage LLP; James H. Velema, Esq.

(57) ABSTRACT

Provided herein are polypeptides that are capable of crossing the cellular membrane and entering into the intracellular environment, which polypeptides are suitable for use in prophylactic, therapeutic or diagnostic applications as well as in screening and detection. Nucleic acids encoding such polypeptides; methods for preparing such polypeptides, host cells expressing or capable of expressing such polypeptides, compositions, and in particular pharmaceutical compositions, that comprise such polypeptides, in particular for prophylactic, therapeutic or diagnostic purposes are also provided.

11 Claims, 10 Drawing Sheets

Figures 1, 2:
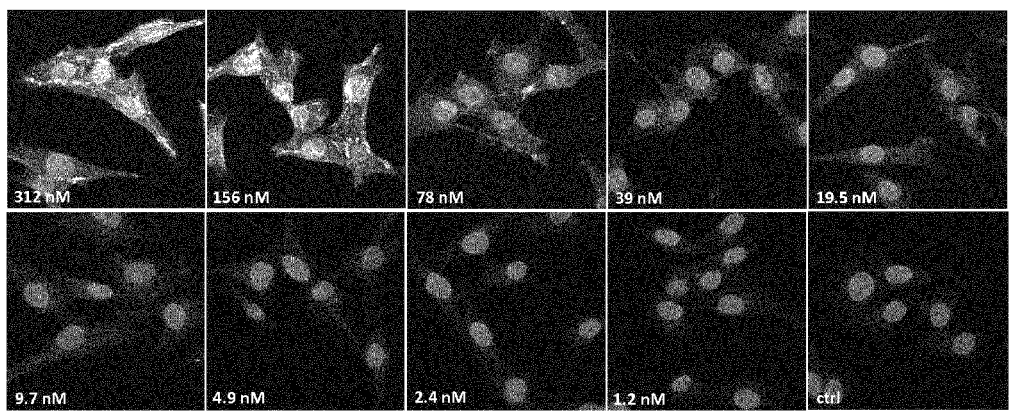

| MB23_hiR-V5 (SEQ ID NO : 2) |
|---|
| Helix A:   MSIEQIQKEITTIQEVIAAIQKYIYTMT |
| Loop 1:    GGSGGSGG |
| Helix B:   MSIQQIQAAIRRIQRAIRRIQRAIRRMT |
| Loop 2:    GSGGGGSG |
| Helix C:   MSIEEIQKQIAAIQEQIVAIYKQIMAMAS |
| His-tag:   HHHHHH |
| V5-tag:    <u>GKPIPNPLLGLDST</u> |

Figure 5

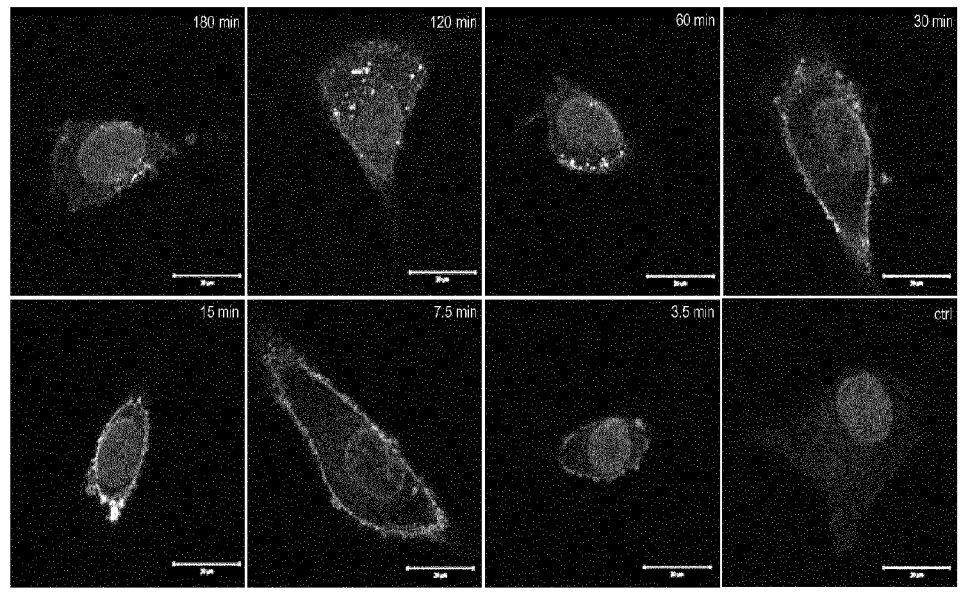

Figure 6

| AB1_hiKR1-V5 (SEQ ID NO: 4) (net charge: +11): | |
|---|---|
| A helix: | MSIQQIQKQIARIQKQIARIEKQIARMT |
| Loop 1: | GGSGGGSGGGSGGGSG |
| B helix: | MSIEEITKQIAAIQLRIVGDQVQIYAMT |
| Loop 2: | GGSGGGSGGGSGGGSG |
| C helix: | GSIEEIAKSIRAIQKEIAKIQKKIAKMTP |
| Tags: | HHHHHH-GKPIPNPLLGLDST |

| AB1_A2aF_hiKR3-V5 (SEQ ID NO: 6) (net charge: +19) | |
|---|---|
| A helix: | MSIQQIQKQFKRIQKQIKRIEKQIKRMT |
| Loop 1: | GGSGGSGG |
| B helix: | MSIEEITKQIAAIQLRIVGDQVQIYAMT |
| Loop 2: | GGSGGGSGGGSGGGSG |
| C helix: | GSIEEIKKSIRAIQKEIKKIQKKIKKMTP |
| Tags: | HHHHHHHHHH-GKPIPNPLLGLDST |

AB1_pan_hiKR3-V5 (SEQ ID NO : 10)

Helix A: MSIEEIQKQFKRIQKQIKRIAKQIKRMT

Loop 1: GGSGGSGG

Helix B: MSIEEIAAQIAAIQLRIIGD QFNIYYMT

Loop 2: GSGGGGSG

Helix C: GSIEEIKKSIRAIQKEIKKIQKKIKKMTP

His tag: -HHHHHHHHHH

V5 tag: -GKPIPNPLLGLDST

```
                              SEQUENCE LISTING

<160> NUMBER OF SEQ ID NOS: 33

<210> SEQ ID NO 1
<211> LENGTH: 101
<212> TYPE: PRT
<213> ORGANISM: Artificial
<220> FEATURE:
<223> OTHER INFORMATION: CPAB ALPHABODY SEQUENCE MB23

<400> SEQUENCE: 1

Met Ser Ile Glu Gln Ile Gln Lys Glu Ile Thr Thr Ile Gln Glu Val
1               5                   10                  15

Ile Ala Ala Ile Gln Lys Tyr Ile Tyr Thr Met Thr Gly Gly Ser Gly
            20                  25                  30

Gly Ser Gly Gly Met Ser Ile Gln Gln Ile Gln Ala Ala Ile Arg Arg
        35                  40                  45

Ile Gln Arg Ala Ile Arg Arg Ile Gln Arg Ala Ile Arg Arg Met Thr
    50                  55                  60

Gly Ser Gly Gly Gly Gly Ser Gly Met Ser Ile Glu Glu Ile Gln Lys
65                  70                  75                  80

Gln Ile Ala Ala Ile Gln Glu Gln Ile Val Ala Ile Tyr Lys Gln Ile
                85                  90                  95

Met Ala Met Ala Ser
            100

<210> SEQ ID NO 2
<211> LENGTH: 121
<212> TYPE: PRT
<213> ORGANISM: Artificial
<220> FEATURE:
<223> OTHER INFORMATION: CPAB ALPHABODY SEQUENCE MB23_hiR-V5
<220> FEATURE:
<221> NAME/KEY: MISC_FEATURE
<222> LOCATION: (102)..(107)
<223> OTHER INFORMATION: His tag
<220> FEATURE:
<221> NAME/KEY: MISC_FEATURE
<222> LOCATION: (108)..(121)
<223> OTHER INFORMATION: V5 tag

<400> SEQUENCE: 2

Met Ser Ile Glu Gln Ile Gln Lys Glu Ile Thr Thr Ile Gln Glu Val
1               5                   10                  15

Ile Ala Ala Ile Gln Lys Tyr Ile Tyr Thr Met Thr Gly Gly Ser Gly
            20                  25                  30

Gly Ser Gly Gly Met Ser Ile Gln Gln Ile Gln Ala Ala Ile Arg Arg
        35                  40                  45

Ile Gln Arg Ala Ile Arg Arg Ile Gln Arg Ala Ile Arg Arg Met Thr
    50                  55                  60

Gly Ser Gly Gly Gly Gly Ser Gly Met Ser Ile Glu Glu Ile Gln Lys
65                  70                  75                  80

Gln Ile Ala Ala Ile Gln Glu Gln Ile Val Ala Ile Tyr Lys Gln Ile
                85                  90                  95

Met Ala Met Ala Ser His His His His His His Gly Lys Pro Ile Pro
```

Asn Pro Leu Leu Gly Leu Asp Ser Thr
          115                 120

<210> SEQ ID NO 3
<211> LENGTH: 117
<212> TYPE: PRT
<213> ORGANISM: Artificial
<220> FEATURE:
<223> OTHER INFORMATION: CPAB ALPHABODY SEQUENCE AB1

<400> SEQUENCE: 3

Met Ser Ile Gln Gln Ile Gln Lys Gln Ile Ala Arg Ile Gln Lys Gln
1               5                   10                  15

Ile Ala Arg Ile Glu Lys Gln Ile Ala Arg Met Thr Gly Gly Ser Gly
            20                  25                  30

Gly Gly Ser Gly Gly Gly Ser Gly Gly Ser Gly Met Ser Ile Glu
        35                  40                  45

Glu Ile Thr Lys Gln Ile Ala Ala Ile Gln Leu Arg Ile Val Gly Asp
    50                  55                  60

Gln Val Gln Ile Tyr Ala Met Thr Gly Gly Ser Gly Gly Gly Ser Gly
65              70                  75                  80

Gly Gly Ser Gly Gly Gly Ser Gly Gly Ser Ile Glu Glu Ile Ala Lys
            85                  90                  95

Ser Ile Arg Ala Ile Gln Lys Glu Ile Ala Lys Ile Gln Lys Lys Ile
            100                 105                 110

Ala Lys Met Thr Pro
        115

<210> SEQ ID NO 4
<211> LENGTH: 137
<212> TYPE: PRT
<213> ORGANISM: Artificial
<220> FEATURE:
<223> OTHER INFORMATION: CPAB ALPHABODY SEQUENCE AB1_hiKR1-V5
<220> FEATURE:
<221> NAME/KEY: MISC_FEATURE
<222> LOCATION: (118)..(123)
<223> OTHER INFORMATION: His tag
<220> FEATURE:
<221> NAME/KEY: MISC_FEATURE
<222> LOCATION: (124)..(137)
<223> OTHER INFORMATION: V5 tag

<400> SEQUENCE: 4

Met Ser Ile Gln Gln Ile Gln Lys Gln Ile Ala Arg Ile Gln Lys Gln
1               5                   10                  15

Ile Ala Arg Ile Glu Lys Gln Ile Ala Arg Met Thr Gly Gly Ser Gly
            20                  25                  30

Gly Gly Ser Gly Gly Gly Ser Gly Gly Ser Gly Met Ser Ile Glu
        35                  40                  45

Glu Ile Thr Lys Gln Ile Ala Ala Ile Gln Leu Arg Ile Val Gly Asp
    50                  55                  60

Gln Val Gln Ile Tyr Ala Met Thr Gly Gly Ser Gly Gly Gly Ser Gly
65              70                  75                  80

Gly Gly Ser Gly Gly Gly Ser Gly Gly Ser Ile Glu Glu Ile Ala Lys
            85                  90                  95

Ser Ile Arg Ala Ile Gln Lys Glu Ile Ala Lys Ile Gln Lys Lys Ile
            100                 105                 110

Ala Lys Met Thr Pro His His His His His His Gly Lys Pro Ile Pro

```
                115                 120                 125
Asn Pro Leu Leu Gly Leu Asp Ser Thr
    130                 135

<210> SEQ ID NO 5
<211> LENGTH: 109
<212> TYPE: PRT
<213> ORGANISM: Artificial
<220> FEATURE:
<223> OTHER INFORMATION: CPAB ALPHABODY SEQUENCE AB1_A2aF

<400> SEQUENCE: 5

Met Ser Ile Gln Gln Ile Gln Lys Gln Phe Lys Arg Ile Gln Lys Gln
1               5                   10                  15

Ile Lys Arg Ile Glu Lys Gln Ile Lys Arg Met Thr Gly Gly Ser Gly
            20                  25                  30

Gly Ser Gly Gly Met Ser Ile Glu Glu Ile Thr Lys Gln Ile Ala Ala
        35                  40                  45

Ile Gln Leu Arg Ile Val Gly Asp Gln Val Gln Ile Tyr Ala Met Thr
    50                  55                  60

Gly Gly Ser Gly Gly Gly Ser Gly Gly Ser Gly Gly Gly Ser Gly
65                  70                  75                  80

Gly Ser Ile Glu Glu Ile Lys Lys Ser Ile Arg Ala Ile Gln Lys Glu
            85                  90                  95

Ile Lys Lys Ile Gln Lys Lys Ile Lys Lys Met Thr Pro
            100                 105

<210> SEQ ID NO 6
<211> LENGTH: 133
<212> TYPE: PRT
<213> ORGANISM: Artificial
<220> FEATURE:
<223> OTHER INFORMATION: CPAB ALPHABODY SEQUENCE AB1_A2aF_hiKR3-V5
<220> FEATURE:
<221> NAME/KEY: MISC_FEATURE
<222> LOCATION: (110)..(119)
<223> OTHER INFORMATION: His tag
<220> FEATURE:
<221> NAME/KEY: MISC_FEATURE
<222> LOCATION: (120)..(133)
<223> OTHER INFORMATION: V tag

<400> SEQUENCE: 6

Met Ser Ile Gln Gln Ile Gln Lys Gln Phe Lys Arg Ile Gln Lys Gln
1               5                   10                  15

Ile Lys Arg Ile Glu Lys Gln Ile Lys Arg Met Thr Gly Gly Ser Gly
            20                  25                  30

Gly Ser Gly Gly Met Ser Ile Glu Glu Ile Thr Lys Gln Ile Ala Ala
        35                  40                  45

Ile Gln Leu Arg Ile Val Gly Asp Gln Val Gln Ile Tyr Ala Met Thr
    50                  55                  60

Gly Gly Ser Gly Gly Gly Ser Gly Gly Ser Gly Gly Gly Ser Gly
65                  70                  75                  80

Gly Ser Ile Glu Glu Ile Lys Lys Ser Ile Arg Ala Ile Gln Lys Glu
            85                  90                  95

Ile Lys Lys Ile Gln Lys Lys Ile Lys Lys Met Thr Pro His His His
            100                 105                 110

His His His His His Gly Lys Pro Ile Pro Asn Pro Leu Leu
    115                 120                 125

Gly Leu Asp Ser Thr
```

<210> SEQ ID NO 7
<211> LENGTH: 28
<212> TYPE: PRT
<213> ORGANISM: Artificial
<220> FEATURE:
<223> OTHER INFORMATION: Sequence of B-helix of Alphabody AB1(_hiKR1-V5)
      and AB1_A2aF(_hiKR3-V5)

<400> SEQUENCE: 7

Met Ser Ile Glu Glu Ile Thr Lys Gln Ile Ala Ala Ile Gln Leu Arg
1               5                   10                  15

Ile Val Gly Asp Gln Val Gln Ile Tyr Ala Met Thr
            20                  25

<210> SEQ ID NO 8
<211> LENGTH: 8
<212> TYPE: PRT
<213> ORGANISM: Artificial
<220> FEATURE:
<223> OTHER INFORMATION: Binding site for MCL-1 in B-helix of Alphabody
      AB1(_hiKR1-V5) and AB1_A2aF(_hiKR3-V5)
<220> FEATURE:
<221> NAME/KEY: MISC_FEATURE
<222> LOCATION: (3)..(3)
<223> OTHER INFORMATION: X is any amino acid residue
<220> FEATURE:
<221> NAME/KEY: MISC_FEATURE
<222> LOCATION: (7)..(7)
<223> OTHER INFORMATION: X is any amino acid residue

<400> SEQUENCE: 8

Leu Arg Xaa Val Gly Asp Xaa Val
1               5

<210> SEQ ID NO 9
<211> LENGTH: 101
<212> TYPE: PRT
<213> ORGANISM: Artificial
<220> FEATURE:
<223> OTHER INFORMATION: CPAB ALPHABODY SEQUENCE AB1_pan

<400> SEQUENCE: 9

Met Ser Ile Glu Glu Ile Gln Lys Gln Phe Lys Arg Ile Gln Lys Gln
1               5                   10                  15

Ile Lys Arg Ile Ala Lys Gln Ile Lys Arg Met Thr Gly Gly Ser Gly
            20                  25                  30

Gly Ser Gly Gly Met Ser Ile Glu Glu Ile Ala Ala Gln Ile Ala Ala
        35                  40                  45

Ile Gln Leu Arg Ile Ile Gly Asp Gln Phe Asn Ile Tyr Tyr Met Thr
    50                  55                  60

Gly Ser Gly Gly Gly Ser Gly Gly Ser Ile Glu Glu Ile Lys Lys
65                  70                  75                  80

Ser Ile Arg Ala Ile Gln Lys Glu Ile Lys Ile Gln Lys Lys Ile
                85                  90                  95

Lys Lys Met Thr Pro
            100

<210> SEQ ID NO 10
<211> LENGTH: 125
<212> TYPE: PRT
<213> ORGANISM: Artificial
<220> FEATURE:
<223> OTHER INFORMATION: CPAB ALPHABODY SEQUENCE AB1_pan_hiKR3-V5

```
<220> FEATURE:
<221> NAME/KEY: MISC_FEATURE
<222> LOCATION: (102)..(111)
<223> OTHER INFORMATION: His tag
<220> FEATURE:
<221> NAME/KEY: MISC_FEATURE
<222> LOCATION: (112)..(125)
<223> OTHER INFORMATION: V5 tag

<400> SEQUENCE: 10

Met Ser Ile Glu Glu Ile Gln Lys Gln Phe Lys Arg Ile Gln Lys Gln
1               5                   10                  15

Ile Lys Arg Ile Ala Lys Gln Ile Lys Arg Met Thr Gly Gly Ser Gly
            20                  25                  30

Gly Ser Gly Gly Met Ser Ile Glu Glu Ile Ala Ala Gln Ile Ala Ala
        35                  40                  45

Ile Gln Leu Arg Ile Ile Gly Asp Gln Phe Asn Ile Tyr Tyr Met Thr
    50                  55                  60

Gly Ser Gly Gly Gly Ser Gly Gly Ser Ile Glu Glu Ile Lys Lys
65                  70                  75                  80

Ser Ile Arg Ala Ile Gln Lys Glu Ile Lys Lys Ile Gln Lys Lys Ile
                85                  90                  95

Lys Lys Met Thr Pro His His His His His His His His His Gly
            100                 105                 110

Lys Pro Ile Pro Asn Pro Leu Leu Gly Leu Asp Ser Thr
            115                 120                 125

<210> SEQ ID NO 11
<211> LENGTH: 28
<212> TYPE: PRT
<213> ORGANISM: Artificial
<220> FEATURE:
<223> OTHER INFORMATION: Sequence of B-helix of Alphabody
      AB1_pan_hiKR3-V5

<400> SEQUENCE: 11

Met Ser Ile Glu Glu Ile Ala Ala Gln Ile Ala Ala Ile Gln Leu Arg
1               5                   10                  15

Ile Ile Gly Asp Gln Phe Asn Ile Tyr Tyr Met Thr
            20                  25

<210> SEQ ID NO 12
<211> LENGTH: 8
<212> TYPE: PRT
<213> ORGANISM: Artificial
<220> FEATURE:
<223> OTHER INFORMATION: Binding site for BCL-2a or BCL-XL in B-helix of
      Alphabody AB1_pan_hiKR3-V5

<400> SEQUENCE: 12

Leu Arg Ile Ile Gly Asp Gln Phe
1               5

<210> SEQ ID NO 13
<211> LENGTH: 22
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(22)
<223> OTHER INFORMATION: Xaa=any polar amino acid

<400> SEQUENCE: 13
```

```
Ile Arg Ile Xaa Arg Xaa Ile Arg Arg Ile Xaa Arg Xaa Ile Xaa Ile
1               5                   10                  15

Xaa Xaa Xaa Ile Xaa Xaa
            20
```

<210> SEQ ID NO 14
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 14

```
Ile Xaa Arg Ile Xaa Arg Xaa Ile Arg Arg Ile Xaa Arg Xaa Ile Arg
1               5                   10                  15

Xaa Ile Xaa Xaa Xaa Ile Xaa Xaa
            20
```

<210> SEQ ID NO 15
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 15

```
Ile Xaa Xaa Ile Xaa Arg Xaa Ile Arg Arg Ile Xaa Arg Xaa Ile Arg
1               5                   10                  15

Arg Ile Xaa Xaa Xaa Ile Xaa Xaa
            20
```

<210> SEQ ID NO 16
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 16

```
Ile Arg Xaa Ile Arg Xaa Xaa Ile Arg Xaa Ile Xaa Arg Xaa Ile Arg
1               5                   10                  15

Arg Ile Xaa Xaa Xaa Ile Xaa Xaa
            20
```

<210> SEQ ID NO 17
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

```
<400> SEQUENCE: 17

Ile Xaa Xaa Ile Arg Xaa Xaa Ile Arg Xaa Ile Xaa Arg Xaa Ile Arg
1               5                   10                  15

Arg Ile Xaa Arg Xaa Ile Xaa Xaa
            20

<210> SEQ ID NO 18
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 18

Ile Arg Xaa Ile Arg Xaa Xaa Ile Arg Xaa Ile Xaa Arg Xaa Ile Arg
1               5                   10                  15

Arg Ile Xaa Arg Xaa Ile Xaa Xaa
            20

<210> SEQ ID NO 19
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 19

Ile Arg Xaa Ile Arg Arg Xaa Ile Arg Xaa Ile Arg Xaa Xaa Ile Arg
1               5                   10                  15

Arg Ile Arg Arg Xaa Ile Xaa Xaa
            20

<210> SEQ ID NO 20
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 20

Ile Arg Xaa Ile Arg Arg Xaa Ile Arg Xaa Ile Arg Arg Xaa Ile Xaa
1               5                   10                  15

Xaa Ile Xaa Xaa Xaa Ile Xaa Xaa
            20

<210> SEQ ID NO 21
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid
```

<400> SEQUENCE: 21

Ile Xaa Xaa Ile Arg Arg Xaa Ile Arg Xaa Ile Arg Arg Xaa Ile Arg
1               5                   10                  15

Xaa Ile Xaa Xaa Xaa Ile Xaa Xaa
            20

<210> SEQ ID NO 22
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 22

Ile Xaa Xaa Ile Xaa Xaa Xaa Ile Arg Xaa Ile Arg Arg Xaa Ile Arg
1               5                   10                  15

Xaa Ile Arg Arg Xaa Ile Xaa Xaa
            20

<210> SEQ ID NO 23
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 23

Ile Xaa Xaa Ile Arg Arg Xaa Ile Arg Xaa Ile Xaa Arg Xaa Ile Arg
1               5                   10                  15

Arg Ile Xaa Arg Arg Ile Arg Arg
            20

<210> SEQ ID NO 24
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 24

Ile Xaa Xaa Ile Arg Arg Xaa Ile Arg Xaa Ile Xaa Arg Xaa Ile Arg
1               5                   10                  15

Arg Ile Xaa Xaa Xaa Ile Xaa Xaa
            20

<210> SEQ ID NO 25
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)

<223> OTHER INFORMATION: Xaa=any polar amino acid

<400> SEQUENCE: 25

Ile Xaa Xaa Ile Xaa Arg Xaa Ile Arg Xaa Ile Xaa Arg Xaa Ile Arg
1               5                   10                  15

Arg Ile Xaa Arg Xaa Ile Xaa Xaa
            20

<210> SEQ ID NO 26
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 26

Ile Xaa Xaa Ile Xaa Xaa Xaa Ile Arg Xaa Ile Xaa Arg Xaa Ile Arg
1               5                   10                  15

Arg Ile Xaa Arg Arg Ile Xaa Xaa
            20

<210> SEQ ID NO 27
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 27

Ile Xaa Xaa Ile Xaa Xaa Xaa Ile Xaa Xaa Ile Xaa Arg Xaa Ile Arg
1               5                   10                  15

Arg Ile Xaa Arg Arg Ile Arg Xaa
            20

<210> SEQ ID NO 28
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 28

Ile Xaa Xaa Ile Xaa Xaa Xaa Ile Xaa Xaa Ile Xaa Xaa Xaa Ile Arg
1               5                   10                  15

Arg Ile Xaa Arg Arg Ile Arg Arg
            20

<210> SEQ ID NO 29
<211> LENGTH: 16
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE

```
<222> LOCATION: (1)..(16)
<223> OTHER INFORMATION: Xaa=any polar amino acid

<400> SEQUENCE: 29

Arg Arg Ile Xaa Xaa Xaa Ile Arg Arg Ile Xaa Xaa Xaa Ile Arg Arg
1               5                   10                  15

<210> SEQ ID NO 30
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 30

Ile Xaa Xaa Ile Xaa Xaa Xaa Ile Arg Arg Ile Xaa Arg Xaa Ile Arg
1               5                   10                  15

Arg Ile Xaa Arg Xaa Ile Xaa Xaa
            20

<210> SEQ ID NO 31
<211> LENGTH: 24
<212> TYPE: PRT
<213> ORGANISM: Artificial Sequence
<220> FEATURE:
<223> OTHER INFORMATION: exemplary motif sequence
<220> FEATURE:
<221> NAME/KEY: MISC_FEATURE
<222> LOCATION: (1)..(24)
<223> OTHER INFORMATION: Xaa=any polar amino acid

<400> SEQUENCE: 31

Ile Xaa Xaa Ile Xaa Xaa Xaa Ile Arg Arg Ile Xaa Arg Xaa Ile Arg
1               5                   10                  15

Arg Ile Xaa Arg Xaa Ile Arg Xaa
            20

<210> SEQ ID NO 32
<211> LENGTH: 24
<212> TYPE: PRT
<213> ORGANISM: Artificial Sequence
<220> FEATURE:
<223> OTHER INFORMATION: examplary motif sequence
<220> FEATURE:
<221> NAME/KEY: MISC_FEATURE
<222> LOCATION: (1)..(24)

<400> SEQUENCE: 32

Ile Xaa Xaa Ile Xaa Xaa Xaa Ile Arg Arg Ile Xaa Arg Xaa Ile Arg
1               5                   10                  15

Arg Ile Xaa Arg Xaa Ile Arg Arg
            20

<210> SEQ ID NO 33
<211> LENGTH: 122
<212> TYPE: PRT
<213> ORGANISM: Artificial Sequence
<220> FEATURE:
<223> OTHER INFORMATION: MB23 hiR_no tag

<400> SEQUENCE: 33

Met Gly His His His His His His His His His Ser Ser Gly His
1               5                   10                  15
```

```
Ile Glu Gly Arg His Met Ser Ile Glu Gln Ile Gln Lys Glu Ile Thr
                20              25              30

Thr Ile Gln Glu Val Ile Ala Ala Ile Gln Lys Tyr Ile Tyr Thr Met
            35              40              45

Thr Gly Gly Ser Gly Gly Ser Gly Gly Met Ser Ile Gln Gln Ile Gln
        50              55              60

Ala Ala Ile Arg Arg Ile Gln Arg Ala Ile Arg Arg Ile Gln Arg Ala
65              70              75              80

Ile Arg Arg Met Thr Gly Ser Gly Gly Gly Gly Ser Gly Met Ser Ile
                85              90              95

Glu Glu Ile Gln Lys Gln Ile Ala Ala Ile Gln Glu Gln Ile Val Ala
            100             105             110

Ile Tyr Lys Gln Ile Met Ala Met Ala Ser
        115             120
```

POLYPEPTIDES CAPABLE OF CELLULAR INTERNALIZATION

RELATED APPLICATIONS

This application is a 371 filing of Patent Cooperation Treaty Application No. PCT/EP2013/072050, filed Oct. 22, 2013, which claims priority to European Patent Application No. 12189485.1, filed Oct. 22, 2012 and U.S. Patent Application No. 61/716,783, filed Oct. 22, 2012, the contents of each of which are incorporated herein by reference in their entirety.

FIELD OF THE INVENTION

The application relates to molecules that are capable of crossing the cellular membrane and entering into the intracellular environment, which molecules are suitable for use in prophylactic, therapeutic or diagnostic applications as well as in screening and detection.

BACKGROUND

Interaction with intracellular components of a cell requires that the cellular membrane is crossed by an agent that is expected to interact with such intracellular components. However, such agents often lack the necessary balance of biological and physicochemical properties such as hydrophobicity, solubility, charge and size to cross the cell membrane.

In the therapeutic field, macromolecules (such as polypeptides and nucleic acids) have been the main focus because for many diseases, small molecule drugs (i.e. chemical compounds containing less than 100 atoms) are very difficult to find and/or develop. The use of macromolecules as therapeutic agents has a number of advantages over small molecules, the most important one being the ability to adopt large, stable three-dimensional conformations suitable for strong binding to targets, thereby allowing to interfere with native protein-protein or protein-nucleic acid interfaces that are difficult to address using small molecules. Moreover, the stability, size, and complexity of macromolecules can result in specificities that are not easily achievable using small molecules.

However, a great difficulty is that macromolecules as such are not able to diffuse into cells, and thus, while the great majority of disease targets of interest are located inside cells, most macromolecule therapeutics are only capable of addressing extracellular targets. Accordingly, over the years, various approaches for intracellular delivery of macromolecules have been developed, including electroporation, ultrasound-mediated plasmid delivery, viral delivery, nebulization, and direct chemical modification. Other strategies associate a macromolecule with a non-viral delivery vehicle such as lipidoids, liposomes, dendrimers, cationic polymers, inorganic nanoparticles, carbon nanotubes, cell-penetrating peptides, small molecules, or receptor ligands. The use of supercharged proteins as vectors or carriers for macromolecule delivery into mammalian cells has been reported (Lawrence, M. S. et al. 2007, *J. Am. Chem. Soc.* 129, (33), 10110-10112; Cronican et al. 2010 ACS CHEMICAL BIOLOGY; McNaughton et al. 2009 PNAS).

Although these strategies may facilitate internalization, their applicability is restricted. For example, these methods utilize cellular mechanisms of internalization leading to accumulation of an effector in the lysosomes and ultimately resulting in degradation and inactivation of the effector compound.

SUMMARY OF THE INVENTION

Provided herein are alternative and improved polypeptides, which are able to penetrate cell membranes, and are extremely stable in the intracellular environment. This allows their use as intracellular agents, which are capable of ensuring that an effector function targeting an intracellular target is introduced into the cell.

In particular embodiments, the effector function is incorporated in the polypeptides themselves, i.e. in these cases, the polypeptides are not only capable of entering cells but are also able to specifically bind to an intracellular target molecule in the cell, thereby efficiently inhibiting or at least modulating the biological mechanisms and or signaling pathways in which that intracellular target molecule plays a role.

The polypeptides comprising at least one Alphabody structure sequence as provided herein, are capable of being internalized into a cell through the presence of at least one positively charged internalization region, which is comprised at least in part within said Alphabody structure sequence. A positively charged internalization region as used herein typically extends between two positively charged amino acid residues of the polypeptides envisaged herein and is at least partially comprised within the Alphabody structure sequence comprised in these polypeptides.

In particular embodiments, the polypeptides provided herein comprising at least one Alphabody structure sequence and at least one positively charged internalization region ensuring internalization of said polypeptide into a cell, wherein said internalization region extends between two positively charged amino acid residues, consists of a fragment of not more than 16 amino acid residues and is characterized by the presence of at least six positively charged amino acid residues of which at least 50% are comprised within said Alphabody structure sequence. Thus, the polypeptides provided herein comprise a positively charged sequence that starts and ends with a positively charged amino acid residue and which ensures that the polypeptides are capable of entering the cell. In particular, the polypeptides envisaged herein comprise a positively charged sequence which ensures that the polypeptides are able to cross the cellular membrane or which enhances, stimulates or triggers cellular transport. The polypeptides provided herein have been specifically designed so as to obtain a modified structure compared to known polypeptides comprising Alphabody sequences, thereby allowing internalization of the polypeptides into the cell.

In particular embodiments, the at least one positively charged internalization region at least partially located within the Alphabody structure sequence present in the polypeptides as envisaged herein, is characterized by the presence of at least six positively charged amino acid residues, such as at least six amino acid residues chosen from the group consisting of arginine and lysine. In further particular embodiments, the at least one positively charged internalization region in the polypeptides as envisaged herein is characterized by the presence of at least six positively charged amino acid residues, of which at least four residues are arginines. In further particular embodiments, the at least one positively charged internalization region in the polypeptides as envisaged herein is characterized by the presence of at least six positively charged amino acid residues, of which at least five residues are lysines.

In particular embodiments of the polypeptides envisaged herein said positively charged internalization region comprises between 6 and 12 Arginine residues.

In particular embodiments, the polypeptides envisaged herein comprise in their Alphabody sequence a motif selected from the group consisting of: ZZXXZXXZZXXZ, ZXXZXXZZXXZXXZ, ZXXZZXXZXXZZ, ZXXZXXXZXXXZXXZZ, ZXXXZXXXZXXZZXXZ, ZXXZZXXZXXZZ, ZZXXZXXXZXXZZ, ZXXZXXXZXXZZXXZ, ZXXXZXXZZXXZZ, ZXXZZXXZZXZ, ZZXXZZXZZ, ZZXXXXXZZXXXXXZZ, wherein Z represents a positively charged amino acid and X represents any amino acid residue. In particular embodiments, between 75 and 100% of said Z in said motif are Arginine. In further particular embodiments, the polypeptides comprise within a sequence corresponding to an Alphabody structure, a sequence selected from SEQ ID No. 13 to 32.

In particular embodiments, the polypeptides provided herein comprise at least one Alphabody structure sequence, which
(i) is capable of being internalized into a cell through the presence of at least one positively charged internalization region as described herein, which is comprised at least in part within said Alphabody structure sequence, and in addition
(ii) specifically binds to an intracellular target molecule primarily through a binding site present on the Alphabody structure sequence.

In these particular embodiments, the polypeptides provided herein specifically bind to an intracellular target molecule primarily through a binding site present on the B-helix of the Alphabody structure sequence.

In certain particular embodiments, polypeptides comprising an Alphabody structure are provided which are capable of binding to an intracellular target and are characterized by the presence of one or more positively charged internalization regions at least partially located within the Alphabody structure sequence present in said polypeptide, wherein the internalization region consists of a stretch of not more than 16 amino acid residues, which is characterized by the presence of at least six positively charged amino acid residues.

In further particular embodiments of the polypeptides provided herein, at least 80% of the amino acid residues comprised in at least one positively charged internalization region are fully comprised within one Alphabody structure sequence; and in still further particular embodiments, the at least one internalization region is entirely comprised within said at least one Alphabody structure sequence, such as (entirely or fully) comprised within one alpha-helix of said at least one Alphabody structure sequence. In further particular embodiments, the at least one internalization region is (entirely or fully) comprised within the A-helix and/or within the C-helix of said at least one Alphabody structure sequence.

In further particular embodiments, the polypeptides provided herein are characterized in that they comprise a sequence selected from SEQ ID NO: 1 to 6, 9 and 10. In further particular embodiments, the internalization region consists for at least 30% of amino acid residues which, when mutated into glutamine or glutamic acid, each reduce cellular uptake of said polypeptide by at least 50%.

Since, the polypeptides as envisaged herein have the potential to either directly or indirectly affect the biological function of intracellular targets inside cells they are particularly useful for medical, i.e. therapeutic or prophylactic, applications in a wide variety of disease indications.

Moreover, the polypeptides according to particular embodiments as envisaged herein which also contain a binding site for an intracellular target with the Alphabody structure have the potential to address a class of proteins which is currently considered "undruggable" by the two main categories of therapeutic drugs, i.e. (i) small chemical drugs and (ii) therapeutic antibodies or proteins. Indeed, a large proportion of all known human protein targets cannot be addressed by either small chemical drugs or biologics. Small chemicals typically interact with hydrophobic pockets, which limits their target space to about 10% of all human proteins; similarly, biologics (i.e. protein-based therapeutics like antibodies) lack the ability to penetrate through cell membranes, and therefore can only address another 10% (those that exist as extracellular proteins). This means that the vast majority of all potential (mainly intracellular) protein targets, (estimated at >80%), across all therapeutic areas, are currently considered "undruggable" by the two main known classes of therapeutic drugs.

A large number of intracellular proteins belong to the most interesting class of potential drug targets, namely intracellular protein-protein interactions. Intracellular protein-protein interactions regulate a wide variety of essential cellular processes, many of which are known to be involved in important disease processes, such as those causing cancer, central nervous system diseases or metabolic diseases. The polypeptides disclosed herein are shown to possess the capability for intracellular penetration and to remain stable within the cell and to bind their target in the cell. Therefore, they represent a unique tool for modulating intracellular protein-protein interactions and as therapeutics that can address the vast number of currently "undruggable" targets that are involved in a broad range of diseases.

Thus, also provided herein is the use of the polypeptides described herein as a medicament, and more particularly in methods for the treatment of diseases or disorders which are associated with the biological pathways or biological interactions in which an intracellular target molecule is involved.

Accordingly, in particular embodiments, therapeutic methods are provided herein which make use of polypeptides as envisaged herein comprising at least one Alphabody, which is capable of being internalized by a cell, wherein the at least one Alphabody specifically binds to an intracellular target, such as for example, but not limited to, a protein involved in a cellular process chosen from the group consisting of cell signaling, cell signal transduction, cellular and molecular transport (e.g. active transport or passive transport), osmosis, phagocytosis, autophagy, cell senescence, cell adhesion, cell motility, cell migration, cytoplasmic streaming, DNA replication, protein synthesis, reproduction (e.g. cell cycle, meiosis, mitosis, interphase, cytokinesis), cellular metabolism (e.g. glycolysis and respiration, energy supply), cell communication, DNA repair, apoptotis and programmed cell death.

In particular embodiments, polypeptides are provided comprising at least one Alphabody, which are capable of being internalized by a cell, wherein the at least one Alphabody specifically binds to an intracellular protein involved in cellular apoptosis, such as for example an apoptotic or an anti-apoptotic intracellular protein, in particular an anti-apoptotic member of the BCL-2 family of proteins, such as for example those selected from the group consisting of MCL-1, BCL-2, BCL-XL, BCL-w and BFL-1/A1.

Accordingly, in particular embodiments, polypeptides are provided which are capable of being internalized by a cell and capable of binding to MCL-1.

In further particular embodiments, the polypeptides are characterized in that they comprise a sequence selected from SEQ ID NO: 3 to 6, 9 and 10. In particular embodiments, polypeptides are provided which are capable of being internalized by a cell and capable of binding to MCL-1, whereby the polypeptides are characterized in that they comprise a sequence having at least 60%, at least 70%, at least 80%, at least 90%, at least 95% or more sequence identity with a polypeptide sequence as defined in SEQ ID NO: 7 (MSIEE-ITKQIAAIQLRIVGDQVQIYAMT).

In particular embodiments, polypeptides are provided which are capable of being internalized by a cell and capable of binding to MCL-1, whereby the polypeptides are characterized in that they comprise a sequence as defined in SEQ ID NO: 8 (LRXVGDXV).

In particular embodiments, polypeptides are provided which are capable of being internalized by a cell and capable of binding to BCL-2a, whereby the polypeptides are characterized in that they comprise a sequence selected from SEQ ID NO: 9 and 10.

In particular embodiments, polypeptides are provided which are capable of being internalized by a cell and capable of binding to BCL-XL, whereby the polypeptides are characterized in that they comprise a sequence selected from SEQ ID NO: 9 and 10.

In particular embodiments, polypeptides are provided which are capable of being internalized by a cell and capable of binding to BCL-2a and/or BCL-XL, whereby the polypeptides are characterized in that they comprise a sequence having at least 60%, at least 70%, at least 80%, at least 90%, at least 95% or more sequence identity with a polypeptide sequence as defined in SEQ ID NO: 11 (MSIEEIAAQIAAI-QLRIIGDQFNIYYMT).

In particular embodiments, polypeptides are provided which are capable of being internalized by a cell and capable of binding to BCL-2a and/or BCL-XL whereby the polypeptides are characterized in that they comprise a sequence as defined in SEQ ID NO: 12 (LRIIGDQF).

In accordance with the above the application also discloses pharmaceutical compositions comprising at least one polypeptide as described herein, and optionally one or more pharmaceutically acceptable carriers.

In a further aspect, other applications of the polypeptides as provided herein are also envisaged.

In particular embodiments, the polypeptides as provided herein can be used for modulating the biological function of an intracellular protein in vitro, such as for instance for affecting and, in particular inhibiting, the interaction between the intracellular protein and natural binding partner.

Additionally, in a further aspect, methods are provided herein for the production of the polypeptides as described herein which are capable of being internalized into a cell, which methods at least comprise the step of manufacturing or modifying a polypeptide comprising an Alphabody structure sequence so as to obtain an internalization region comprised at least in part within said Alphabody structure sequence.

In particular embodiments, the methods as envisaged herein at least comprise the step of introducing an internalization region into at least part of a sequence of at least one Alphabody structure.

In particular embodiments, the methods envisaged herein may further comprise, prior to the step of introducing the internalization region, the step of selecting at least one Alphabody structure for its specific binding affinity to an intracellular target molecule of interest. In alternative particular embodiments, the methods as envisaged herein may further comprise, subsequent to the step of introducing said internalization region, the step of selecting at least one Alphabody structure for its specific binding affinity to an intracellular target molecule of interest. In yet further embodiments, these methods may include the step of linking said Alphabody structure to a therapeutic or diagnostic molecule of interest.

In particular embodiments of the methods envisaged herein, the step of introducing an internalization region into a sequence of at least one Alphabody structure comprises the introduction of specific mutations into a chosen Alphabody structure sequence template. Alternatively, in particular embodiments of the methods envisaged herein, the step of introducing an internalization region into a sequence of at least one Alphabody structure comprises the in silico design of an Alphabody structure sequence comprising one or more internalization regions.

When selecting, in particular embodiments of the methods envisaged herein, at least one Alphabody structure (or polypeptide) for its specific binding affinity to an intracellular target molecule of interest, this may involve at least the step of screening a library of Alphabody structure sequences (or polypeptide sequences) for specific binding to said intracellular target molecule or, alternatively at least the step of introducing a binding motif in said at least one Alphabody structure sequence to said intracellular target molecule and testing the specific binding affinity to said intracellular target molecule of interest.

As will become clear from the further detailed description and examples disclosed herein, it has been demonstrated by the present inventors that polypeptides comprising at least one Alphabody structure can be provided, which can efficiently penetrate through cell membranes, are stable in the intracellular environment and optionally can effectively and specifically bind to and affect the function of an intracellular target located inside the cell. As also shown further herein, the polypeptides described herein can be used to treat various disease indications, by specifically modulating the function of intracellular targets associated with such disease indications and/or by affecting the biological (signaling) pathways in which the intracellular targets are involved.

DETAILED DESCRIPTION OF THE INVENTION

Definitions

As used herein, the singular forms 'a', 'an', and the include both singular and plural referents unless the context clearly dictates otherwise.

The terms 'comprising', 'comprises' and 'comprised of' as used herein are synonymous with 'including', 'includes' or 'containing', 'contains', and are inclusive or open-ended and do not exclude additional, non-recited members, elements or method steps.

The recitation of numerical ranges by endpoints includes all numbers and fractions subsumed within the respective ranges, as well as the recited endpoints.

The term 'about' as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed methods. It is to be understood that the value to which the modifier 'about' refers is itself also specifically, and preferably, disclosed.

As used herein, an 'Alphabody' or an 'Alphabody structure' can generally be defined as self-folded, single-chain, triple-stranded, predominantly alpha-helical, coiled coil amino acid sequences, polypeptides or proteins. More particularly, an Alphabody or Alphabody structure as used herein can be defined as amino acid sequences, polypeptides or proteins having the general formula HRS1-L1-HRS2-L2-HRS3, wherein each of HRS1, HRS2 and HRS3 is independently a heptad repeat sequence (HRS) comprising 2 to 7 consecutive but not necessarily identical heptad repeat units generally represented by abcdefg or defgabc, wherein at least 50% of all heptad a- and d-positions are occupied by isoleucine residues and each HRS starts with an aliphatic or aromatic amino acid at position "a" or "d", and HRS1, HRS2 and HRS3 together form a triple-stranded, alpha-helical, coiled coil structure; and each of L1 and L2 are independently a linker fragment, as further defined hereinafter, which covalently connect HRS1 to HRS2 and HRS2 to HRS3, respectively. In particular embodiments of the Alphabody structure envisaged herein each HRS ends with a partial heptad sequence abcd or defga such that each HRS starts and ends with an aliphatic or aromatic amino acid residue located at either a heptad a- or d-position.

As used herein, a 'parallel Alphabody' shall have the meaning of an Alphabody (structure) wherein the alpha-helices of the triple-stranded, alpha-helical, coiled coil structure together form a parallel coiled coil structure, i.e., a coiled coil wherein all three alpha-helices are parallel.

As used herein, an 'antiparallel Alphabody' shall have the meaning of an Alphabody (structure) wherein the alpha-helices of the triple-stranded, alpha-helical, coiled coil structure together form an antiparallel coiled coil structure, i.e., a coiled coil wherein two alpha-helices are parallel and the third alpha-helix is antiparallel with respect to these two helices.

As will become clear from the further description herein polypeptides are also provided comprising a sequence with the general formula HRS1-L1-HRS2-L2-HRS3, but which in certain particular embodiments comprise further groups, moieties and/or residues, which are covalently linked, more particularly N- and/or C-terminal covalently linked, to a basic Alphabody structure having the formula HRS1-L1-HRS2-L2-HRS3 in the formula N-HRS1-L1-HRS2-L2-HRS3-C. The optional N and C extensions can be, for example, a tag for detection or purification (e.g. a His-tag) or another protein or protein domain (e.g. a toxin). However the optional extensions N and C do not form part of the Alphabody structure. Thus reference is made herein generally to '(Alphabody) polypeptides' which comprise an Alphabody. The binding features described for an Alphabody herein can generally also be applied to Alphabody polypeptides comprising said Alphabody. The Alphabody polypeptides as provided herein are characterized by the presence of at least one triple-helix structure (consisting of three helixes) which as such forms a coiled coil.

The terms 'heptad', 'heptad unit' or 'heptad repeat unit' are used interchangeably herein and shall herein have the meaning of a 7-residue (poly)peptide fragment that is repeated two or more times within each heptad repeat sequence of an Alphabody, polypeptide or composition envisaged herein and is represented as 'abcdefg' or 'defgabc', wherein the symbols 'a' to 'g' denote conventional heptad positions. Conventional heptad positions are assigned to specific amino acid residues within a heptad, a heptad unit, or a heptad repeat unit, present in an Alphabody, polypeptide or composition envisaged herein, for example, by using specialized software such as the COILS method of Lupas et al. (Science 1991, 252:1162-1164; http://www.russell.embl-heidelberg.de/cgi-bin/coils-svr.pl). However, it is noted that the heptads or heptad units as present in the Alphabody structures of the polypeptides envisaged herein are not strictly limited to the above-cited representations (i.e. 'abcdefg' or 'defgabc') as will become clear from the further description herein and in their broadest sense constitute a 7-residue (poly)peptide fragment per se, comprising at least assignable heptad positions a and d.

The terms 'heptad a-positions', 'heptad b-positions', 'heptad c-positions', 'heptad d-positions', 'heptad e-positions', 'heptad f-positions' and 'heptad g-positions' refer respectively to the conventional a, b, c, d, e, f and 'g' amino acid positions in a heptad, heptad repeat or heptad repeat unit of an Alphabody or polypeptide.

A 'heptad motif' as used herein shall have the meaning of a 7-residue (poly)peptide pattern. A 'heptad motif' of the type 'abcdefg' can usually be represented as 'HPPHPPP', whereas a 'heptad motif' of the type 'defgabc' can usually represented as 'HPPPHPP', wherein the symbol 'H' denotes an apolar or hydrophobic amino acid residue and the symbol 'P' denotes a polar or hydrophilic amino acid residue. However, it is noted that the heptad motifs as present in the Alphabodies or polypeptides are not strictly limited to the above-cited representations (i.e. 'abcdefg', 'HPPHPPP', 'defgabc' and 'HPPPHPP') as will become clear from the further description herein.

A 'heptad repeat sequence" ('HRS') as used herein shall have the meaning of an amino acid sequence or sequence fragment comprising n consecutive (but not necessarily identical) heptads, where n is a number equal to or greater than 2.

In the context of the single-chain structure of the Alphabodies (as defined herein) the terms 'linker', 'linker fragment' or 'linker sequence' are used interchangeably herein and refer to an amino acid sequence fragment that is part of the contiguous amino acid sequence of a single-chain Alphabody, and which covalently interconnects the HRS sequences of that Alphabody.

An 'alpha-helical part of an Alphabody' shall herein have the meaning of that part of an Alphabody which has an alpha-helical secondary structure. Furthermore, any part of the full part of an Alphabody having an alpha-helical secondary structure is also considered an alpha-helical part of an Alphabody. More particularly, in the context of a binding site, where one or more amino acids located in an alpha-helical part of the Alphabody contribute to the binding site, the binding site is considered to be formed by an alpha-helical part of the Alphabody.

A 'solvent-oriented' or 'solvent-exposed' region of an alpha-helix of an Alphabody shall herein have the meaning of that part on an Alphabody which is directly exposed or which comes directly into contact with the solvent, environment, surroundings or milieu in which it is present. Furthermore, any part of the full part of an Alphabody which is directly exposed or which comes directly into contact with the solvent is also considered a solvent-oriented or solvent-exposed region of an Alphabody. More particularly, in the context of a binding site, where one or more amino acids located in a solvent-oriented part of the Alphabody contribute to the binding site, the binding site is considered to be formed by a solvent-oriented part of the Alphabody.

The term 'groove of an Alphabody' shall herein have the meaning of that part on an Alphabody which corresponds to the concave, groove-like local shape, which is formed by any pair of spatially adjacent alpha-helices within an Alphabody.

As used herein, amino acid residues will be indicated either by their full name or according to the standard three-letter or one-letter amino acid code.

As used herein, the term 'homology' denotes at least secondary structural similarity between two macromolecules, particularly between two polypeptides or polynucleotides, from same or different taxons, wherein said similarity is due to shared ancestry. Hence, the term 'homologues' denotes so-related macromolecules having said secondary and optionally tertiary structural similarity. For comparing two or more nucleotide sequences, the '(percentage of) sequence identity' between a first nucleotide sequence and a second nucleotide sequence may be calculated using methods known by the person skilled in the art, e.g. by dividing the number of nucleotides in the first nucleotide sequence that are identical to the nucleotides at the corresponding positions in the second nucleotide sequence by the total number of nucleotides in the first nucleotide sequence and multiplying by 100% or by using a known computer algorithm for sequence alignment such as NCBI Blast. In determining the degree of sequence identity between two Alphabodies, the skilled person may take into account so-called 'conservative' amino acid substitutions, which can generally be described as amino acid substitutions in which an amino acid residue is replaced with another amino acid residue of similar chemical structure and which has little or essentially no influence on the function, activity or other biological properties of the polypeptide. Possible conservative amino acid substitutions will be clear to the person skilled in the art. Alphabodies and nucleic acid sequences are said to be 'exactly the same' if they have 100% sequence identity over their entire length.

An (Alphabody) polypeptide or Alphabody is said to 'specifically bind to' a particular target when that Alphabody or polypeptide has affinity for, specificity for and/or is specifically directed against that target (or for at least one part or fragment thereof).

The 'specificity' of the binding an Alphabody or polypeptide as used herein can be determined based on affinity and/or avidity. The 'affinity' of an Alphabody or polypeptide is represented by the equilibrium constant for the dissociation of the Alphabody or polypeptide and the target protein of interest to which it binds. The lower the KD value, the stronger the binding strength between the Alphabody or polypeptide and the target protein of interest to which it binds. Alternatively, the affinity can also be expressed in terms of the affinity constant (KA), which corresponds to 1/KD. The binding affinity of an Alphabody or polypeptide can be determined in a manner known to the skilled person, depending on the specific target protein of interest. It is generally known in the art that the KD can be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or M$^{-1}$ s$^{-1}$). A KD value greater than about 1 millimolar is generally considered to indicate non-binding or non-specific binding.

The 'avidity' of an Alphabody or polypeptide against a given target is the measure of the strength of binding between an Alphabody or polypeptide and the given target protein of interest. Avidity is related to both the affinity between a binding site on the target protein of interest and a binding site on the Alphabody or polypeptide and the number of pertinent binding sites present on the Alphabody or polypeptide.

An Alphabody or polypeptide is said to be 'specific for a first target protein of interest as opposed to a second target protein of interest' when it binds to the first target protein of interest with an affinity that is at least 5 times, such as at least 10 times, such as at least 100 times, and preferably at least 1000 times higher than the affinity with which that Alphabody or polypeptide binds to the second target protein of interest. Accordingly, in certain embodiments, when an Alphabody or polypeptide is said to be 'specific for' a first target protein of interest as opposed to a second target protein of interest, it may specifically bind to (as defined herein) the first target protein of interest, but not to the second target protein of interest.

The 'half-life' of an Alphabody or polypeptide can generally be defined as the time that is needed for the in vivo serum or plasma concentration of the Alphabody or polypeptide to be reduced by 50%. The in vivo half-life of an Alphabody or polypeptide can be determined in any manner known to the person skilled in the art, such as by pharmacokinetic analysis. As will be clear to the skilled person, the half-life can be expressed using parameters such as the t½-alpha, t½-beta and the area under the curve (AUC). An increased half-life in vivo is generally characterized by an increase in one or more and preferably in all three of the parameters t½-alpha, t½-beta and the area under the curve (AUC).

As used herein, the terms 'inhibiting', 'reducing' and/or 'preventing' may refer to (the use of) a polypeptide as envisaged herein that specifically binds to a target protein of interest and inhibits, reduces and/or prevents the interaction between that target protein of interest, and its natural binding partner. The terms 'inhibiting', 'reducing' and/or 'preventing' may also refer to (the use of) a polypeptide as envisaged herein that specifically binds to a target protein of interest and inhibits, reduces and/or prevents a biological activity of that target protein of interest, as measured using a suitable in vitro, cellular or in vivo assay. Accordingly, 'inhibiting', 'reducing' and/or 'preventing' may also refer to (the use of) a polypeptide that specifically binds to a target protein of interest and inhibits, reduces and/or prevents one or more biological or physiological mechanisms, effects, responses, functions pathways or activities in which the target protein of interest is involved. Such an action of the polypeptide as an antagonist may be determined in any suitable manner and/or using any suitable (in vitro and usually cellular or in vivo) assay known in the art, depending on the target protein of interest.

As used herein, the terms 'enhancing', 'increasing' and/or 'activating' may refer to (the use of) a polypeptide that specifically binds to a target protein of interest and enhances, increases and/or activates the interaction between that target protein of interest, and its natural binding partner. The terms 'enhancing', 'increasing' and/or 'activating' may also refer to (the use of) a polypeptide that specifically binds to a target protein of interest and enhances, increases and/or activates a biological activity of that target protein of interest, as measured using a suitable in vitro, cellular or in vivo assay. Accordingly, 'enhancing', 'increasing' and/or 'activating' may also refer to (the use of) a polypeptide that specifically binds to a target protein of interest and enhances, increases and/or activates one or more biological or physiological mechanisms, effects, responses, functions pathways or activities in which the target protein of interest is involved. Such an action of a polypeptide as envisaged herein as an agonist may be determined in any suitable manner and/or using any suitable (in vitro and usually cellular or in vivo) assay known in the art, depending on the target protein of interest.

The inhibiting or antagonizing activity or the enhancing or agonizing activity of a polypeptide as envisaged herein may be reversible or irreversible, but for pharmaceutical and pharmacological applications will typically occur reversibly.

An Alphabody or polypeptide or a nucleic acid sequence is considered to be '(in) essentially isolated (form)' as used herein, when it has been extracted or purified from the host cell and/or medium in which it is produced.

In respect of the Alphabodies or Alphabody structures comprised within the polypeptides envisaged herein the terms 'binding region', 'binding site' or 'interaction site' present on the Alphabodies shall herein have the meaning of a particular site, part, domain or fragment of amino acid residues present on the Alphabodies that is responsible for binding to a target molecule. Such binding region is formed by specific amino acid residues from the Alphabody which are in contact with the target molecule.

An Alphabody or polypeptide is said to show 'cross-reactivity' for two different target proteins of interest if it is specific for (as defined herein) both of these different target proteins of interest.

An Alphabody or polypeptide is said to be 'monovalent' if the Alphabody contains one binding site directed against or specifically binding to a site, determinant, part, domain or fragment of amino acid residues of the target of interest. In cases wherein two or more binding sites of an Alphabody or polypeptide are directed against or specifically bind to the same site, determinant, part, domain or fragment of amino acid residues of the target of interest, the Alphabody or polypeptide is said to be 'bivalent' (in the case of two binding sites on the Alphabody or polypeptide) or multivalent (in the case of more than two binding sites on the Alphabody or polypeptide), such as for example trivalent.

The term ti-specific' when referring to an Alphabody or polypeptide implies that either a) two or more of the binding sites of an Alphabody or polypeptide are directed against or specifically bind to the same target of interest but not to the same (i.e. to a different) site, determinant, part, domain or fragment of amino acid residues of that target, the Alphabody is said to be 'bi-specific' (in the case of two binding sites on the Alphabody) or multispecific (in the case of more than two binding sites on the Alphabody) or b) two or more binding sites of an Alphabody are directed against or specifically bind to different target molecules of interest. The term 'multispecific' is used in the case that more than two binding sites are present on the Alphabody.

Accordingly, a 'bispecific Alphabody (or polypeptide)' or a 'multi-specific Alphabody (or polypeptide)' as used herein, shall have the meaning of (a polypeptide comprising) a single-chain Alphabody structure of the formula (N-)HRS1-L1-HRS2-L2-HRS3(-C) comprising respectively two or at least two binding sites, wherein these two or more binding sites have a different binding specificity. Thus, an Alphabody (or polypeptide) is herein considered 'bispecific' or 'multi-specific' if respectively two or more than two different binding regions exist in the same, monomeric, single-domain Alphabody.

As used herein, the term 'prevention and/or treatment' comprises preventing and/or treating a certain disease and/or disorder, preventing the onset of a certain disease and/or disorder, slowing down or reversing the progress of a certain disease and/or disorder, preventing or slowing down the onset of one or more symptoms associated with a certain disease and/or disorder, reducing and/or alleviating one or more symptoms associated with a certain disease and/or disorder, reducing the severity and/or the duration of a certain disease and/or disorder, and generally any prophylactic or therapeutic effect of the polypeptides envisaged herein that is beneficial to the subject or patient being treated.

As used herein, the term 'biological membrane' or 'membrane' refers to a lipid-containing barrier which separates cells or groups of cells from extracellular space. Biological membranes include, but are not limited to, plasma membranes, cell walls, intracellular organelle membranes, such as the mitochondrial membrane, nuclear membranes, and the like.

All documents cited in the present specification are hereby incorporated by reference in their entirety. Unless otherwise defined, all terms used in the present disclosure, including technical and scientific terms, have the meaning as commonly understood by one of ordinary skill in the art to which the described contribution to the art belongs. By means of further guidance, term definitions are included to better appreciate the teaching of the present disclosure.

[Invention-Related Description]

It has been found that Alphabody polypeptides can be generated which are capable of entering into the cell and remain stable within the cell. In particular embodiments, the polypeptides envisaged herein can further specifically bind to and modulate the function of an intracellular target in that cell. More particularly, Alphabody polypeptides have been obtained which—as opposed to prior art polypeptides comprising an Alphabody—are modified so as to allow their internalization into cells (i.e. intracellular uptake). In addition, it has been found that the Alphabody polypeptides as envisaged herein can be provided which bind to intracellular targets with affinities that are higher or at least comparable to those of traditional binding agents, and thus are capable of directly affecting intracellular processes.

It will be clear to the skilled person that the Alphabody sequences disclosed in the prior art do not contain the particular combination of structural features of the polypeptides provided herein. Accordingly, it will be clear to the skilled person that the Alphabody sequences disclosed in the prior art, which include:

SEQ ID NO: 4 to 10 in published application WO 2010/066740 in the name of Complix NV, SEQ ID NO's: 1 to 5, 10, 17, 22, 24, 27, 32, and 36 in published application WO2011/003935 in the name of Complix NV, SEQ ID NO: 2 to 7 in published application WO 2011/003936 in the name of Complix NV, SEQ ID NO's: 1 to 85 in published application WO 2012/092970, in the name of Complix NV, SEQ ID NO's: 1 to 4 and 8 in published application WO 2012/092971 in the name of Complix NV, SEQ ID NO's: 64 to 69, 71 to 75, and 77 to 80 in published application WO 2012/093013 in the name of Complix NV, and SEQ ID NO's: 1 to 135 in published application WO 2012/093172 in the name of Complix NV, do not comprise an internalization region as envisaged herein and thus are not encompassed by the present invention.

The polypeptides described herein are capable of efficiently crossing the biological cell membrane. Intracellular transport of biologically active molecules is usually one of the key problems in drug delivery in general, since the lipophilic nature of the biological membranes restricts the direct intracellular delivery of such compounds. The cell membrane prevents big molecules such as peptides, proteins and DNA from spontaneously entering cells unless there is an active transport mechanism involved.

Unique and highly potent polypeptides are provided herein, which are capable of autonomously entering a cell by crossing the cell membrane, and maintaining full activity and functionality in the intracellular environment. In particular embodiments, the polypeptides provided are further characterized in that they are capable of interacting specifically and with high affinity with an intracellular target of interest.

While the alpha-helical coiled coil structure of Alphabodies in itself does not confer membrane penetrating capacity, a new and improved technology is described herein to bring polypeptides comprising one or more Alphabody structures into the cell, which involves the design of specific amino acid regions, optionally including a sequence pattern or motif, at least in part in the Alphabody scaffold. Thus, the polypeptides as envisaged herein are capable of entering into the cell as the result of a particular motif present at least in part within the Alphabody structure and do not require and thus are not envisaged to comprise cell-penetrating peptides linked to the Alphabody structure. More particularly, in particular embodiments the polypeptides as envisaged herein do not comprise a stretch of more than 3, more particularly not more than 2 consecutive arginines or lysines outside the Alphabody structure sequence. In particular embodiments, the polypeptides envisaged herein do not comprise an arginine or lysine outside of the Alphabody structure sequence.

A new and highly efficient cell penetrating technology has been developed which is referred to herein as the "CPAB technology", which allows to transform polypeptides comprising Alphabodies into highly effective cell penetrating molecules, i.e. so-called "Cell Penetrating Alphabodies" (CPAB) or "Cell Penetrating Alphabody Polypeptides".

The design of a particular CPAB Alphabody polypeptide by means of the CPAB technology involves at least the step of manufacturing or modifying a polypeptide comprising an Alphabody structure sequence so as to obtain an amino acid region comprised at least partly within the Alphabody structure sequence of the polypeptide, which amino acid region ensures internalization of the polypeptide into the cell. Thus, the design of a particular CPAB Alphabody comprises introducing (e.g. by sequence design or by mutation) one or more internalization regions into the Alphabody sequence or part thereof. In particular embodiments, this comprises introducing specific amino acid residues at specific positions in the sequence of an Alphabody scaffold.

It has been found that by introducing such an internalization region at least in part into an Alphabody sequence, a polypeptide can be created which is able to penetrate the cell autonomously, i.e. without the need for any other structure enabling penetration into the cell. Moreover, as will be detailed below, it has been found that this can optionally be combined with the provision of a binding site to an intracellular target within the Alphabody structure, such that highly efficient intracellular binding agents are obtained.

The CPAB polypeptides provided herein have been designed to contain certain types of amino acid residues within one or more limited regions in a polypeptide comprising an Alphabody structure, more particularly at least in part within the Alphabody structure. More particularly, it has been found that specific positively charged (also referred to as cationic) regions work particularly well to ensure internalization of the polypeptides. Thus, in particular embodiments, the polypeptides envisaged herein comprise at least one positively charged internalization region, that is characterized by a number of positively charged amino acid residues at specific positions of the Alphabody scaffold, through which the polypeptides are provided with the capacity to enter cells. In certain embodiments, the at least one positively charged internalization region can be considered to contain a "cell penetrating motif" or a "cell penetrating pattern" (also referred to herein as a "CPAB motif" or "CPAB pattern"). Such a motif or pattern can be considered characteristic for providing the polypeptides envisaged herein with cell penetrating activity.

In a first aspect, polypeptides are provided herein comprising at least one Alphabody structure sequence and at least one positively charged internalization region ensuring internalization of said polypeptide into a cell, wherein said internalization region is comprised at least in part within said Alphabody structure sequence.

A positively charged internalization region is to be considered as being a sequence, which is at least part of an Alphabody structure sequence (as defined herein) and which extends between two positively charged amino acid residues of the polypeptides envisaged herein.

In the context of the present invention, the term "positively charged amino acid(s)" refers to (an) amino acid(s) selected from the group consisting of arginine and lysine.

Thus, the polypeptides provided herein comprise a positively charged sequence that starts with a positively charged amino acid residue and ends with a positively charged amino acid residue and which ensures that the polypeptides are capable of entering the cell.

It will be clear to the skilled person that the polypeptides as envisaged herein may contain (but not necessarily contain) additional positively charged amino acid residues that are located outside an internalization region as envisaged herein. Thus, a certain number of positively charged amino acid residues may be present in the polypeptides as envisaged herein, which do not form part of an internalization region as described herein and which are thus not considered to contribute to the cell penetrating capacity of the polypeptides. Furthermore, the polypeptides as envisaged herein, may or may not contain two or more internalization regions as described herein, which are located separate from each other or which are overlapping each other.

The at least one positively charged internalization region of the polypeptides envisaged herein, is further characterized by the presence of at least six positively charged amino acid residues. The at least six amino acid residues can be chosen from the group consisting of arginine and lysine. Indeed, the present inventors have found that when six or more positively charged amino acid residues, such as arginines or lysines or a mixture of arginines and lysines, are clustered at certain locations within the polypeptides envisaged herein, highly efficient entry into cells of the polypeptides is ensured.

Furthermore, it has been observed that when at least four residues of the at least six positively charged residues in the internalization region are arginines or when at least five residues of the at least six positively charged residues in the internalization region are lysines highly efficient cell penetration is observed.

The internalization region comprised in the polypeptides as envisaged herein is a fragment of amino acids which (i) extends between two positively charged amino acid residues, (ii) is characterized by the presence of at least six positively charged amino acid residues. In particular embodiments it is further characterized in that it (iiia) consists of maximally 16 amino acids, or
(iiib) consists for at least 35% of positively charged amino acids.

It will be clear to the skilled person that the Alphabody sequences of the prior art do not contain this particular combination of structural features of the polypeptides provided herein. In line therewith, the Alphabody sequences of the prior art are not encompassed by the present invention.

Thus, the positively charged internalization region as described herein can be a fragment of maximally 16 amino acids extending between two positively charged amino acid residues, which is characterized by the presence of at least six positively charged amino acid residues. In certain particular embodiments, the internalization region is a fragment of 16 amino acids, which is delimited by two positively charged amino acids and which is characterized by the presence of at least six positively charged amino acid residues. In further particular embodiments, the internalization region is a fragment of 16 amino acids that comprises 6, 7, 8, 9, or 10, or more, such as 16 positively charged amino acids and which is delimited by two positively charged amino acids.

In further particular embodiments, the region is a fragment of 16 amino acids delimited by two positively charged amino acids and characterized by the presence of at least six positively charged amino acids, of which at least four residues are arginines or of which at least five residues are lysines.

In further particular embodiments, the internalization region can comprise 7, 8, 9, 10 or more, such as 16 positively charged amino acids, comprising a combination of arginines and lysines which adds up to a total of 7, 8, 9, 10, or more than 10, such as 16 positively charged amino acids. Such combinations of positively charged amino acid residues include for example a combination of 4 arginines and 3 lysines, 5 arginines and 3 lysines, 6 arginines and 4 lysines, 4 arginines and 4 lysines, 5 arginines and 4 lysines, 5 arginines and 5 lysines, 6 arginines and 3 lysines, and any suitable other combination of arginines and lysines adding up to a maximum total of 16 positively charged amino acid residues.

In further particular embodiments, the internalization region can comprise at least 4, such as 5, 6, 7, 8, 9, 10, or more than 10 such as maximum 16 arginines. In further particular embodiments, the internalization region can comprise at least five, such as 6, 7, 9, 10 or more than 10 such as maximum 16 lysines.

In certain embodiments of the present invention, the at least six positively charged amino acid residues within a positively charged internalization region comprised in the polypeptides envisaged herein exclusively consist of arginines or exclusively consist of lysines. Alternatively, in certain particular embodiments, the at least six positively charged amino acid residues within a positively charged internalization region comprised in the polypeptides envisaged herein consist of arginines and lysines.

It has been found by the present inventors that positive charges clustered close to each other in the polypeptide sequences comprising an Alphabody structure sequence enhance cell penetration of the polypeptides.

Thus, the at least one positively charged internalization region envisaged herein can be a fragment which extends between two positively charged amino acid residues, which is characterized by the presence of at least six positively charged amino acid residues and which consists for at least 35% of positively charged amino acids. In particular embodiments, the at least one positively charged internalization region as envisaged herein, consists for at least 35% of positively charged amino acids, such as for at least 40%, 45%, 50%, 55%, 60%, 70%, 75%, 80%, 85%, 90%, 95%, or maximally 100% of positively charged amino acid residues. The positively charged amino acid residues can be arginines or lysines. In further particular embodiments, the at least one positively charged internalization region in the polypeptides as envisaged herein, consists for at least 35% of positively charged amino acids and is characterized by the presence of at least six positively charged amino acid residues, of which at least four residues are arginines. In further particular embodiments, the at least one positively charged internalization region in the polypeptides as envisaged herein, consists for at least 35% of positively charged amino acids and is characterized by the presence of at least six positively charged amino acid residues, of which at least five residues are lysines.

Indeed, the present inventors have surprisingly found that when a distinct, and relatively short fragment of amino acid residues—at least partially, and preferably entirely, located within the Alphabody structure—is decorated or provided with a number of positively charged amino acid residues that are located close to each other, a polypeptide can be generated with highly favourable properties in terms of both cell penetration and intracellular stability and functionality.

While in the prior art many attempts have been made to positively charge or cationize proteins in a random manner, essentially spreading charges over the entire protein surface, in order to enhance cell penetration, many side effects were observed and no functionality inside cells could be demonstrated. These side effects for example included aspecific binding or stickiness to cellular organelles and membranes, unstability and electrostatic repulsion due to "overchargement", denaturation resulting in aggregation and false interactions with for instance membrane components and acidic proteins.

It has however now been found by the present inventors that positive charges located close to each other in a narrow window of the polypeptide sequences comprising an Alphabody structure sequence, i.e. a window corresponding to about 15 to 20 amino acid residues, and preferably not more than 16 amino acid residues, cell penetration of the polypeptides can be optimally achieved.

In particular embodiments envisaged herein, the positive charges in the internalization region of the polypeptides as described herein, are located close to each other in a narrow window within the polypeptide. The positively charged internalization region is envisaged to be located at least in part within the Alphabody structure generally represented by HRS1-L1-HRS2-L2-HRS3, in the polypeptide. More particularly, at least 50% of the positively charged amino acids of the internalization region are located within the Alphabody structure. For this assessment, the internalization region is considered to be the longest stretch of amino acids (up to but not exceeding 16AA) extending between two positively charged amino acids and comprising at least 6 positively charged amino acids). In certain particular embodiments, at least 60%, such as at least 70%, 80%, 90% or 100% (i.e. all) of the positively charged amino acid residues within an internalization region as envisaged herein are comprised within the Alphabody structure sequence of the polypeptides provided herein. In further particular embodiments of the polypeptides envisaged herein, at least 80% of the internalization region is integrated into (or fully comprised within) the Alphabody structure (e.g. at least about $13/16$ amino acids are located within the Alphabody structure in the polypeptide), such that a limited number of amino acids (e.g. at most about $3/16$ amino acids) extend in the polypeptide outside the Alphabody structure. Moreover it will be understood that the polypeptides envisaged herein do not encompass In particular embodiments however, the entire internalization region is located within the Alphabody structure sequence.

In particular embodiments, the at least one internalization region is entirely or fully comprised within one alpha-helix (HRS1, HRS2 or HRS3) of said at least one Alphabody structure sequence. In further particular embodiments, the at least one internalization region is comprised within a region corresponding to the overlap between an alpha-helix and a linker (HRS1-L1, L1-HRS2, HRS2-L2, L2-HRS3). In yet further embodiments, the at least one internalization region is located within a linker (L1, L2).

The positively charged amino acids within this internalization region need not be positioned next to each other, but can be separated by one or more non-positively charged amino acids. Indeed, the skilled person will recognize that certain limitations are imposed by the Alphabody motif. Typically, the internalization region is considered to extend between two positively charged amino acid residues most remotely positioned from each other within a fragment of maximally 16 amino acid residues.

The position of the positively charged amino acids of the internalization region in the Alphabody will influence the effectiveness of internalization. Indeed, in particular embodiments one or more positively charged amino acid residues of the internalization region are located at the outer surface of an Alphabody, in particular on the solvent-oriented outer surface of the Alphabody, such as on the outer, solvent-oriented surface of at least one alpha-helix of an Alphabody. Indeed, it has been found that internalization is improved if the positively charged amino acid residues of the internalization region are located at the outer surface of the Alphabody structure or scaffold. Thus, in particular embodiments, the positively charged amino acids of the internalization region are located on the outer surface of an alpha-helix of an Alphabody structure in the polypeptide, more particularly (exclusively) on the outer surface of an alpha-helix of an Alphabody structure.

In view of the above, it has been established that improved internalization can be obtained if the positively charged amino acids are provided in specific positions in the Alphabody structure. Thus, in particular embodiments, the internalization region comprises a specific motif of positively charged amino acids. Such a motif or pattern is thus a distinct amino acid sequence at the protein level (or nucleic acid sequence at the genetic level), which comprises one or more characteristic amino acid residues at specific positions (or nucleic acid sequence encoding said amino acid residues). The "characteristic amino acid residues" within a certain CPAB motif (as used herein), represent those amino acid residues within that CPAB motif, which are critical to the cell penetrating capability of the CPAB Alphabody comprising that CPAB motif. Thus, changing the identity of so-called "characteristic or critical residues" of a CPAB motif in a CPAB Alphabody (e.g. by mutation or de novo sequence design) will affect the cell penetrating capability of that CPAB Alphabody.

In certain particular embodiments, a CPAB motif of an internalization region as envisaged herein is no longer capable of mediating cellular internalization of a polypeptide when the number of positively charged amino acid residues is reduced to less than 4.

As detailed above, a positively charged internalization region, a CPAB motif or CPAB pattern as used herein is at least in part, integrated into the Alphabody structure sequence as such (as defined herein) and thus different from a cell penetrating peptide or protein sequence or other cell penetrating group that is conjugated or attached to one of the ends of an Alphabody sequence so as to ensure cell penetration.

It has been found that the location of an internalization region within the Alphabody structure of a polypeptide is not critical, i.e. a positively charged internalization region as envisaged herein can be positioned in helix A, B, or C of the Alphabody structure.

In particular embodiments, the polypeptides as provided herein comprise at least one internalization region, which is located in helix A of the Alphabody structure. In further particular embodiments, the polypeptides as provided herein comprise at least one internalization region, which is located in helix C of the Alphabody structure. In further particular embodiments, the polypeptides as provided herein comprise two internalization regions, each of which is located in helix A and in helix C of the Alphabody structure as described herein.

In certain particular embodiments, it has been found that combinations of two internalization regions in two different parts of the Alphabody structure (e.g. A-helix and C-helix) can also increase permeability into the cell.

However, in particular embodiments, it is preferred that the internalization region is not comprised in the loops or linker regions of an Alphabody structure. In further particular embodiments, it is envisaged that at most two out of three helices of an Alphabody structure comprise an internalization region.

In further particular preferred embodiments, the polypeptides as envisaged herein comprise at least one internalization region, which is exclusively located and substantially entirely comprised within one alpha-helix of the Alphabody structure, such as the A-helix, the B-helix or the C-helix. In further particular embodiments, the polypeptides as envisaged herein comprise at least one internalization region, which is exclusively located and substantially entirely comprised within one alpha-helix of the Alphabody structure, such as the A-helix or the C-helix.

In particular embodiments, the positively charged amino acids are located at conventional heptad b-, c-, e-, f- and g-positions, i.e. non-core positions (as defined herein) of the Alphabody scaffold, which positions are typically located at the outer, i.e. solvent-exposed, alpha-helix surface of the Alphabody scaffold.

Accordingly, in particular embodiments, a CPAB motif can for example (without limitation) be present in the following fragment of 16 amino acids that is comprised within the heptad repeat sequence of one or more of the helices of an Alphabody structure: XXHXXXHXXHXXX-HXX, wherein H represents a hydrophobic and/or apolar amino acid residue, wherein X represents a hydrophilic and/or polar amino acid residue, and wherein at least six X residues are either arginine or lysine.

In particular embodiments, H represents isoleucine.

In still further particular embodiments, the motif is a subfragment of the 16 amino acid fragment XXHXXX-HXXHXXXHXX that is comprised within the heptad repeat sequence of one or more of the helices of an Alphabody structure, wherein H represents a hydrophobic and/or apolar amino acid residue, wherein X represents a hydrophilic and/or polar amino acid residue, and provided that at least six of the X residues are either arginine or lysine. In particular embodiments, H represents isoleucine.

Different useful positively charged internalization motifs have been identified by the present inventors. The following represents a non-limiting number of examples thereof.

(i) In particular embodiments, the CPAB motif corresponds to ZZXXZXXZZXXZ, wherein Z represents a positively charged amino acid and X represents any amino acid residue. More particularly, this CPAB motif is positioned within the heptad repeat sequence of one or more of the helices of an Alphabody structure. In particular embodiments, positioning of this motif on a helix structure characterized by the structure HPPHPPPHPPHPPPHPPPHPP corresponds to HZZHPZPHZZHPZPHPPHPPPHPP such that the positively charged amino acids (Z) are located on the outer surface of the helix. In particular embodiments, H is Isoleucine and Z is Z is Arginine, such that the motif corresponds to Ile-Xaa-Xaa-Ile-Xaa-Xaa-Xaa-Ile-Arg-Xaa-Ile-Arg-Arg-Xaa-Ile-Arg-Xaa-Ile-Arg-Arg-Xaa-Ile-Xaa-Xaa (SEQ ID NO: 22).

(xi) In further particular embodiments, the CPAB motif corresponds to ZZXXZXXXZXXZZXXZZXZZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to HPPHZZPHZPHPZPHZZHPZZHZZ. In particular embodiments, H is Isoleucine and Z is Arginine, such that the motif corresponds to Ile-Xaa-Xaa-Ile-Arg-Arg-Xaa-Ile-Arg-Xaa-Ile-Xaa-Arg-Xaa-Ile-Arg-Arg-Ile-Xaa-Arg-Arg-Ile-Arg-Arg (SEQ ID NO: 23).

(xii) In further particular embodiments, the CPAB motif corresponds to ZZXXZXXXZXXZZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to HPPHZZPHZPHPZ-PHZZHPPPHPP. In particular embodiments, H is Isoleucine and Z is Arginine, such that the motif corresponds to Ile-Xaa-Xaa-Ile-Arg-Arg-Xaa-Ile-Arg-Xaa-Ile-Xaa-Arg-Xaa-Ile-Arg-Arg-Ile-Xaa-Xaa-Xaa-Ile-Xaa-Xaa (SEQ ID NO: 24).

(xiii) In further particular embodiments, the CPAB motif corresponds to ZXXZXXXZXXZZXXZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to HPPH-PZPHZPHPZPHZZHPZPHPP. In particular embodiments, H is Isoleucine and Z is Arginine, such that the motif corresponds to Ile-Xaa-Xaa-Ile-Xaa-Arg-Xaa-Ile-Arg-Xaa-Ile-Xaa-Arg-Xaa-Ile-Arg-Arg-Ile-Xaa-Arg-Xaa-Ile-Xaa-Xaa (SEQ ID NO: 25).

(xiv) In further particular embodiments, the CPAB motif corresponds to ZXXXZXXZZXXZZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to HPPHPPPHZPHPZ-PHZZHPZZHPP. In particular embodiments, H is Isoleucine and Z is Arginine, such that the motif corresponds to Ile-Xaa-Xaa-Ile-Xaa-Xaa-Xaa-Ile-Arg-Xaa-Ile-Xaa-Arg-Xaa-Ile-Arg-Arg-Ile-Xaa-Arg-Arg-Ile-Xaa-Xaa (SEQ ID NO: 26).

(xv) In further particular embodiments, the CPAB motif corresponds to ZXXZZXXZZXZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHP-PPHPPHPPPHPP corresponds to HPPHPPPHPPHPZ-PHZZHPZZHZP. In particular embodiments, H is Isoleucine and Z is Arginine, such that the motif corresponds to Ile-Xaa-Xaa-Ile-Xaa-Xaa-Xaa-Ile-Xaa-Xaa-Ile-Xaa-Arg-Xaa-Ile-Arg-Arg-Ile-Xaa-Arg-Arg-Ile-Arg-Xaa (SEQ ID NO: 27).

(xvi) In further particular embodiments, the CPAB motif corresponds to ZZXXZZXZZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHP-PPHPPHPPPHPP corresponds to HPPHPPPHPPHPP-PHZZHPZZHZZ. In particular embodiments, H is Isoleucine and Z is Arginine, such that the motif corresponds to Ile-Xaa-Xaa-Ile-Xaa-Xaa-Xaa-Ile-Xaa-Xaa-Ile-Xaa-Xaa-Xaa-Ile-Arg-Arg-Ile-Xaa-Arg-Arg-Ile-Arg-Arg (SEQ ID NO: 28).

(xvii) In further particular embodiments, the CPAB motif corresponds to ZZXXXXXZZXXXXXZZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to ZZHP-PPHZZHPPPHZZ. In particular embodiments, H is Isoleucine and Z is Arginine, such that the motif corresponds to Arg-Arg-Ile-Xaa-Xaa-Xaa-Ile-Arg-Arg-Ile-Xaa-Xaa-Xaa-Ile-Arg-Arg (SEQ ID NO: 29).

(xviii) In further particular embodiments, the CPAB motif corresponds to ZZXXZXXZZXXZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHP-PPHPPHPPPHPP corresponds to HPPHPPPHZZHPZ-PHZZHPZPHPP. In particular embodiments, H is Isoleucine and Z is Arginine, such that the motif corresponds to Ile-Xaa-Xaa-Ile-Xaa-Xaa-Xaa-Ile-Arg-Arg-Ile-Xaa-Arg-Xaa-Ile-Arg-Arg-Ile-Xaa-Arg-Xaa-Ile-Xaa-Xaa (SEQ ID NO: 30).

(xix) In further particular embodiments, the CPAB motif corresponds to ZZXXZXXZZXXZXXZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to HPPH-PPPHZZHPZPHZZHPZPHZP. In particular embodiments, H is Isoleucine and Z is Arginine, such that the motif corresponds to Ile-Xaa-Xaa-Ile-Xaa-Xaa-Xaa-Ile-Arg-Arg-Ile-Xaa-Arg-Xaa-Ile-Arg-Arg-Ile-Xaa-Arg-Xaa-Ile-Arg-Xaa (SEQ ID NO: 31).

(xx) In further particular embodiments, the CPAB motif corresponds to ZZXXZXXZZXXZXXZZ, wherein Z represents the positively charged amino acids. More particularly, this CPAB motif is positioned within the heptad repeat sequence of one or more of the helices of the Alphabody structure. In particular embodiments, positioning of this motif on a helix structure characterized by the structure HPPHPPPHPPHPPPHPPHPPPHPP corresponds to HPPH-PPPHZZHPZPHZZHPZPHZZ. In particular embodiments, H is Isoleucine and Z is Arginine, such that the motif corresponds to Ile-Xaa-Xaa-Ile-Xaa-Xaa-Xaa-Ile-Arg-Arg-Ile-Xaa-Arg-Xaa-Ile-Arg-Arg-Ile-Xaa-Arg-Xaa-Ile-Arg-Arg (SEQ ID NO: 32).

Thus in particular embodiments, the internalization motif is selected from ZZXXZXXZZXXZ, ZXXZXXZZXXZXXZ, ZXXZZXXZZXXZ, ZXXZXXZZXXXZXXZZ, ZXXXZXXZXXXZXXZ, ZXXXZXXZZXXZ, ZXXZZXXZXXZZ, ZZXXZXXZZXXZ, ZXXZXXZXXZZXXZ, ZXXXZXXZZXXZ, ZXXZZXXZZXZ, ZZXXZZXXZ, ZZ repair, apoptotsis and programmed cell death. The polypeptides as envisaged herein are further capable of maintaining their biological activity in the intracellular environment. Indeed, it has been demonstrated herein that the polypeptides provided herein are not only stable in the intracellular milieu but is also capable of effectively binding their intracellular target and inhibiting the function thereof.

Particular polypeptides as described herein are capable of specifically binding to anti-apoptotic members of the BCL-2 family of proteins. Examples of anti-apoptotic members of the BCL-2 family of proteins are MCL-1, BCL-2, BCL-$X_L$, BCL-w and BFL-1/A1. It should be understood that one Alphabody may bind to several (i.e., one or more) intracellular proteins of interest. In particular embodiments, the binding of the Alphabody is driven by one of its alpha-helices, which is stabilized in the Alphabody coiled coil structure.

In particular embodiments, polypeptides are provided which are capable of being internalized by a cell and capable of binding to MCL-1, whereby the polypeptides are characterized in that they comprise a sequence selected from SEQ ID NO: 3 to 6, 9 and 10.

In particular embodiments, polypeptides are provided which are capable of being internalized by a cell and capable of binding to MCL-1, whereby the polypeptides are characterized in that they comprise a sequence having at least 60%, at least 70%, at least 80%, at least 90%, or more sequence identity with a polypeptide sequence as defined in SEQ ID NO: 7.

In particular embodiments, polypeptides are provided which are capable of being internalized by a cell and capable of binding to MCL-1, whereby the polypeptides are characterized in that they comprise a sequence as defined in SEQ ID NO: 8 (LRXVGDXV).

In particular embodiments, polypeptides are provided which are capable of being internalized by a cell and capable of binding to BCL-2a, whereby the polypeptides are characterized in that they comprise a sequence selected from SEQ ID NO: 9 and 10.

In particular embodiments, polypeptides are provided which are capable of being internalized by a cell and capable of binding to BCL-XL, whereby the polypeptides are characterized in that they comprise a sequence selected from SEQ ID NO: 9 and 10.

In particular embodiments, polypeptides are provided which are capable of being internalized by a cell and capable of binding to BCL-2a and/or BCL-XL, whereby the polypeptides are characterized in that they comprise a sequence having at least 60%, at least 70%, at least 80%, at least 90%, at least 95% or more sequence identity with a polypeptide sequence as defined in SEQ ID NO: 11 (MSIEEIAAQIAAI-QLRIIGDQFNIYYMT).

In particular embodiments, polypeptides are provided which are capable of being internalized by a cell and capable of binding to BCL-2a and/or BCL-XL whereby the polypeptides are characterized in that they comprise a sequence as defined in SEQ ID NO: 12 (LRIIGDQF).

In particular embodiments, the intracellular target molecules to which the Alphabodies and polypeptides as envisaged in certain embodiments can specifically bind include intracellular proteins that are naturally involved in processes occurring in eukaryotic cells, such as animal cells, and in particular mammalian or human cells.

[Binding Affinity of the Alphabody Polypeptides]

Typically, the polypeptides envisaged herein will bind to a target protein of interest with a dissociation constant (KD) of less than about 1 micromolar (1 μM), and preferably less than about 1 nanomolar (1 nM) [i.e., with an association constant (KA) of about 1,000,000 per molar ($10^6$ $M^{-1}$, 1E6/M) or more and preferably about 1,000,000,000 per molar ($10^9$ $M^{-1}$, 1E9/M) or more]. A KD value greater than about 1 millimolar is generally considered to indicate non-binding or non-specific binding. It is generally known in the art that the KD can also be expressed as the ratio of the dissociation rate constant of a complex, denoted as kOff (expressed in seconds$^{-1}$ or s$^{-1}$), to the rate constant of its association, denoted kOn (expressed in molar$^{-1}$ seconds$^{-1}$ or $M^{-1}$ s$^{-1}$). In particular, a polypeptide as disclosed herein will bind to the target protein of interest with a kOff ranging between 0.1 and 0.0001 s$^{-1}$ and/or a kOn ranging between 1,000 and 1,000,000 $M^{-1}$ s$^{-1}$. Binding affinities, kOff and kOn rates may be determined by means of methods known to the person skilled in the art, for example ELISA methods, isothermal titration calorimetry, surface plasmon resonance, fluorescence-activated cell sorting analysis, and the more.

[Structure of the Alphabody Scaffold]

The target-binding polypeptides described herein are amino acid sequences comprising one or more Alphabody scaffolds having the general formula HRS1-L1-HRS2-L2-HRS3, and optionally comprising additional N- and C-terminal linked groups, residues or moieties, wherein each of HRS1, HRS2 and HRS3 is independently a heptad repeat sequence (HRS) comprising 2 to 7 consecutive but not necessarily identical heptad repeat units generally represented by abcdef or defgabc, As indicated above, a heptad repeat unit of an Alphabody structure is generally represented as 'abcdefg' or 'defgabc', wherein the symbols 'a' to 'g' denote conventional heptad positions. The 'a-positions' and 'd-positions' in each heptad unit of an Alphabody as described herein are amino acid residue positions of the coiled coil structure where the solvent-shielded (i.e., buried) core residues are located. The 'e-positions' and 'g-positions' in each heptad unit of an Alphabody structure are amino acid residue positions of the coiled coil structure where the amino acid residues which are partially solvent-exposed are located. In a triple-stranded coiled coil, these 'e-positions' and 'g-positions' are located in the groove formed between two spatially adjacent alpha-helices, and the corresponding amino acid residues are commonly denoted the 'groove residues'. The 'b-positions', 'c-positions' and 'f-positions' in each heptad unit of an Alphabody structure are the most solvent-exposed positions in a coiled coil structure.

A heptad motif (as defined herein) of the type 'abcdefg' is typically represented as 'HPPHPPP', whereas a 'heptad motif' of the type 'defgabc' is typically represented as 'HPPPHPP', wherein the symbol 'H' denotes an apolar or hydrophobic amino acid residue and the symbol 'P' denotes a polar or hydrophilic amino acid residue. Typical hydrophobic residues located at a- or d-positions include aliphatic (e.g., leucine, isoleucine, valine, methionine) or aromatic (e.g., phenylalanine) amino acid residues. Heptads within coiled coil sequences do not always comply with the ideal pattern of hydrophobic and polar residues, as polar residues are occasionally located at 'H' positions and hydrophobic residues at 'P' positions. Thus, the patterns 'HPPHPPP' and 'HPPPHPP' are to be considered as ideal patterns or characteristic reference motifs. Occasionally, the characteristic heptad motif is represented as 'HPPHCPC' or 'HxxHCxC' wherein 'H' and 'P' have the same meaning as above, 'C' denotes a charged residue (lysine, arginine, glutamic acid or aspartic acid) and denotes any (unspecified) natural amino acid residue. Since a heptad can equally well start at a d-position, the latter motifs can also be written as 'HCP- CHPP' or 'HCxCHxx'. It is noted that single-chain Alphabodies are intrinsically so stable that they do not require the aid of ionic interactions between charged ('C') residues at heptad e- and g-positions.

The linkers within a single-chain structure of the Alphabody structure (as defined herein) interconnect the HRS sequences, and more particularly the first to the second HRS, and the second to the third HRS in an Alphabody. Each linker sequence in an Alphabody commences with the residue following the last (partial) heptad residue of the preceding HRS and ends with the residue preceding the first heptad residue of the next HRS. Connections between HRS fragments via disulfide bridges or chemical cross-linking or, in general, through any means of inter-chain linkage (as opposed to intra-chain linkage), are explicitly excluded from the definition of a linker fragment (at least, in the context of an Alphabody) because such would be in contradiction with the definition of a single-chain Alphabody. A linker fragment in an Alphabody is preferably flexible in conformation to ensure relaxed (unhindered) association of the three heptad repeat sequences as an alpha-helical coiled coil structure. Further in the context of an Alphabody, shall denote the linker fragment one, i.e., the linker between HRS1 and HRS2, whereas 'L2' shall denote the linker fragment two, i.e., the linker between HRS2 and HRS3. Suitable linkers for use in the Alphabody structure will be clear to the skilled person, and may generally be any linker used in the art to link amino acid sequences, as long as the linkers are structurally flexible, in the sense that they do not affect the characteristic three dimensional coiled coil structure of the Alphabody. The two linkers L1 and L2 in a particular Alphabody structure, may be the same or may be different. Based on the further disclosure herein, the skilled person will be able to determine the optimal linkers for a specific Alphabody structure, optionally after performing a limited number of routine experiments. In particular embodiments, the linkers L1 and L2 are amino acid sequences consisting of at least 4, in particular at least 8, more particularly at least 12 amino acid residues, with a non-critical upper limit chosen for reasons of convenience being about 30 amino acid residues. In a particular, non-limiting embodiment, preferably at least 50% of the amino acid residues of a linker sequence are selected from the group proline, glycine, and serine. In further non-limiting embodiments, preferably at least 60%, such as at least 70%, such as for example 80% and more particularly 90% of the amino acid residues of a linker sequence are selected from the group proline, glycine, and serine. In other particular embodiments, the linker sequences comprise mainly polar amino acid residues; in such particular embodiments, preferably at least 50%, such as at least 60%, such as for example 70% or 80% and more particularly 90% or up to 100% of the amino acid residues of a linker sequence are selected from the group consisting of glycine, serine, threonine, alanine, proline, histidine, asparagine, aspartic acid, glutamine, glutamic acid, lysine and arginine.

In certain particular embodiments, each of the linkers L1 and L2 in an Alphabody structure are independently a linker fragment, covalently connecting HRS1 to HRS2 and HRS2 to HRS3, respectively, and consisting of at least 4 amino acid residues, preferably at least 50% of which are selected from the group proline, glycine, serine.

In the context of the present disclosure, a 'coiled coil' or 'coiled coil structure' shall be used interchangeably herein and will be clear to the person skilled in the art based on the common general knowledge and the description and further references cited herein. Particular reference in this regard is made to review papers concerning coiled coil structures, such as for example, Cohen and Parry *Proteins* 1990, 7:1-15; Kohn and Hodges *Trends Biotechnol* 1998, 16:379-389; Schneider et al *Fold Des* 1998, 3:R29-R40; Harbury et al. *Science* 1998, 282:1462-1467; Mason and Arndt *ChemBioChem* 2004, 5:170-176; Lupas and Gruber *Adv Protein Chem* 2005, 70:37-78; Woolfson *Adv Protein Chem* 2005, 70:79-112; Parry et al. *J Struct Biol* 2008, 163:258-269; McFarlane et al. *Eur J Pharmacol* 2009:625:101-107.

The 'coiled coil' structure of an Alphabody can be considered as being an assembly of alpha-helical heptad repeat sequences wherein the helical heptad heptad repeat sequences are as defined supra;
  the said alpha-helical heptad repeat sequences are wound (wrapped around each other) with a left-handed super-twist (supercoiling);
  the core residues at a- and d-positions form the core of the assembly, wherein they pack against each other in a knobs-into-holes manner as defined in the Socket algorithm (Walshaw and Woolfson *J Mol Biol* 2001, 307: 1427-1450) and reiterated in Lupas and Gruber *Adv Protein Chem* 2005, 70:37-78;
  the core residues are packed in regular core packing layers, where the layers are defined as in Schneider et al *Fold Des* 1998, 3:R29-R40.

The coiled coil structure of an Alphabody structure is not to be confused with ordinary three-helix bundles. Criteria to distinguish between a true coiled coil and non-coiled coil helical bundles are provided in Desmet et al. WO 2010/066740 A1 and Schneider et al *Fold Des* 1998, 3:R29-R40; such criteria essentially relate to the presence or absence of structural symmetry in the packing of core residues for coiled coils and helix bundles, respectively. Also the presence or absence of left-handed supercoiling for coiled coils and helix bundles, respectively, provides a useful criterion to distinguish between both types of folding.

While aforegoing criteria in principle apply to 2-stranded, 3-stranded, 4-stranded and even more-stranded coiled coils, the Alphabody structure as envisaged herein is restricted to 3-stranded coiled coils. The coiled coil region in an Alphabody can be organized with all alpha-helices in parallel orientation (corresponding to a 'parallel Alphabody' as described in EP2161278 by Applicant Complix NV) or with one of the three alpha-helices being antiparallel to the two other (corresponding to an 'antiparallel Alphabody' as described in WO 2010/066740 by Applicant Complix NV).

The alpha-helical part of an Alphabody structure (as defined herein) will usually grossly coincide with the heptad repeat sequences although differences can exist near the boundaries. For example, a sequence fragment with a clear heptad motif can be non-helical due to the presence of one or more helix-distorting residues (e.g., glycine or proline). Reversely, part of a linker fragment can be alpha-helical despite the fact that it is located outside a heptad repeat region. Further, any part of one or more alpha-helical heptad repeat sequences is also considered an alpha-helical part of a single-chain Alphabody.

The solvent-oriented region of (the alpha-helices of) an Alphabody structure (as defined herein) is an important Alphabody region. In view of the configuration of the alpha-helices in an Alphabody, wherein the residues at heptad a- and d-positions form the core, the solvent-oriented region is largely formed by b-, c- and f-residues. There are three such regions per single-chain Alphabody, i.e., one in each alpha-helix. Any part of such solvent-oriented region is also considered a solvent-oriented region. For example, a subregion composed of the b-, c- and f-residues from three consecutive heptads in an Alphabody alpha-helix will also form a solvent-oriented surface region.

Residues implicated in the formation of (the surface of) a groove between two adjacent alpha-helices in an Alphabody are generally located at heptad e- and g-positions, but some of the more exposed b- and c-positions as well as some of the largely buried core a- and d-positions may also contribute to a groove surface; such will essentially depend on the size of the amino acid side-chains placed at these positions. If said spatially adjacent alpha-helices run parallel, then one half of the groove is formed by b- and e-residues from a first helix and the second half by c- and g-residues of the second helix. If the said spatially adjacent alpha-helices are antiparallel, then there exist two possibilities. In a first possibility, both halves of the groove are formed by b- and e-residues. In the second possibility, both halves of the groove are formed by c- and g-residues. The three types of possible grooves are herein denoted by their primary groove-forming (e- and g-) residues: if the helices are parallel, then the groove is referred to as an e/g-groove; if the helices are antiparallel, then the groove is referred to as either an e/e-groove or a g/g-groove. Parallel Alphabodies have three e/g-grooves, whereas antiparallel Alphabodies have one e/g-groove, one e/e-groove and one g/g-groove. Any part of an Alphabody groove is also considered a groove region.

Also envisaged herein are (Alphabody) polypeptides that comprise or essentially consist of at least one Alphabody as defined herein and optionally comprise one or more further groups, moieties, residues optionally linked via one or more linkers. In these embodiments, the terms "essentially consisting of" or "consisting essentially of" thus refer to the fact that within the polypeptides, the Alphabody is present as the major component, i.e. while the polypeptide may contain additional groups, moieties, residues, these are significantly smaller in size than the Alphabody component in the polypeptide.

Accordingly, a polypeptide as envisaged herein may optionally contain one or more further groups, moieties or residues for binding to other targets or target proteins of interest. It should be clear that such further groups, residues, moieties and/or binding sites may or may not provide further functionality to the Alphabodies as envisaged herein (and/or to the polypeptide or composition in which it is present) and may or may not modify the properties of the Alphabody (Alphabodies) comprised therein. Such groups, residues, moieties or binding units may also for example be chemical groups which can be biologically and/or pharmacologically active.

These groups, moieties or residues are, in particular embodiments, linked N- or C-terminally to the Alphabody structure. In particular embodiments however, one or more groups, moieties or residues are linked to the body of the Alphabody structure, e.g. to a free cysteine in an alphahelix.

In particular embodiments, the polypeptides as envisaged herein comprise one or more Alphabodies that have been chemically modified. For example, such a modification may involve the introduction or linkage of one or more functional groups, residues or moieties into or onto the Alphabody structure. These groups, residues or moieties may confer one or more desired properties or functionalities to the polypeptide. Examples of such functional groups will be clear to the skilled person.

For example, the introduction or linkage of such functional groups to an Alphabody structure can result in an increase in the half-life, the solubility and/or the stability of the polypeptide or in a reduction of the toxicity of the polypeptide, or in the elimination or attenuation of any undesirable side effects of the polypeptide, and/or in other advantageous properties.

In particular embodiments, the polypeptides as envisaged herein comprise Alphabodies that have been chemically modified to increase the biological or plasma half-life thereof, for example, by means of PEGylation, by means of the addition of a group which binds to or which is a serum protein (such as serum albumin or transferrin) or, in general, by linkage of the Alphabody to a moiety that increases the half-life of the polypeptide. As an example, Alphabodies can be PEGylated at a solvent exposed Cysteine using maleimide mPEG 40 kD PEG (Jenkem Technology)) or other PEG moieties of different molecular mass.

In particular embodiments, the polypeptides as envisaged herein comprise Alphabodies that have been fused to protein domains or peptides to increase the biological or plasma half-life thereof, for example, with a domain which binds to or which is a serum protein (such as serum albumin or to the Fc part of an immunoglobulin). Said protein domain may be an Alphabody which binds to a serum protein, such as for example serum albumin or transferrin.

In particular embodiments, the polypeptides as envisaged herein comprise Alphabodies that in addition to their target binding (toward the intracellular target, such as for example anti-apoptotic member of the BCL-2 family of proteins of interest) bind also a serum protein (such as serum albumin or transferrin or to the Fc part of an immunoglobulin) to increase the biological or plasma half-life of said Alphabodies.

Typically, the polypeptides as envisaged herein with increased half-life have a half-life (in human or in an animal model used for PK evaluation such as rat, dog, monkey, mouse, horse, pig, cat, etc) of more than 1 week, equally preferably more than 2 weeks as compared to the half-life of the corresponding Alphabody lacking the above described equipment for half life extension.

A particular modification of the Alphabodies present in the polypeptides envisaged herein may comprise the introduction of one or more detectable labels or other signal-generating groups or moieties, depending on the intended use of the labeled polypeptide.

Yet a further particular modification may involve the introduction of a chelating group, for example to chelate one or more metals or metallic cations.

A particular modification may comprise the introduction of a functional group that is one part of a specific binding pair, such as the biotin-(strept)avidin binding pair.

For some applications, in particular for those applications in which it is intended to kill a cell that expresses the target against which the polypeptides as envisaged herein specifically bind to (e.g., in the treatment of cancer), or to reduce or slow the growth and/or proliferation of such a cell, the polypeptides as envisaged herein may comprise an Alphabody structure linked to a toxin or to a toxic residue or moiety.

Other potential chemical and enzymatic modifications will be clear to the skilled person.

In particular embodiments, the one or more groups, residues, moieties are linked to an Alphabody structure via one or more suitable linkers or spacers.

In further particular embodiments, the polypeptides as envisaged herein comprise two or more target-specific Alphabodies. In such particular embodiments, the two or more target-specific Alphabodies may be linked (coupled, concatenated, interconnected, fused) to each other either in a direct or in an indirect way. In embodiments wherein the two or more Alphabodies are directly linked to each other, they are linked without the aid of a spacer or linker fragment or moiety. Alternatively, in embodiments wherein the two or more Alphabodies are indirectly linked to each other, they are linked via a suitable spacer or linker fragment or linker moiety.

In embodiments wherein two or more Alphabodies are directly linked, they may be produced as single-chain fusion constructs (i.e., as single-chain protein constructs wherein two or more Alphabody sequences directly follow each other in a single, contiguous amino acid sequence). Alternatively, direct linkage of Alphabodies may also be accomplished via cysteines forming a disulfide bridge between two Alphabodies (i.e., under suitable conditions, such as oxidizing conditions, two Alphabodies comprising each a free cysteine may react with each other to form a dimer wherein the constituting momomers are covalently linked through a disulfide bridge).

Alternatively, in embodiments wherein two or more Alphabodies are indirectly linked, they may be linked to each other via a suitable spacer or linker fragment or linker moiety. In such embodiments, they may also be produced as single-chain fusion constructs (i.e., as single-chain protein constructs wherein two or more Alphabody sequences follow each other in a single, contiguous amino acid sequence, but wherein the Alphabodies remain separated by the presence of a suitably chosen amino acid sequence fragment acting as a spacer fragment). Alternatively, indirect linkage of Alphabodies may also be accomplished via amino acid side groups or via the Alphabody N- or C-termini. For example, under suitably chosen conditions, two Alphabodies comprising each a free cysteine may react with a homo-bifunctional chemical compound, yielding an Alphabody dimer wherein the constituting Alphabodies are covalently cross-linked through the said homo-bifunctional compound. Analogously, one or more Alphabodies may be cross-linked through any combination of reactive side groups or termini and suitably chosen homo- or heterobifunctional chemical compounds for cross-linking of proteins.

In particular embodiments of polypeptides comprising linked Alphabodies, the two or more linked Alphabodies can have the same amino acid sequence or different amino acid sequences. The two or more linked Alphabodies can also have the same binding specificity or a different binding specificity. The two or more linked Alphabodies can also have the same binding affinity or a different binding affinity.

Suitable spacers or linkers for use in the coupling of different Alphabodies in a polypeptide as envisaged herein will be clear to the skilled person and may generally be any linker or spacer used in the art to link peptides and/or proteins. In particular, such a linker or spacer is suitable for constructing proteins or polypeptides that are intended for pharmaceutical use.

Some particularly suitable linkers or spacers for coupling of Alphabodies in a single-chain amino acid sequence include for example, but are not limited to, polypeptide linkers such as glycine linkers, serine linkers, mixed glycine/serine linkers, glycine- and serine-rich linkers or linkers composed of largely polar polypeptide fragments. Some particularly suitable linkers or spacers for coupling of Alphabodies by chemical cross-linking include for example, but are not limited to, homo-bifunctional chemical cross-linking compounds such as glutaraldehyde, imidoesters such as dimethyl adipimidate (DMA), dimethyl suberimidate (DMS) and dimethyl pimelimidate (DMP) or N-hydroxysuccinimide (NHS) esters such as dithiobis(succinimidyl-propionate) (DSP) and dithiobis(sulfosuccinimidylpropionate) (DTSSP). Examples of hetero-bifunctional reagents for cross-linking include, but are not limited to, cross-linkers with one amine-reactive end and a sulfhydryl-reactive moiety at the other end, or with a NHS ester at one end and an SH-reactive group (e.g., a maleimide or pyridyl disulfide) at the other end.

A polypeptide linker or spacer for usage in single-chain concatenated Alphabody constructs may be any suitable (e.g., glycine-rich) amino acid sequence having a length between 1 and 50 amino acids, such as between 1 and 30, and in particular between 1 and 10 amino acid residues. It should be clear that the length, the degree of flexibility and/or other properties of the spacer(s) may have some influence on the properties of the final polypeptideas envisaged herein, including but not limited to the affinity, specificity or avidity for a protein of interest, or for one or more other target proteins of interest. It should be clear that when two or more spacers are used in the polypeptides as envisaged herein, these spacers may be the same or different. In the context of the present disclosure, the person skilled in the art will be able to determine the optimal spacers for the purpose of coupling Alphabodies in the polypeptides envisaged herein without any undue experimental burden.

The linked Alphabody polypeptides as envisaged herein can generally be prepared by a method which comprises at least one step of suitably linking one or more Alphabodies to the one or more further groups, residues, moieties and/or other Alphabodies, optionally via the one or more suitable linkers, so as to provide a polypeptide as envisaged herein.

Also, the polypeptides as envisaged herein can be produced by methods at least comprising the steps of: (i) expressing, in a suitable host cell or expression system, the polypeptide as envisaged herein, and (ii) isolating and/or purifying the polypeptide as envisaged herein. Techniques for performing the above steps are known to the person skilled in the art.

[Parts/Fragments/Analogs/Derivatives]

Also envisaged herein are parts, fragments, analogs, mutants, variants, and/or derivatives of the polypeptides as disclosed herein and/or polypeptides comprising one or more parts, fragments, analogs, mutants, variants, and/or derivatives of an Alphabody, as long as these parts, fragments, analogs, mutants, variants, and/or derivatives are suitable for the prophylactic, therapeutic and/or diagnostic purposes envisaged herein.

Such parts, fragments, analogs, mutants, variants, and/or derivatives as envisaged herein are still capable of crossing the cell membrane, and in particular embodiments, specifically binding to an intracellular target, such as for example an anti-apoptotic member of the BCL-2 family of proteins of interest.

[Origin and Form of Alphabodies, Polypeptides and Compositions as Envisaged Herein]

It should be noted that the origin of the Alphabodies, polypeptides or compositions as envisaged herein (or of the nucleotide sequences envisaged herein) used to express them) are not critical to the principles disclosed herein. Furthermore, there is no specific requirement as to the way that the Alphabodies, polypeptides or nucleotide sequences as envisaged herein have been generated or obtained. Thus, the Alphabodies envisaged herein may be synthetic or semi-synthetic amino acid sequences, polypeptides or proteins.

The Alphabodies, polypeptides and compositions provided herein can be in essentially isolated form (as defined herein), or alternatively can form part of a polypeptide or composition as envisaged herein, which may comprise at least one Alphabody and which may optionally further comprise one or more other groups, moieties or residues (all optionally linked via one or more suitable linkers).

[Target Species and Cross-Reactivity]

It will be appreciated based on the disclosure herein that for prophylactic, therapeutic and/or diagnostic applications, the polypeptides and compositions as envisaged herein will in principle be directed against or specifically bind to a human intracellular target. However, where the polypeptides and compositions are intended for veterinary purposes, they may be directed against or specifically bind to an intracellular target from the species intended to be treated, or they will be at least cross-reactive with an intracellular target from the species to be treated. Accordingly, polypeptides and compositions that specifically bind to an intracellular target from one subject species may or may not show cross-reactivity with an intracellular target from one or more other subject species. Of course it is envisaged that, in the context of the development of polypeptides for use in humans or animals, polypeptides may be developed which bind to an intracellular target from another species than that which is to be treated for use in research and laboratory testing.

It is also expected that the polypeptides as envisaged herein will bind to a number of naturally occurring or synthetic analogs, variants, mutants, alleles, parts and fragments of intracellular targets. More particularly, it is expected that the polypeptides as envisaged herein will bind to at least to those analogs, variants, mutants, alleles, parts and fragments of intracellular targets that (still) contain the binding site, part or domain of the (natural/wild-type) intracellular target to which those Alphabodies and polypeptides bind.

[Nucleic Acid Sequences]

Also provided herein are nucleic acid sequences encoding Alphabody polypeptides comprising one or more single chain Alphabody structures, which are capable of entering into a cell, as well as vectors and host cells comprising such nucleic acid sequences.

Thus, nucleic acid sequences encoding the polypeptides as envisaged herein (or suitable fragments thereof) are also provided. These nucleic acid sequences are also referred to herein as nucleic acid sequences as envisaged herein and can also be in the form of a vector or a genetic construct or polynucleotide. The nucleic acid sequences may be synthetic or semi-synthetic sequences, nucleotide sequences that have been isolated from a library (and in particular, an expression library), nucleotide sequences that have been prepared by PCR using overlapping primers, or nucleotide sequences that have been prepared using techniques for DNA synthesis known per se.

The genetic constructs may be DNA or RNA, and are preferably double-stranded DNA. The genetic constructs as envisaged herein may also be in a form suitable for transformation of the intended host cell or host organism in a form suitable for integration into the genomic DNA of the intended host cell or in a form suitable for independent replication, maintenance and/or inheritance in the intended host organism. For instance, the genetic constructs may be in the form of a vector, such as for example a plasmid, cosmid, YAC, a viral vector or transposon. In particular, the vector may be an expression vector, i.e., a vector that can provide for expression in vitro and/or in vivo (e.g. in a suitable host cell, host organism and/or expression system). The genetic constructs as envisaged herein may comprise a suitable leader sequence to direct the expressed Alphabody to an intended intracellular or extracellular compartment.

For example, the genetic constructs as envisaged herein may be inserted in a suitable vector at a pelB leader sequence site to direct the expressed Alphabody to the bacterial periplasmic space. Also the vector may be equipped with a suitable promoter system to, for example, optimize the yield of the Alphabody. Thus, also provided herein are vectors comprising nucleic acids encoding single-chain Alphabodies or polypeptides comprising said single-chain Alphabodies.

Also provided herein are host cells comprising nucleic acids encoding polypeptides comprising said single-chain Alphabodies, which are capable of entering a cell or vectors comprising these nucleic acids. Accordingly, in particular embodiments host cells are provided transfected or transformed with a vector comprising the nucleic acid sequences encoding the polypeptides envisaged herein and capable of expressing the polypeptides envisaged herein. Suitable examples of hosts or host cells for expression of the polypeptides as envisaged herein will be clear to the skilled person and include any suitable eukaryotic or prokaryotic cell (e.g., bacterial cells such as *E. coli*, yeast cells, mammalian cells, avian cells, amphibian cells, plant cells, fish cells, and insect cells), whether located in vitro or in vivo.

[Inhibiting Alphabodies, Polypeptides and Compositions]

In particular embodiments, the polypeptides as envisaged herein that specifically bind to an intracellular target molecule of interest are capable of specifically inhibiting, preventing or decreasing the activity of an intracellular target molecule of interest and/or of inhibiting, preventing or decreasing the signaling and biological mechanisms and pathways in which these intracellular target molecules play a role.

By binding to one or more particular intracellular targets, the polypeptides and pharmaceutical compositions as envisaged herein can be used to prevent or inhibit the interaction between one or more intracellular targets, thereby preventing, inhibiting or reducing the signaling pathways that are mediated by those intracellular targets and/or modulating the biological pathways and mechanisms in which those intracellular targets are involved. Accordingly, the polypeptides and pharmaceutical compositions as envisaged herein can be used to affect, change or modulate the immune system and/or one or more specific immune responses in a subject in which the intracellular target molecule of interest to which the one or more of the polypeptides and compositions as envisaged herein bind, are involved.

Thus, in particular embodiments, the polypeptides and compositions as envisaged herein, specifically bind to an anti-apoptotic member of the BCL-2 family of proteins.

More particularly, 'inhibiting', 'reducing' and/or 'preventing' using a polypeptide or composition as envisaged herein may mean either inhibiting, reducing and/or preventing the interaction between a target protein of interest and its natural binding partner, or, inhibiting, reducing and/or preventing the activity of a target protein of interest, or, inhibiting, reducing and/or preventing one or more biological or physiological mechanisms, effects, responses, functions pathways or activities in which the target protein of interest is involved, such as by at least 10%, but preferably at least 20%, for example by at least 50%, at least 60%, at least 70%, at least 80%, at least 90%, at least 95% or more, as measured using a suitable in vitro, cellular or in vivo assay, compared to the activity of the target protein of interest in the same assay under the same conditions but without using the polypeptide or composition as envisaged herein. In addition, 'inhibiting', 'reducing' and/or 'preventing' may also mean inducing a decrease in affinity, avidity, specificity and/or selectivity of a target protein of interest for one or more of its natural binding partners and/or inducing a decrease in the sensitivity of the target protein of interest for one or more conditions in the medium or surroundings in which the target protein of interest is present (such as pH, ion strength, the presence of co-factors, etc.), compared to the same conditions but without the presence of the polypeptide or composition as envisaged herein. In the context of the present disclosure, 'inhibiting', 'reducing' and/or 'preventing' may also involve allosteric inhibition, reduction and/or prevention of the activity of a target protein of interest.

The result of the binding of the polypeptides as envisaged hereinto an intracellular target molecule of interest can be such that, upon binding to that target, it prevents, reduces or inhibits binding of that target to its naturally occurring binding partner or to at least one subunit thereof compared to the binding of the target to its naturally occurring binding partner in the absence of such polypeptides or pharmaceutical compositions as envisaged herein, and this by at least 20%, for example by at least 50%, as at least 70%, at least 80%, at least 90%, at least 95% or more, as determined by a suitable assay known in the art. Alternatively, the binding of the polypeptide to the intracellular target molecule is such that it still allows this target molecule to bind to its naturally occurring binding partner, but prevents, reduces or inhibits the signalling that would be triggered by binding of the intracellular target molecule of interest to its binding partner or at least one subunit thereof compared to the signalling upon binding of the intracellular target to its natural binding partner in the absence of such polypeptides or pharmaceutical compositions as envisaged herein, and this by at least 20%, for example by at least 50%, as at least 70%, at least 80%, at least 90%, at least 95% or more, as determined by a suitable assay known in the art.

As will be known to the skilled person, the above polypeptides and compositions comprising polypeptides as envisaged herein will generally act as antagonists of intracellular target mediated signalling, i.e. the signalling that is caused by binding of an intracellular target molecule of interest to its natural binding partner, as well as the biological mechanisms and effects that are induced by such signalling.

[Agonizing Alphabodies, Polypeptides and Compositions]

In certain non-limiting embodiments, a polypeptide or composition as envisaged herein may specifically bind to an intracellular target molecule of interest thereby enhancing, increasing and/or activating the interaction between that intracellular target and/or its natural binding partner. Such an agonizing polypeptide envisaged herein may specifically bind to an intracellular target molecule of interest thereby enhancing, increasing and/or activating the biological activity and/or one or more biological or physiological mechanisms, effects, responses, functions or pathways of that intracellular target and/or its natural binding partner, as measured using a suitable in vitro, cellular or in vivo assay. As will be clear to the skilled person, the polypeptides and compositions according to this particular embodiment, will generally act as agonists of intracellular target mediated signalling, i.e. the signalling that is caused by binding of an intracellular target molecule of interest to its natural binding partner, as well as the biological mechanisms and effects that are induced by such signalling.

Accordingly, in these particular embodiments, the polypeptides and pharmaceutical compositions as envisaged herein can be used to increase one or more specific immune responses in a subject in which the an intracellular target molecule of interest to which the one or more of the polypeptides and compositions as disclosed herein bind, are involved. Agonistic polypeptides or pharmaceutical compositions as envisaged herein binding to certain intracellular target molecules can be used to stimulate or enhance one or more immune responses in a subject, for example for the prevention and/or treatment of diseases that are characterized by a weakened immune system or that may occur as a result of having a weakened immune system.

Also provided herein are methods for the production of a polypeptides comprising at least one Alphabody having detectable binding affinity for, or inhibitory activity on, one or more intracellular target proteins. Such methods will be clear to the skilled person based on the further description herein.

Thus also provided herein are different applications of the polypeptides as described herein. In particular, the polypeptides as provided herein can be used for modulating the biological function of an intracellular protein in vitro, such as for instance for affecting and, in particular inhibiting, the interaction between the intracellular protein and natural binding partner.

[Methods for the Production of Polypeptides]

The polypeptides envisaged herein have the ability to enter into a cell. The methods for producing such a polypeptide at least comprise the step of introducing an internalization region into at least part of a sequence of at least one Alphabody structure.

Introducing an internalization region into at least part of a sequence of at least one Alphabody structure may for example comprise the introduction of specific mutations into a chosen Alphabody structure sequence template. Indeed, a certain Alphabody sequence template that is designed may be used to create modifications, i.e. replacement mutations or substitutions of non-charged or negatively charged amino acid residues into positively charged amino acid residues. In this way, the Alphabody template sequence may be "decorated" or tailored to comprise an internalization region. Alternatively it is envisaged that the methods involve the designing of one or more internalization regions at least partly into an Alphabody scaffold structure.

Accordingly, in particular embodiments, the Alphabody structure as comprised in the polypeptides envisaged herein may be modified or be designed to comprise an internalization region by substituting within a fragment of maximally 16 amino acid residues at least six non-positively charged amino acid residues by at least six positively charged amino acid residues, or by designing within a stretch of maximally 16 amino acid residues at least six positively charged amino acid residues. In further specific embodiments, the Alphabody template sequence as comprised in the polypeptides envisaged herein may be modified or designed to comprise within a stretch of maximally 16 amino acid residues at least six positively charged amino acid residues, of which at least 4 residues are arginines, or of which at least 5 residues are lysines.

In certain particular embodiments, the Alphabody structure as comprised in the polypeptides envisaged herein may be modified or be designed to comprise an internalization region by substituting within a fragment a number of residues so as to obtain at least one positively charged internalization region, which consists for at least 35% of positively charged amino acids and contains at least six non-positively charged amino acid residues.

Thus, in particular embodiments of the methods as described herein, polypeptides may be synthesized such that they contain at least one internalization region, i.e. by in silico design and synthesis of an Alphabody structure sequence. In particular embodiments, the polypeptides comprise an internalization region of maximally 16 amino acid residues comprising at least six positively charged amino acid residues. In further particular embodiments, the polypeptides as envisaged herein may be designed to comprise an internalization region comprising a fragment of maximally 16 amino acid residues comprising at least 6 positively charged amino acid residues of which (i) at least 4 residues are arginines, or (ii) at least 5 residues are lysines. In other particular embodiments, the polypeptides comprise an internalization region which consists for at least 35% of positively charged amino acids and contains at least six non-positively charged amino acid residues. In further particular embodiments, the polypeptides as envisaged herein may be designed to comprise an internalization region comprising for at least 35% of positively charged amino acids and contains at least six non-positively charged amino acid residues of which (i) at least 4 residues are arginines, or (ii) at least 5 residues are lysines. In the methods envisaged herein above, the internalization region is provided at least in part in the Alphabody structure, i.e. is integrated at least in part in the backbone typical of the Alphabody template. More particularly, it is envisaged that the at least one internalization region is provided for at least 80% (i.e. 80% of the amino acid residues comprised in one internalization region) within one Alphabody structure sequence. More particularly, embodiments are envisaged whereby 90% or up to 100% of the amino acids of the internalization region of the polypeptide are integrated into an Alphabody structure. Moreover, in particular embodiments it is envisaged that one or more or each of the internalization regions is provided within one alpha-helix of an Alphabody structure in the polypeptide. In particular embodiments, only one internalization region is provided within one alpha-helix of an Alphabody structure of the polypeptide. In particular embodiments, polypeptides are envisaged wherein an internalization region is provided in two alpha-helices of an Alphabody structure. It is preferred that internalization regions are not provided in all three of the alpha-helices of an Alphabody structure.

In certain specific embodiments, the polypeptides envisaged herein combine a binding affinity for an intracellular target with the ability to enter into a cell. It will be clear to the skilled person, that different methods are envisaged for producing the polypeptides described herein, which methods either start from the target specificity or from the internalization properties of the polypeptides.

Thus, in particular embodiments, methods are provided which encompass identifying a target binding Alphabody sequence and which thereafter involve modifying said structure (either by addition of amino acids or actual modification of the Alphabody sequence) to ensure internalization of the resulting Alphabody polypeptide.

Indeed, in particular embodiments, the methods envisaged herein may comprise, prior to the step of introducing said internalization region, the step of selecting at least one Alphabody structure for its specific binding affinity to an intracellular target molecule of interest.

Methods for obtaining suitable Alphabodies having a binding affinity for a given target are known to the skilled person and are moreover described herein below. The application further describes different methods for obtaining polypeptides therefrom which are capable of internalization into the cell.

In alternative embodiments, it can be envisaged that one starts from a polypeptide scaffold which is capable of being internalized in the cell and which is then modified or screened for target-binding properties.

Indeed, in particular embodiments, the methods envisaged herein, further comprise subsequent to the step of introducing an internalization region, the step of selecting at least one Alphabody structure for its specific binding affinity to an intracellular target molecule of interest.

In these embodiments, the step of selecting at least one Alphabody structure for its specific binding affinity to an intracellular target molecule of interest, involves at least the step of screening a library of Alphabody structure sequences for specific binding to said intracellular target molecule.

In particular embodiments of these methods, libraries of polypeptides are provided which are characterized by the presence of at least one Alphabody structure and further by one or more internalization regions, whereby the amino acids of the target binding domains of the Alphabody are variegated. In these embodiments, the library can be screened for binding to the intracellular target of interest to obtain a polypeptide capable of binding to the intracellular target.

In further embodiments it can be envisaged that a suitable polypeptide scaffold, having cell penetrating capability is modified to introduce, e.g. based on mimicry, a suitable binding motif. In these embodiments, the step of selecting at least one Alphabody structure for its specific binding affinity to an intracellular target molecule of interest, involves at least the step of introducing a binding motif in said at least one Alphabody structure sequence to said intracellular target molecule and testing the specific binding affinity to said intracellular target molecule of interest.

The most suitable method for obtaining the target specific polypeptides as envisaged herein will depend on the target. Indeed, where the binding motif for a given target is known, introduction of target binding and cell-penetrating features can be introduced into the polypeptide simultaneously. However, for targets where binding motifs are not yet known, it can be envisaged to include a screening step of libraries of Alphabodies or polypeptides having variegated amino acids at those positions suitable for binding to a target.

[Methods for the Production of Target-Binding Alphabodies]

[Methods for the Production of Alphabodies by Means of Libraries]

In particular embodiments envisaged herein, the target-specific Alphabody polypeptides can be obtained by methods which involve generating a random library of Alphabodies and screening this library for an Alphabody polypeptide capable of specifically binding to a target of interest, and in particular to an intracellular target molecule of interest. These methods are described in detail in published international patent application No. WO 2012/092970 in the name of Complix NV.

It will be understood that the selection step of the methods described in WO2012/092970 can be performed by way of a method commonly known as a selection method or a by way of a method commonly known as a screening method. Both methods envisage the identification and subsequent isolation (i.e., the selection step) of desirable components (i.e. Alphabody library members) from an original ensemble comprising both desirable and non-desirable components (i.e. an Alphabody library). In the case of a selection method, library members will typically be isolated by a step wherein the desired property is applied to obtain the desired goal; in such case, the desired property is usually restricted to the property of a high affinity for a given intracellular target molecule of interest and the desired goal is usually restricted to the isolation of such high-affinity library members from the others. Such method is generally known as an affinity selection method and, in the context of the present disclosure, such affinity selection method will be applied to a single-chain Alphabody library for the purpose of selecting Alphabodies having a high affinity for an intracellular target molecule of interest or a subdomain or subregion thereof. Equally possible is to select for kinetic properties such as e.g. high on-rate for binding to a given an intracellular target molecule of interest, or low off-rate for library members bound to said target by adjusting the appropriate selection conditions (e.g. short incubation times or long wash cycles, or other conditions as is known by someone skilled in the art of library selection techniques). Alternatively, in the case of a screening method, library members will typically be isolated by a step wherein all library members, or at least a substantial collection of library members, are individually examined with respect to a given desired property, and wherein members having such desired property are retained whereas members not having such desired property are discarded; in such case, and in the context of the present disclosure, desired properties may relate to either a high affinity for an intracellular target molecule of interest or a subdomain or subregion thereof, or a functional activity such as an anti-intracellular target molecule activity, including the inhibition, reduction and/or prevention of the activity of an intracellular target molecule of interest. The selection step of the methods for producing polypeptides as envisaged herein thus may be accomplished by either an (affinity) selection technique or by an affinity-based or activity-based functional screening technique, both techniques resulting in the selection of one or more polypeptides comprising at least one single-chain Alphabody having beneficial (favorable, desirable, superior) affinity or activity properties compared to the non-selected polypeptides of the library.

Specific binding of an Alphabody or polypeptide to a target molecule or protein of interest can be determined in any suitable manner known per se, including, for example biopanning, Scatchard analysis and/or competitive binding assays, such as radioimmunoassays (RIA), enzyme immunoassays (EIA) and sandwich competition assays, and the different variants thereof known in the art.

Thus, in particular embodiments, the Alphabody or polypeptide libraries envisaged herein are provided as a phage library and binding Alphabodies or polypeptides are identified by contacting the phage with the labeled target molecule, after which binding phages are retrieved by detection or selective collection of the labeled, bound target. Typically, a biotinylated target can be used, whereby phage which generate an Alphabody binding to the target are captured with a streptavidin-coated support (e.g. magnetic beads).

In particular embodiments, the selection steps of the methods for producing one or more polypeptides having detectable binding affinity (as defined herein) for a protein of interest, may comprise the (further) enrichment of the Alphabody or polypeptide library or the mixture of Alphabody or polypeptides libraries for Alphabodies or polypeptides having detectable binding affinity for the protein of interest by iterative execution of the steps of contacting a protein of interest with a single-chain Alphabody or polypeptide library or with a mixture of single-chain Alphabody or polypeptide libraries and subsequently identifying from the single-chain Alphabody or polypeptide library or mixture of single-chain Alphabody or polypeptide libraries being contacted with the protein, the one or more single-chain Alphabodies or polypeptides having detectable binding affinity for the protein of interest.

The steps of selecting a single-chain Alphabody (or polypeptide) that has detectable in vitro activity by interacting with a target protein of interest typically comprise:
a) contacting a library of single-chain Alphabodies (or polypeptides comprising said alphabodies) or a mixture of single-chain Alphabody libraries with the an intracellular target molecule of interest, or a fragment thereof and
b) identifying from the library or mixture of libraries, the one or more single-chain Alphabodies or polypeptides having detectable in vitro activity on the intracellular target molecule of interest.

More particularly, an intracellular target molecule may be a membrane anchored receptor, a soluble receptor or a molecule comprising one or more ectodomains of said intracellular target molecule.

More particularly, the effect on the activity of an intracellular target molecule or on the activity of an intracellular target molecule can be measured by ways known in the art. More specifically this involves determining the effect of the Alphabody or polypeptide on a known intracellular target-mediated effect in vitro.

It will be understood that the selection methods described herein can also be performed as screening methods. Accordingly the term 'selection' as used in the present description can comprise selection, screening or any suitable combination of selection and/or screening techniques.

[Isolation]

In some cases, the methods for producing the Alphabody polypeptides binding specifically to an intracellular target protein of interest as envisaged herein may further comprise the step of isolating from the single-chain Alphabody or polypeptide library at least one single-chain Alphabody or polypeptide having detectable binding affinity for, or detectable in vitro activity on, an intracellular target molecule of interest.

These methods may further comprise the step of amplifying at least one single-chain Alphabody (polypeptide) having detectable binding affinity for, or detectable in vitro activity on, an intracellular target molecule of interest. For example, a phage clone displaying a particular single-chain Alphabody or polypeptide, obtained from a selection step as envisaged herein, may be amplified by re-infection of a host bacteria and incubation in a growth medium.

In particular embodiments, these methods may encompass determining the sequence of the one or more Alphabodies or polypeptides capable of binding to an intracellular target molecule.

Where an Alphabody polypeptide sequence, comprised in a set, collection or library of Alphabody polypeptide sequences, is displayed on a suitable cell or phage or particle, it is possible to isolate from said cell or phage or particle, the nucleotide sequence that encodes that Alphabody polypeptide sequence. In this way, the nucleotide sequence of the selected Alphabody library member(s) can be determined by a routine sequencing method.

In further particular embodiments, the methods for producing an Alphabody polypeptide as envisaged herein comprise the step of expressing said nucleotide sequence(s) in a host organism under suitable conditions, so as to obtain the actual desired Alphabody polypeptide sequence(s). This step can be performed by methods known to the person skilled in the art.

In addition, the obtained Alphabody or polypeptide sequences having detectable binding affinity for, or detectable in vitro activity on, an intracellular target molecule of interest, may be synthesized as soluble protein construct, optionally after their sequence has been identified.

For instance, the Alphabodies or polypeptides obtained, obtainable or selected by the above methods can be synthesized using recombinant or chemical synthesis methods known in the art. Also, the Alphabodies or polypeptides obtained, obtainable or selected by the above methods can be produced by genetic engineering techniques. Thus, methods for synthesizing the Alphabodies or polypeptides obtained, obtainable or selected by the above methods may comprise transforming or infecting a host cell with a nucleic acid or a vector encoding an Alphabody or polypeptide sequence having detectable binding affinity for, or detectable in vitro activity on, an intracellular target molecule of interest. Accordingly, the Alphabody or polypeptide sequences having detectable binding affinity for, or detectable in vitro activity on, an intracellular target molecule of interest can be made by recombinant DNA methods. DNA encoding the Alphabodies or polypeptides can be readily synthesized using conventional procedures. Once prepared, the DNA can be introduced into expression vectors, which can then be transformed or transfected into host cells such as E. coli or any suitable expression system, in order to obtain the expression of Alphabodies or polypeptides in the recombinant host cells and/or in the medium in which these recombinant host cells reside.

It should be understood, as known by someone skilled in the art of protein expression and purification, that the Alphabody or polypeptide produced from an expression vector using a suitable expression system may be tagged (typically at the N-terminal or C-terminal end of the Alphabody) with e.g. a Histidine or other sequence tag for easy purification.

Transformation or transfection of nucleic acids or vectors into host cells may be accomplished by a variety of means known to the person skilled in the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

Suitable host cells for the expression of the desired Alphabodies or polypeptides may be any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

Thus, the methods for the production of polypeptides having detectable binding affinity for, or detectable in vitro activity on, an intracellular target molecule of interest are also provided, comprising transforming, transfecting or infecting a host cell with nucleic acid sequences or vectors encoding such polypeptides and expressing the polypeptides under suitable conditions.

[Sequence Rationalization and Dedicated Library Screening]

The methods for the production of one or more target-specific polypeptides may optionally comprise further steps or methods for improving or optimizing the binding specificity and/or efficacy of the target-specific polypeptides.

In particular embodiments, the methods for the production of one or more target-binding polypeptides, may further be followed by steps or methods involving the rationalization of the obtained or produced Alphabody polypeptide sequences. Such a sequence rationalization process may include the identification or determination of particular amino acid residues, amino acid residue positions, stretches, motifs or patterns that are conserved between or among different Alphabodies or polypeptides against a specific target molecule of interest that can be produced using the methods disclosed herein. Accordingly, this rationalization process can be conducted by comparing different produced Alphabody or polypeptide sequences that are specific for a certain target molecule or protein of interest and identifying the sequence coherence between these sequences. Such a process can be optionally supported or performed by using techniques for molecular modeling, interactive ligand docking or biostatistical data mining.

The particular amino acid residues, amino acid residue positions, stretches, motifs or patterns that are identified as being conserved between or among different Alphabody structures against a specific target molecule of interest may be considered as contributing to the binding or activity of the target-specific Alphabodies.

In particular embodiments, the process of sequence rationalization as described above may further be followed by the creation of a new library of Alphabody or polypeptide sequences starting from the set of different Alphabody or polypeptide sequences that have been identified as being specific for a target molecule of interest. In such a so-called, 'dedicated library', in the set of different Alphabody or polypeptide sequences that have been identified as being specific for a certain target molecule of interest, the different Alphabody or polypeptide sequences are varied in a defined set of variegated amino acid residue positions. This defined set of variegated amino acid residue positions corresponds to those positions outside the positions where the amino acid residues, stretches, motifs or patterns are located that are conserved between or among different target-binding Alphabodies or polypeptides. The Alphabody or polypeptide libraries so obtained are referred to as 'dedicated libraries' of Alphabodies or polypeptides. These dedicated libraries are then again screened to identify the best target-binding Alphabody.

Thus, in the production of such dedicated libraries of Alphabody or polypeptide sequences, the amino acid residues, stretches, motifs or patterns that are conserved between or among different Alphabodies or polypeptides are kept constant during the production process of the library. From such dedicated libraries, Alphabody or polypeptide sequences having an improved or optimized binding specificity for and/or in vitro activity on the target molecule of interest may be identified and optionally isolated.

In particular embodiments, the process of sequence rationalization as described above may further be followed by the creation of a new library of Alphabody or polypeptide sequences starting from the set of different Alphabody or polypeptide sequences that have been identified as being specific for a target molecule of interest and that can been produced using the methods described herein. In such a so-called, 'spiked library' the set of different Alphabody or polypeptide sequences that have been identified as being specific for a certain target molecule of interest, the different Alphabody or polypeptide sequences are varied by introducing at a limited number of randomly chosen positions, random amino acid substitutions. As is known by a person skilled in the art of library generation, error-prone PCR is a convenient method to generate 'spiked libraries', This can also be conveniently accomplished by a direct DNA synthesis method using spiked oligonucleotides as is known to someone skilled in the art of DNA synthesis.

Accordingly, the methods for the production of one or more target-binding polypeptides, may further, after the identification of two or more target-binding Alphabodies or polypeptides from a random library, comprise the steps of:

comparing the produced Alphabody or polypeptide sequences that bind the target protein of interest, identifying the amino acid residues, amino acid residue positions, stretches, motifs or patterns that are conserved between or among these different Alphabody or polypeptide sequences, and:

starting from at least one of the two or more Alphabody or polypeptide sequences compared, producing a spiked library wherein the library comprises different Alphabody or polypeptide sequences that are variegated at a limited number of randomly chosen positions, or, producing a dedicated library wherein the library comprises different Alphabody or polypeptide sequences that are variegated in a set of amino acid positions which are not the amino acid residues, amino acid residue positions, stretches, motifs or patterns that are conserved between or among the different target-binding Alphabody or polypeptide sequences, selecting and/or identifying from the random library those Alphabody or polypeptide sequences having an improved or optimized binding specificity for and/or in vitro activity on the target molecule of interest, and optionally isolating these Alphabody or polypeptide sequences having an improved or optimized binding specificity for and/or in vitro activity on the target molecule of interest.

It will be understood that the steps involved in the methods for producing a dedicated or a spiked library and selecting, identifying and isolating Alphabody or polypeptide sequences having an improved or optimized binding specificity for and/or in vitro activity on the target molecule of interest, as described above, may be performed in a similar manner as described for the corresponding steps of the methods for producing target-binding Alphabodies or polypeptides.

As further described herein, the total number of amino acid residues in a Alphabody structure present within a polypeptide envisaged herein can be in the range of about 50 to about 210, depending mainly on the number of heptads per heptad repeat sequence and the length of the flexible linkers interconnecting the heptad repeat sequences. Parts, fragments, analogs or derivatives of a polypeptide or composition are not particularly limited as to their length and/or size, as long as such parts, fragments, analogs or derivatives still have the biological function of the polypeptide or composition envisaged herein from which they are derived and can still be used for the envisaged (pharmacological) purposes.

It should be remarked that directed evolution methods (such as DNA shuffling methods) may also be employed in building Alphabody or polypeptide libraries starting from one or more different Alphabody or polypeptide sequences that have been identified as being specific for a target molecule of interest. Such 'directed evolution' libraries can also be subjected to the selection and/or the identification of those Alphabody sequences having an improved or optimized binding specificity for and/or in vitro activity on the target molecule of interest.

[Methods for the Production of Alphabodies Based on Mimicry]

In an alternative embodiment, it is envisaged that for the production of target-specific polypeptides, i.e. having detectable binding affinity for, or inhibitory activity on intracellular target molecules, binding sites can be introduced on an Alphabody structure sequence based on mimicry. It will be understood that the grafting of a specific target-binding site of an Alphabody structure can be performed either before or after the cell penetrating properties have been introduced. Thus, it will be understood that the steps described for the methods herein below can be performed on an Alphabody structure per se or on a polypeptide comprising or consisting of such an Alphabody structure. In particular such methods for the generation of target specific Alphabody structures comprise at least the steps of:

(a) the identification of the Alphabody helix that is to be elected for the mimicry of at least part of the binding site of a ligand that binds to in that target molecule of interest, and (b) the determination of the segment in the particular Alphabody alpha-helix that is used for the mimicry of said binding site of said ligand that binds to that target molecule of interest.

This process is disclosed in detail in published international patent application WO2012/093013 in the name of Complix NV.

[Pharmaceutical Compositions]

Also provided herein are pharmaceutical compositions comprising one or more polypeptides and/or nucleic acid sequences as envisaged herein and optionally at least one pharmaceutically acceptable carrier (also referred to herein as pharmaceutical compositions envisaged herein). According to certain particular embodiments, the pharmaceutical compositions as envisaged herein may further optionally comprise at least one other pharmaceutically active compound.

The pharmaceutical compositions as envisaged herein can be used in the diagnosis, prevention and/or treatment of diseases and disorders associated with intracellular target molecules of interest. In particular, pharmaceutical compositions are envisaged comprising one or more polypeptides as envisaged herein that are suitable for prophylactic, therapeutic and/or diagnostic use in a warm-blooded animal, and in particular in a mammal, and more in particular in a human being.

In particular, pharmaceutical compositions comprising and one or more polypeptides as envisaged herein that can be used for veterinary purposes in the prevention and/or treatment of one or more diseases, disorders or conditions associated with and/or mediated by intracellular target molecules of interest.

Generally, for pharmaceutical use, the polypeptides as envisaged herein may be formulated as a pharmaceutical preparation or compositions comprising at least one Alphabody or polypeptide as envisaged herein and at least one pharmaceutically acceptable carrier, diluent or excipient and/or adjuvant, and optionally one or more further pharmaceutically active polypeptides and/or compounds. Such a formulation may be suitable for oral, parenteral, topical administration or for administration by inhalation. Thus, the Alphabodies, or polypeptides as envisaged herein and/or the compositions comprising the same can for example be administered orally, intraperitoneally, intravenously, subcutaneously, intramuscularly, transdermally, topically, by means of a suppository, by inhalation, again depending on the specific pharmaceutical formulation or composition to be used. The clinician will be able to select a suitable route of administration and a suitable pharmaceutical formulation or composition to be used in such administration.

The pharmaceutical compositions may also contain suitable binders, disintegrating agents, sweetening agents or flavoring agents. Tablets, pills, or capsules may be coated for instance with gelatin, wax or sugar and the like. In addition, the polypeptides envisaged herein may be incorporated into sustained-release preparations and devices.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. Antibacterial and antifungal agents and the like can optionally be added.

Useful dosages of the polypeptides as envisaged herein can be determined by determining their in vitro activity, and/or in vivo activity in animal models. Methods for the extrapolation of effective dosages in mice, and other animals, to humans are known to the skilled person.

The amount of the polypeptides as envisaged herein required for use in prophylaxis and/or treatment may vary not only with the particular Alphabody or polypeptide selected but also with the route of administration, the nature of the condition being treated and the age and condition of the patient and will be ultimately at the discretion of the attendant physician or clinician. Also the dosage of the polypeptides envisaged herein may vary depending on the target cell, tumor, tissue, graft, or organ.

The polypeptides as envisaged herein and/or the compositions comprising the same are administered according to a regimen of treatment that is suitable for preventing and/or treating the disease or disorder to be prevented or treated. The clinician will generally be able to determine a suitable treatment regimen. Generally, the treatment regimen will comprise the administration of one or more polypeptides, or of one or more compositions comprising the same, in one or more pharmaceutically effective amounts or doses.

The desired dose may conveniently be presented in a single dose or as divided doses (which can again be sub-dosed) administered at appropriate intervals. An administration regimen could include long-term (i.e., at least two weeks, and for example several months or years) or daily treatment.

The polypeptides as envisaged herein will be administered in an amount which will be determined by the medical practitioner based inter alia on the severity of the condition and the patient to be treated. Typically, for each disease indication an optical dosage will be determined specifying the amount to be administered per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment.

In particular, the polypeptides as envisaged herein may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

[Prophylactic, Therapeutic and/or Diagnostic Applications]

Also provided herein is use of the polypeptides as envisaged herein for the preparation of a medicament for the prevention and/or treatment of a disease mediated by an intracellular target or a disorder in which an intracellular target molecule is involved.

In particular embodiments, polypeptides are provided can be linked to a molecule capable of targeting an intracellular protein. In further embodiments, polypeptides are provided which themselves specifically bind to an intracellular target. These polypeptides are envisaged for use in the prevention and/or treatment of at least one intracellular target-mediated disease and/or a disorder in which said intracellular target molecule is involved. In particular embodiments, methods for the prevention and/or treatment of an intracellular target-mediated disease and/or disorder are provided, comprising administering to a subject in need thereof, a pharmaceutically active amount of one or more polypeptides and/or pharmaceutical compositions described herein. In particular, the pharmaceutically active amount may be an amount that is sufficient (to create a level of the polypeptide in circulation) to inhibit, prevent or decrease (or in the case of agonistic polypeptides envisaged herein enhance, promote or increase) intracellular targets, or their biological or pharmacological activity and/or the biological pathways or signaling in which they are involved.

The subject or patient to be treated with the polypeptides described herein may be any warm-blooded animal, but is in particular a mammal, and more in particular a human suffering from, or at risk of, diseases and disorders in which an intracellular target molecule is involved.

The efficacy of the polypeptides envisaged herein, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person.

Depending on the intracellular target involved, the skilled person will generally be able to select a suitable in vitro assay, cellular assay or animal model to test the polypeptides envisaged herein for binding to the intracellular target molecule or for their capacity to affect the activity of these intracellular target molecules, and/or the biological mechanisms in which these are involved; as well as for their therapeutic and/or prophylactic effect in respect of one or more diseases and disorders that are associate with an intracellular target molecule.

Accordingly, particular embodiments envisaged herein provide polypeptides comprising at least one Alphabody that is capable of being internalized in a cell and which specifically binds to an intracellular target molecule that is biologically active within the cell for use as a medicament, and more particularly for use in a method for the treatment of a disease or disorder chosen from the group consisting of cancer, infectious diseases, hematopoietic diseases, metabolic diseases, immune diseases, neurological disorders, proliferative disorders, cardiovascular diseases and inflammatory diseases. In particular embodiments, the polypeptides envisaged herein are used to treat, prevent, and/or diagnose cancers and neoplastic conditions. Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

The polypeptides as envisaged herein can also be used to treat a variety of proliferative disorders. Examples of proliferative disorders include hematopoietic neoplastic disorders and cellular proliferative and/or differentiative disorders, such as but not limited to, epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, miscellaneous malignant neoplasms, gynecomastia carcinoma, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma), malignant mesothelioma, non-neoplastic polyps, adenomas, familial syndromes, colorectal carcinogenesis, colorectal carcinoma, carcinoid tumors, nodular hyperplasias, adenomas, and malignant tumors, including primary carcinoma of the liver and metastatic tumors, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors The polypeptides as envisaged herein can also be used to treat a variety of immune disorders, such as but not limited to an inflammatory disease or disorder, or an autoimmune disease or disorder.

The polypeptides as envisaged herein can further be used to treat hematopoietic disorders or diseases including, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

The polypeptides as envisaged herein can also be used to treat cardiovascular disorders (e.g., inflammatory disorders) including, but not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices.

The polypeptides described herein can further be used to treat a human, at risk for or afflicted with a neurological disease or disorder including but not limited to Alzheimer Disease or Parkinson Disease, Huntington disease, dentatorubral pallidoluysian atrophy or a spinocerebellar ataxia, e.g., SCAI, SCA2, SCA3 (Machado-Joseph disease), SCA7 or SCA8, ALS, multiple sclerosis, epilepsy, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, and Bovine Spongiform Encephalitis, a prion-mediated disease.

The following non-limiting Examples and Figures are provided, in which the figures show:

LEGENDS TO THE FIGURES

FIG. 1: Sequence of Alphabody MB23_hiR-V5 (SEQ ID NO: 2). Arginine decoration is shown in bold and N-terminal V5 tag is shown underlined. The sequence is shown as fragments, labeled 'Helix A', 'Loop 1', 'Helix B', 'Loop 2', 'Helix C', 'His-tag' and V5-tag', respectively, to distinguish between different structural elements. The full MB23_hiR-V5 sequence is a single polypeptide sequence consisting of these fragments in the order as shown.

FIG. 2: Intracellular uptake of two-fold dilutions of cationized MB23_hiR-V5 (SEQ ID NO: 2) starting at 312 nM to 1.2 nM in human glioblastoma cells (U87.MG). Alphabody was incubated 2 h in presence of 10% serum with cells at 37° C. After PBS washing, fixing and permeabilizing cells, intracellular Alphabody was visualized with a primary anti-V5 antibody and a secondary goat anti-mouse antibody labeled to Alexa 488. The nucleus was stained with DAPI. Control images (ctrl) correspond to the same experimental conditions without Alphabody. Images correspond to superposed images of slices of 1 µm of the recorded Z-stacks.

Figure 3:
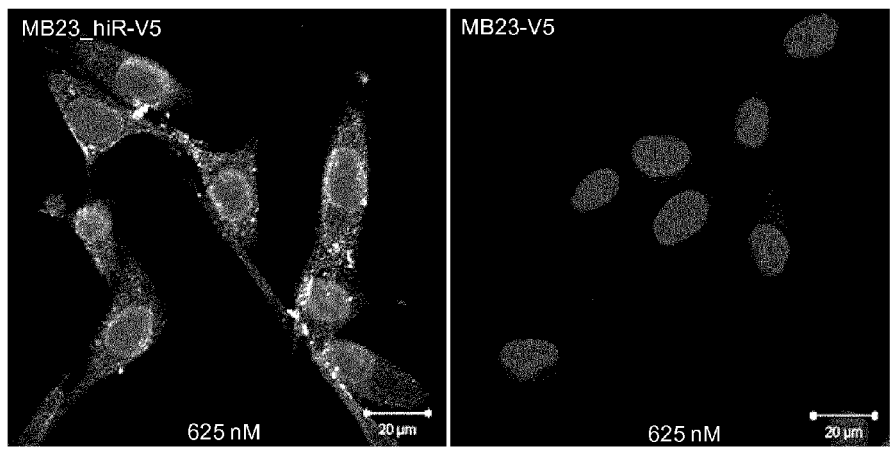

FIG. 3: Intracellular uptake of 625 nM non-cationized MB23-V5 and cationized MB23_hiR-V5 (SEQ ID NO: 2) in human glioblastoma cells (U87.MG). Alphabody was incubated 2 h in presence of 10% serum with cells at 37° C. After PBS washing, fixing and permeabilizing cells, intracellular Alphabody was visualized with a primary anti-V5 antibody and a secondary goat anti-mouse antibody labeled to Alexa 488. The nucleus was stained with DAPI. Images correspond to the image of a 1 µm slice of the recorded Z-stacks.

Figure 4:
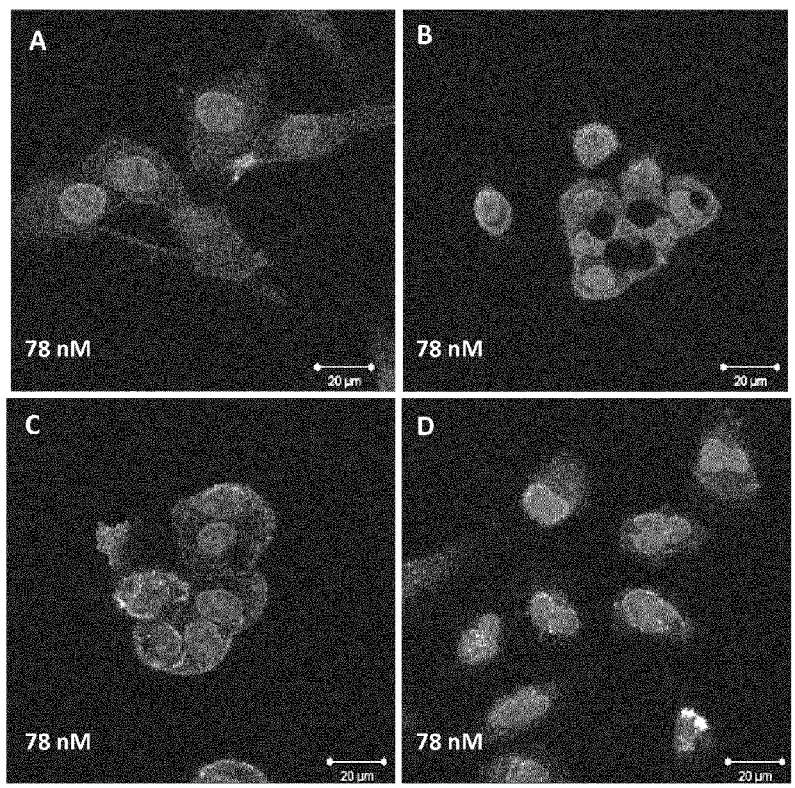

FIG. 4: Intracellular uptake of 78 nM cationized Alphabody MB23_hiR-V5 (SEQ ID NO: 2) in 4 different cell lines (A: human glioblastoma—(U87.MG), B: pancreatic cancer—(BxPC3), C: non small cell lung cancer—(H1437) and D: human liposarcoma (SW872) cells). Alphabody was incubated 2 h in presence of 10% serum with cells at 37° C. After PBS washing, fixing and permeabilizing cells, intracellular Alphabody was visualized with a primary anti-V5 antibody and a secondary goat anti-mouse antibody labeled to Alexa 488. The nucleus was stained with DAPI. Images correspond to the image of a 1 µm slice of the recorded Z-stacks.

FIG. 5: Intracellular uptake of 500 nM cationized Alphabody MB23_hiR-V5 (SEQ ID NO: 2) in human glioblastoma cells (U87.MG). Alphabody was incubated for different time periods with cells in presence of 10% serum at 37° C. After heparin (100 Units/ml) washing, fixing and permeabilizing the cells, intracellular Alphabody was visualized with a primary anti-V5 antibody and a secondary goat anti-mouse antibody labeled to Alexa 488. The nucleus was stained with DAPI. Images correspond to single cell images of a 1 µm slice of the recorded Z-stacks.

FIG. 6: Sequence of Alphabodies AB1_hiKR1-V5 (SEQ ID NO: 4) and AB1_A2aF_hiKR3-V5 (SEQ ID NO: 6). Arg/Lys decoration is shown in bold and C-terminal V5 tag is shown underlined.

Figure 7:
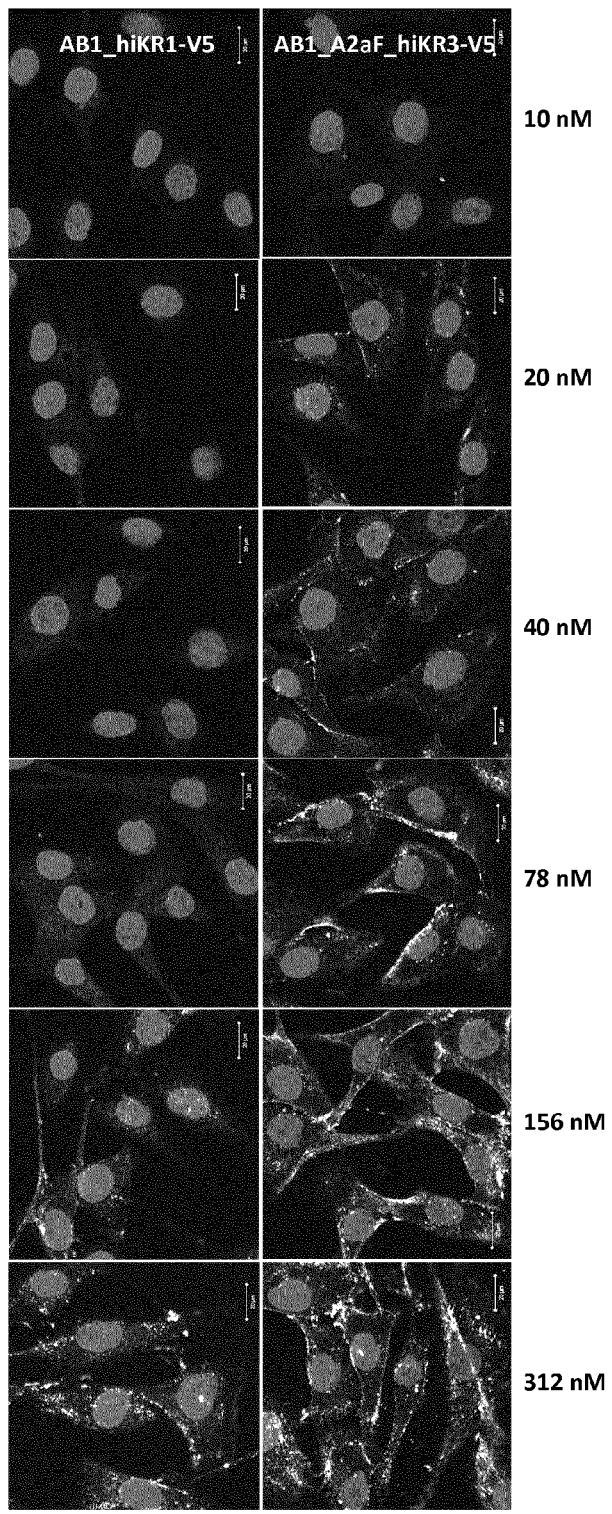

FIG. 7: Intracellular uptake of different concentrations (10 nM, 20 nM, 40 nM, 78 nM, 156 nM and 312 nM) AB1_hiKR1-V5 (SEQ ID NO: 4) and AB1_A2aF_hiKR3-V5 (SEQ ID NO: 6) in human glioblastoma cells (U87.MG). Alphabody was incubated 2 h in presence of 10% serum with cells at 37° C. After PBS washing, fixing and permeabilizing cells, intracellular Alphabody was visualized with a primary anti-V5 antibody and a secondary goat anti-mouse antibody labeled to Alexa 488. The nucleus was stained with DAPI. Images correspond to the image of a 1 µm slice of the recorded Z-stacks.

Figure 8:
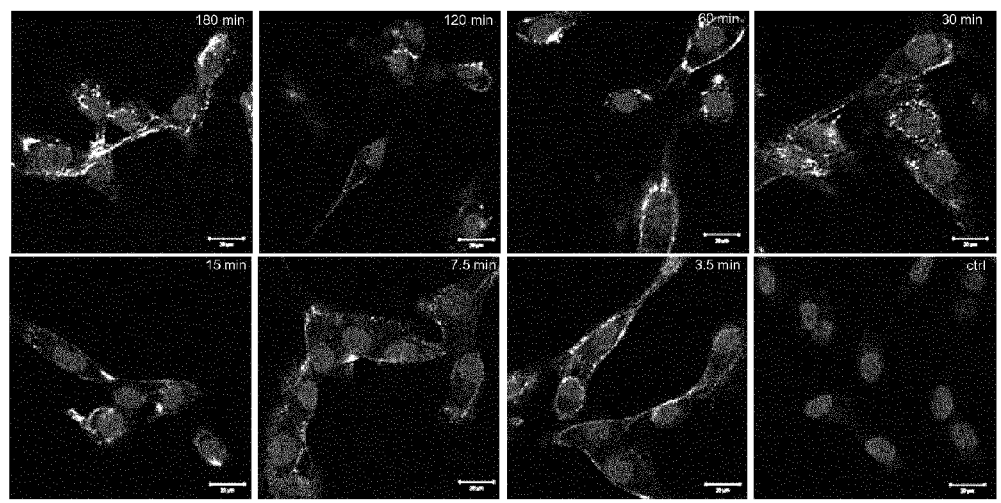

FIG. 8: Kinetics of intracellular uptake of 500 nM AB1_A2aF_hiKR3-V5 (SEQ ID NO: 6) in human glioblastoma cells (U87.MG). Alphabody was incubated for 180 min, 120 min, 60 min, 30 min, 15 min, 7.5 min and 3.5 min in presence of 10% serum with cells at 37° C. After heparin (100 Units/ml) washing, fixing and permeabilizing cells, intracellular Alphabody was visualized with a primary anti-V5 antibody and a secondary goat anti-mouse antibody labeled to Alexa 488. The nucleus was stained with DAPI. Images correspond to one slice of 1 µm of the recorded Z-stacks.

Figure 9:
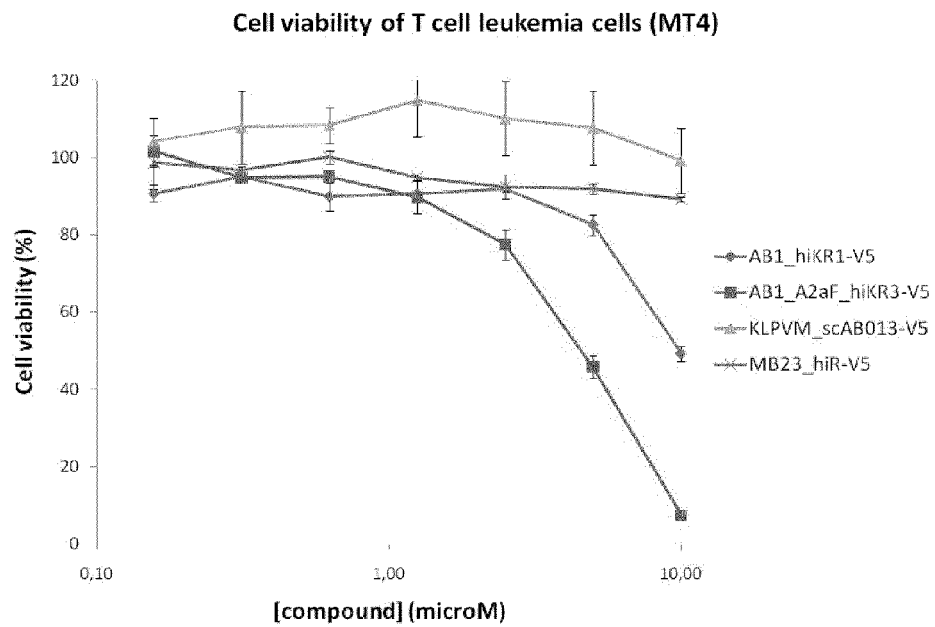

FIG. 9: Cell viability of human T cell leukemia cells (MT4) in presence of serial dilutions of Alphabody. Cell viability was measured after 48 h treatment with Alphabodies. Data correspond to mean values±SD of triplicates. Cell viability was expressed as percentage relative to non-treated control cells.

Figure 10:
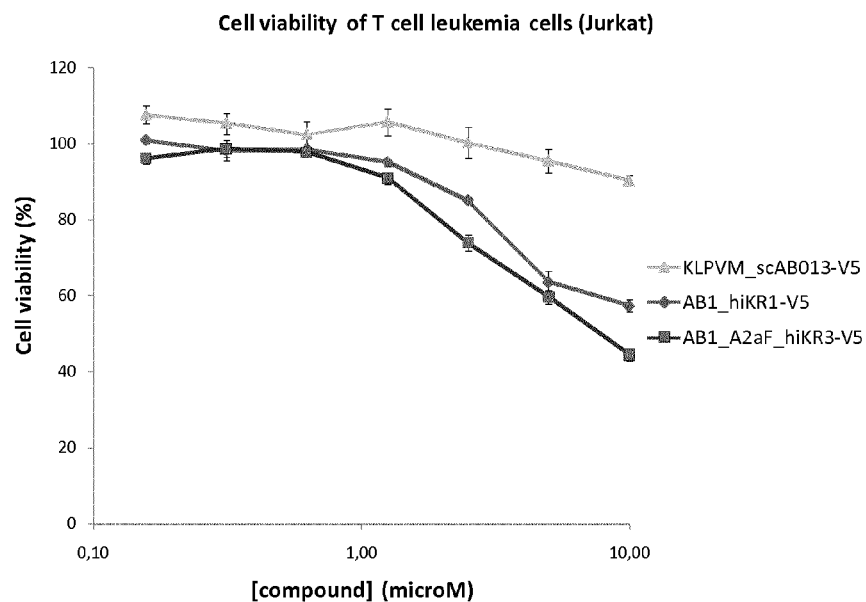

FIG. 10: Cell viability of human T cell leukemia cells (Jurkat) in presence of serial dilutions of Alphabody. Cell viability was measured after 48 h treatment with Alphabodies. Data correspond to mean values±SD of triplicates. Cell viability was expressed as percentage relative to non-treated control cells.

Figure 11:
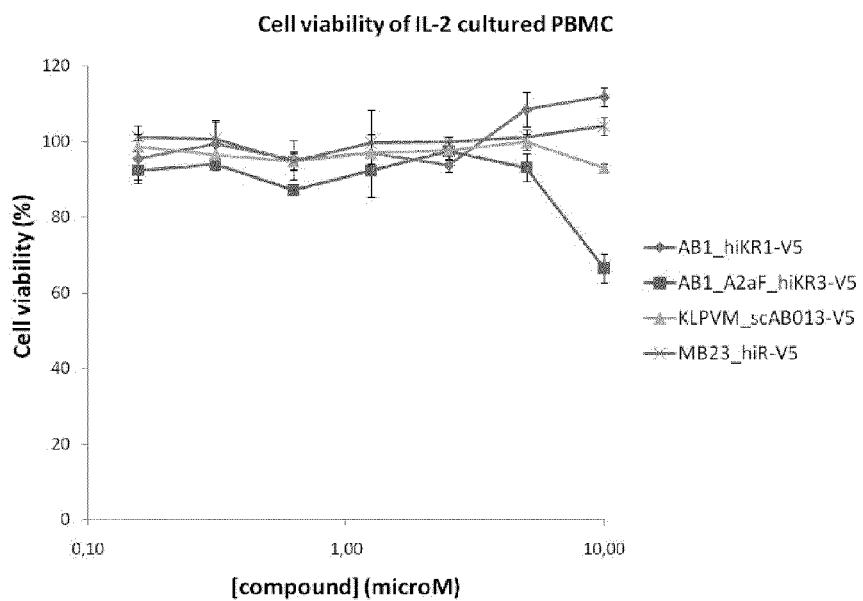

FIG. 11: Cell viability of PBMC in presence of serial dilutions of Alphabody. Cell viability was measured after 48 h treatment with Alphabodies. Data correspond to mean values±SD of triplicates. Cell viability was expressed as percentage relative to non-treated control cells.

Figures 12, 13:
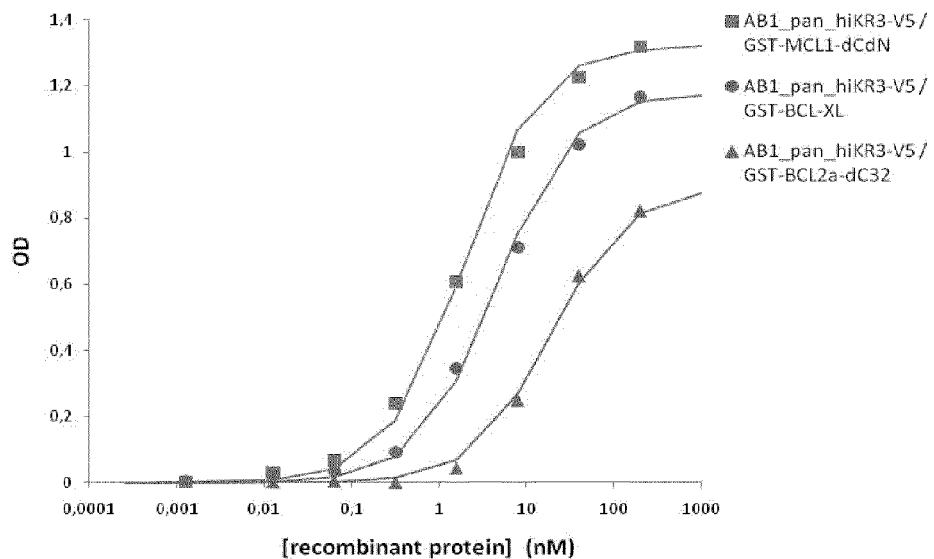

FIG. 12: Sequence of cationized Alphabody AB1_pan_hiKR3-V5 with C-terminal His-tag and V5 tag (SEQ ID NO: 10). Arginine/lysine decoration is shown in bold and N-terminal V5 tag is shown underlined. The sequence is shown as fragments, labeled 'Helix A', 'Loop 1', 'Helix B', 'Loop 2', 'Helix C', 'His-tag' and 'V5-tag', respectively, to distinguish between different structural elements. The full AB1_pan_hiKR3-V5 sequence is a single polypeptide sequence consisting of these fragments in the order as shown.

FIG. 13: Binding of recombinant BCL-2 family proteins to Alphabody AB1_pan_hiKR3-V5. Alphabody (500 nM) was captured by immobilized anti-V5 antibody (5 microg/ml) to a microtiterplate. Binding of five-fold dilutions of Glutathione S transferase (GST)-tagged recombinant BCL-2 family proteins MCL-1, BCL-XL and BCL-2a was detected using a anti-GST antibody conjugated to Horse Radish Peroxidase. Plates were read at 492 nm and 630 nm.

Figure 14:
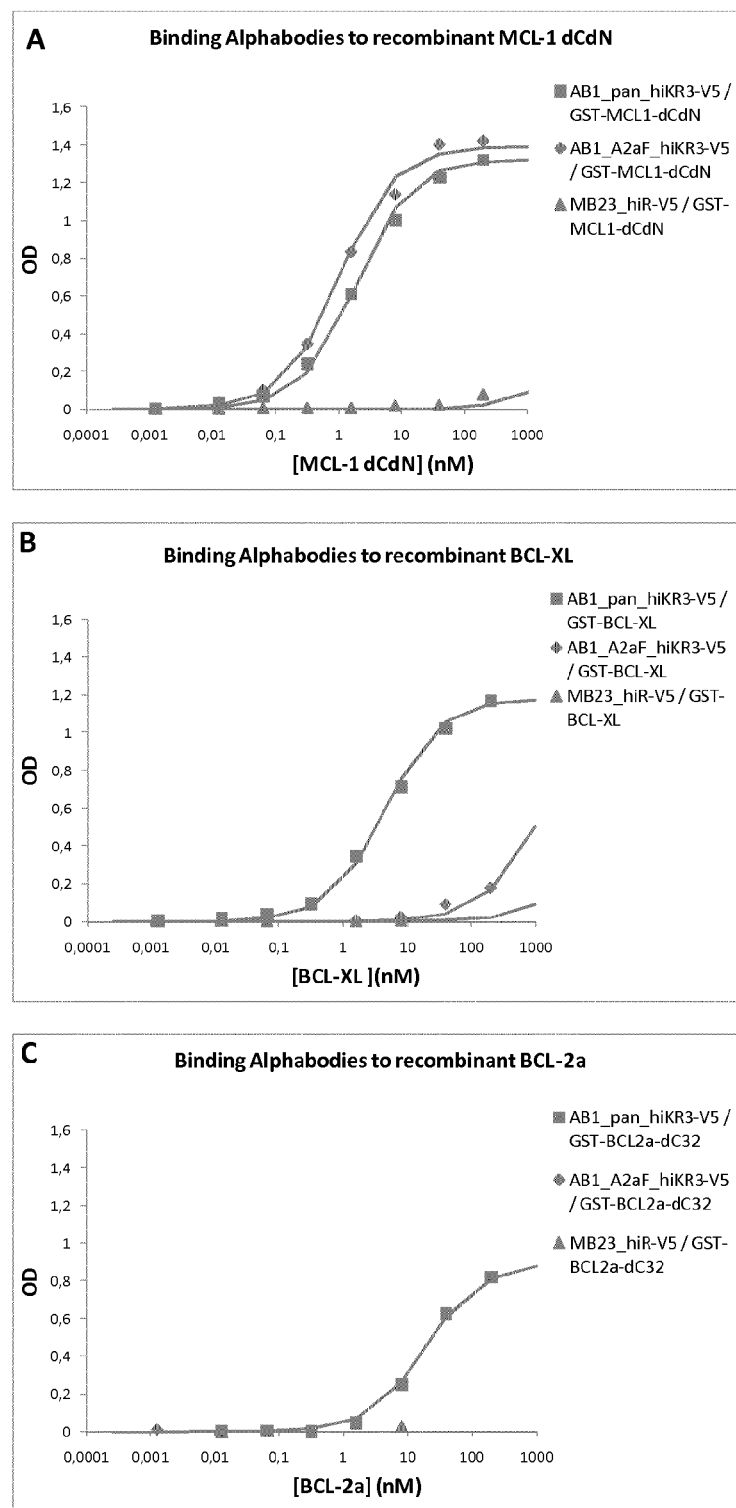

FIG. 14: Binding of recombinant BCL-2 family proteins to Alphabody AB1_pan_hiKR3-V5, AB1_A2aF_hiKR3-V5 and MB23_hiR-V5. Alphabody (500 nM) was captured by immobilized anti-V5 antibody (5 microg/ml) to a microtiterplate. Binding of five-fold dilutions of Glutathione S transferase (GST)-tagged recombinant BCL-2 family proteins MCL-1 (panel A), BCL-XL (panel B) and BCL-2a (panel C) was detected using a anti-GST antibody conjugated to Horse Radish Peroxidase. Plates were read at 492 nm and 630 nm.

Figure 15:
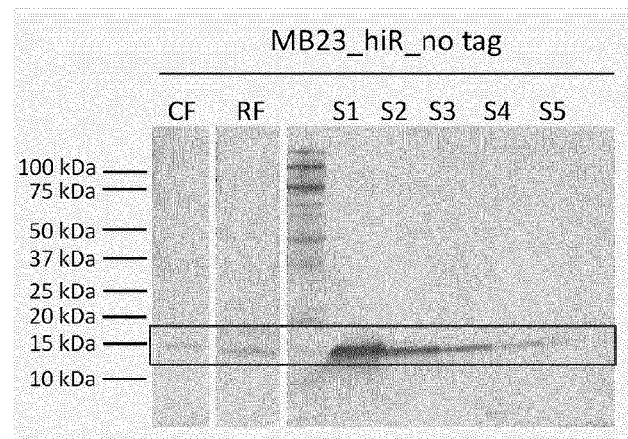

FIG. 15: Presence of MB23 hiR no tag in the cytosolic compartment of Jurkat cells as demonstrated by immunoblot of the cellular cytosolic (CF) and rest (RF) fractions of the cells after digitonin permeabilization.

Figure 16:
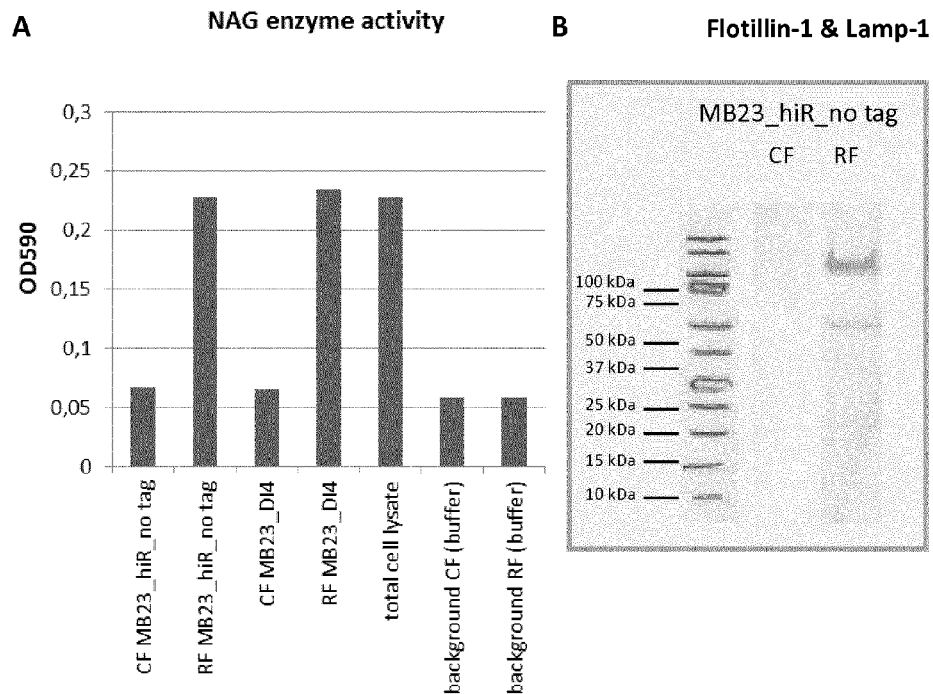

FIG. 16: Demonstration of effect of digitonin membrane permeabilization on cytosolic content using endosomal markers NAG (Panel A) and Flotillin-1 and Lamp-1 (Panel B). Panel A: enzymatic activity; Panel B: blotting with anti-his antibody.

Figure 17:
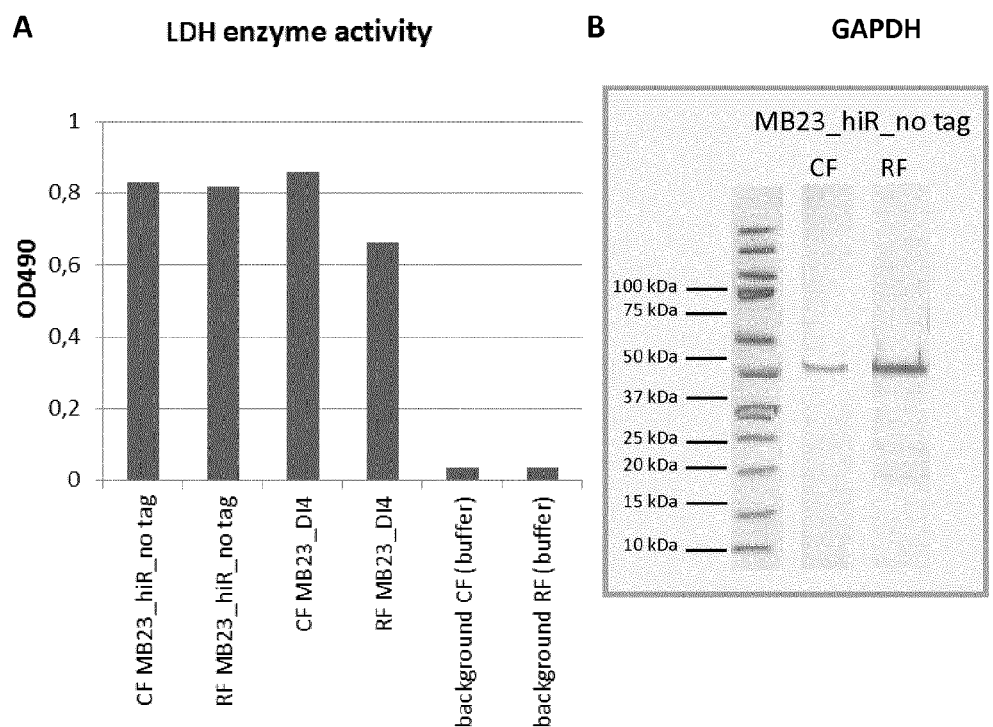

FIG. 17: Demonstration of effect of digitonin membrane permeabilization on cytosolic content using cytosolic markers LDH (Panel A) and GADPH (Panel B). Panel A: enzymatic activity; Panel B: blotting with anti-his antibody.

EXAMPLES

I. Introduction

Many molecules acting intracellularly have been identified as being potentially interesting targets for therapeutic applications. Among those, the proteins involved in the process of apoptosis form an important class of intracellular target molecules. As described recently (Quinn et al., Expert Opinion, 2011, 20: 1397-1411; Akgul, Cell. Mol. Life. Sci. 2009, 66:1326-1336 and references cited therein), it is well known that apoptosis is a key process for maintenance of cellular homeostasis in an organism. Apoptosis can occur by two interrelated pathways: the extrinsic and intrinsic pathways of apoptosis. The extrinsic pathway involves the activation of cell surface death receptors (Fas, TNFR) by extracellular ligands such as FasL or TNF. The intrinsic pathway, which can be initiated by a variety of stress signals, involves permeabilization of the outer membrane of mitochondria, which leads to cytochrome c release leading to additional steps in the apoptosis process, involving the cleavage and activation of caspase-9 and, finally cell death.

It is furthermore well known that the members of the BCL-2 family of proteins (also noted as Bcl-2 family of proteins) are the main proteins involved in the regulation and control of apoptotic processes. The BCL-2 family of proteins includes both pro-apoptotic members as well as anti-apoptotic members. This family of proteins is named after BCL-2, the founding member of this family of proteins which was discovered in studies on B-cell lymphoma.

Based on structural and functional properties, the BCL-2 family of proteins are typically divided into three subgroups: two subgroups of pro-apoptotic BCL-2 members and one subgroup of anti-apoptotic BCL-2 members.

The anti-apoptotic subgroup includes the members BCL-2, MCL-1, BCL-w, BCL-$X_L$ and BFL-1/A1 (these proteins are also sometimes noted in lower-case notation, Bcl-2, Mcl-1, Bcl-w, Bcl-$X_L$, Bfl-1/A1). These proteins act as survival factors by binding or capturing a critical apoptosis inducing domain of pro-apoptotic BCL-2 family members (Stewart et al., Nature Chemical Biology, 2010, 6, 595-601). This domain is known as the BCL-2 homology domain 3 (BH3). Anti-apoptotic proteins have along their surface a hydrophobic binding region that engages BH3 alpha-helices (Sattler et al., Science, 1997, 275: 983-986). Whereas BCL-2, BCL-XL and BCL-W contain four BH (BCL-2 homology) domains (noted as BH1, BH2, BH3 and BH4), MCL-1 and BFL-1/A1 lack a well-defined BH4 domain.

One of the two pro-apoptotic subgroups contains Bax and Bak (also noted in upper case as BAX and BAK) which have multiple BH (BCL-2 homology) domains (BH1, BH2 and BH3). Members of the other pro-apoptotic subgroup (including BAD, BID, BIM, NOXA, PUMA) contain only BH3 domains and are hence called BH3-only proteins.

The anti-apoptotic members of the BCL-2 family play an important role in tumor cell survival and can be considered as valuable targets for the treatment of cancer. Indeed, these survival proteins are expressed in a broad range of human cancers. For example, MCL-1 has been reported to be overexpressed in many cancer types (breast, ovarian, renal, prostate, melanoma, pancreatic, hepatocellular carcinoma, head and neck, multiple myeloma, colon, lung, leukemia and lymphoma) (Quinn et al., Expert Opinion, 2011, 20: 1397-141).

Consequently, there is an important interest in drug discovery related to the development of BH3 mimics to block anti-apoptotic proteins.

For example, ABT-737 is a BH3-mimic that binds to BCL-2, BCL-XL and BCL-w but not to MCL-1 or BFL-1/A1 (Lee et al, Cell Death and Differentiation (2007), 14, 1711-1719). This difference in recognition can be explained by differences in the binding groove, where it is known that the MCL-1 binding groove is more electropositive than the other anti-apoptotic proteins.

Also, hydrocarbon stapled peptides mimicking a BH3 alpha-helix have been produced thereby aiming at optimizing affinity and preserving the binding selectivity. Such approach was recently worked out by Stewart et al. (Nature Chemical Biology, 2010, 6, 595-601) who derived from the anti-apoptotic MCL-1 BH3 helix an exclusive MCL-1 inhibitor.

However, these stapled peptides generally suffer from the fact that only an intermediate level of alpha-helicity is observed (e.g. 36% alpha-helicity was noted for the doubly stapled SAH-gp41$_{626-662}$ peptide (Bird et al, PNAS, 2010, 107, 14093-14098)); and that the required stapling between helical turns is an artifact which itself may have an unpredictable effect on biological activity.

In the following examples it is described how Alphabodies were designed that mimic the BH3 domain of MCL-1 and bind to MCL-1 aiming at blocking the MCL-1 interactions with pro-apoptotic proteins to drive cancer/tumor cells to a programmed cell death.

II. Intracellular Uptake of Alphabodies Comprising a CPAB Motif

Example 1. Intracellular Uptake of Cationized CPAB Alphabody MB23_hiR-V5

This Example describes the intracellular uptake of a cationized Alphabody in function of time and in function of Alphabody concentration in different cell types including cancer and non-cancer cells. To study the cellular uptake capacity of cationized Alphabodies, we initially chose an Alphabody directed against IL-23, named MB23. To preserve the IL-23 binding site located on the A and C helix, 8 Arg were added in the B helix, resulting in a positively charged Alphabody referred to as MB23_hiR-V5 (SEQ ID NO: 2) (charge of +9) (FIG. 1).

Additionally, Alphabody cellular uptake mechanisms were explored by studying the temperature dependency of uptake, dependency on presence of glycosaminoglycans and influence of presence of serum in cell culture medium on cell penetration.

The uptake was studied by confocal microscopy and intracellular Alphabody was visualized using an anti-V5 antibody recognizing the V5 tag fused, together with a His-tag, to C-terminus of the Alphabody. All experiments were performed on fixed and permeabilized cells. Control experiments with non-permeabilized experiments were included (data not shown).

1.1 Methods Used

Cell penetration in function of concentration and time was studied with the reference cationized Alphabody MB23_hiR-V5 (SEQ ID NO: 2) in 8 different cell lines comprising 6 cancer cell lines and 2 non-cancer cell lines. To understand the mechanism of intracellular Alphabody uptake, temperature dependency, heparansulfate dependency and serum dependency of cell penetration was studied.

1.1.1 Expression and Purification of MB23 hiR-V5

Cationized Alphabody MB23_hiR-V5 (SEQ ID NO: 2) was expressed in the soluble fraction of E. coli bacteria. Protein was purified by Ni-NTA chromatography followed by desalting and buffer exchange procedures. Protein was solubilized in 20 mM citric acid pH 3.0 (5.3 mg/ml).

1.1.2 Intracellular Uptake of Cationized Alphabody MB23 hiR-V5

Intracellular uptake was studied in 6 different cancer cell lines (U87.MG, BxPC-3, H1437, SW872, MT-4 and Jurkat) and 3 non-cancer cell lines (HEK, CHO-K1 and CHO.pgSA) (Table 1).

Adherent cell lines (U87.MG, BxPC-3, H1437, SW872, HEK, CHO-K1 and CHO.pgSA) were cultured in DMEM+ 10% Foetal Bovine Serum (FBS) and seeded in LabTek chambers at 10.000 cells/chamber and incubated overnight at 37° C. and 5% $CO_2$. The next day cationized Alphabody (dilution series or single concentration) was incubated with the seeded cells for 2 h or different time periods ranging from 3.5 min to 48 h at 37° C. and 5% $CO_2$. After incubation with the Alphabodies, cells were washed 4 times (5 min/wash) with PBS (containing Mg and Ca (DPBS)).

TABLE 1

Cell lines used for intracellular uptake studies

| Cell line | Description |
| --- | --- |
| U87.MG | Human glioblastoma cells |
| BxPC-3 | Human pancreatic cancer cells |
| H1437 | Human non-small cell lung cancer cells |
| SW872 | Human liposarcoma cells |
| MT-4 | Human T cell leukemia cells |
| Jurkat | Human T cell leukemia cells |
| HEK | Human Embryonic Kidney cells |
| CHO-K1 | Chinese Hamster Ovary cells |
| CHO.pgSA | Chinese Hamster Ovary cells deficient for glycosaminoglycan synthesis |

Suspension cell lines (MT4 and Jurkat) were cultured in RPMI+10% FBS and seeded in 96-well plates at 100.000 cells/well. Dilution series of cationized Alphabodies were added for 2 h to the cells in the 96-well plates at 37° C. and 5% $CO_2$. In parallel, poly-Lysine was added to the LabTek chambers for 2 h at room temperature (RT) to prepare the glass slides of the LabTek chambers for cell attachment. After 2 h cells were washed two times (5 min/wash) and added to the poly-Lys coated LabTek chambers for 1 h at RT (=cell attachment).

To visualize intracellular Alphabodies, cells were fixed with 4% formaldehyde at 4° C. for 10 min followed by permeabilization with 0.1% Triton X-100 at RT for 15 min. Cells were washed twice (10 min/wash) with glycine (0.75 g/100 ml) to stop the crosslinking of formaldehyde followed by a wash with DPBS (5 min/wash).

Cells were blocked with blocking buffer (DPBS+1% BSA) for 10 min at RT followed by incubation with the primary antibody directed against the V5 tag of the Alphabody (mouse anti-V5 Ab, Invitrogen, 46-0705) diluted at 1/400 in blocking buffer for 1 h at RT. Cells were washed 3 times (5 min/wash) with blocking buffer followed by addition of the secondary antibody, goat anti-mouse antibody labeled to Alexa488 (Invitrogen, A-10680) diluted 1/300 in blocking buffer and DAPI (4',6-Diamidino-2-Phenylindole, dihydrochloride) (nuclear staining) (1/100) for 30 min at RT. Finally, cells were washed 3 times (5 min/wash) with blocking buffer, 150 ul of DPBS was added and plates were read on a Zeiss Axiovert 200, LSM 510 Meta confocal microscope.

1.2 Results 1.2.1 Intracellular Uptake of Cationized MB23 hiR-V5 in Different Cell Lines Intracellular uptake of two-fold dilutions of cationized MB23_hiR-V5 (SEQ ID NO: 2) starting at 312 nM was studied in the human glioblastoma cell line U87.MG. After 2 h incubation of Alphabody with cells, intracellular Alphabody was detected with an anti-V5 antibody and a secondary Alexa488 labeled antibody. FIG. 2 shows the dose-dependent uptake of MB23_hiR-V5 (312 nM to 1.2 nM) in U87.MG cells. The diffuse fluorescent pattern indicates cytosolic localization of the Alphabody. The lower concentration limit of detectable intracellular uptake of cationized MB23 in human glioblastoma cells was 4.9 nM. At that concentration a fluorescent signal higher than the control signal (cells without Alphabody) was still visible.

Uptake of the corresponding non-cationized Alphabody MB23-V5 was studied under the same conditions in human glioblastoma cells. There was no detectable intracellular uptake of non-cationized MB23 demonstrating that uptake of MB23_hiR-V5 is due to the presence of the cationization motifs (FIG. 3).

Dose dependent uptake of MB23_hiR-V5 (1250 nM, 312.5 nM, 156.3 nM, 78.1 nM, 39.1 nM, 19.5 nM and 9.8 nM) was studied in 5 additional cancer cell lines (BxPC-3, H1437, SW872, MT-4, Jurkat) and two non-cancer cell lines (HEK, CHO-K1). A dose dependent intracellular uptake was observed for all tested cell types including the non-cancer cells). Intracellular uptake of cationized Alphabody MB23_hiR-V5 was examined at a concentration of 78 nM in 4 different cell lines (U87.MG, BxPC-3, H1437 and SW872). Cationized Alphabody penetrated in all analyzed cell types albeit not to the same extent (qualitative comparison) (FIG. 4).

The lower concentration limits for intracellular uptake were qualitatively determined on the confocal microscopy images and are summarized in Table 2. For all cell lines, except the human glioblastoma cells (U87.MG), the lowest concentration tested was 9.8 nM. At the lowest concentration tested, intracellular Alphabody was detected in BxPC-3, H1437 and CHO-K1 cells. Higher concentrations of cationized Alphabody were required to obtain a fluorescent signal above background for SW872 and HEK cells. The highest concentrations of Alphabody for intracellular uptake were required in the human T cell leukemia cell lines MT4 and Jurkat.

TABLE 2

Lower concentration limit for intracellular uptake of cationized MB23_hiR-V5 in the 8 different cell lines.

| Cell type | Lower concentration limit for uptake |
| --- | --- |
| Glioblastoma cells (U87) | 4.9 nM |
| Pancreatic cancer (BxPC3) | 9.8 nM |
| Non small cell lung cancer (H1437) | 9.8 nM |
| Liposarcoma cells (SW872) | 19.5 nM |
| T cell leukemia (Jurkat) | 1250 nM |
| T cell leukemia (MT4) | 156 nM |
| Chinese Hamster Ovary cells (CHO.K1) | 9.8 nM |
| HEK cells | 39.1 nM |

1.2.2 Intracellular Uptake of Cationized MB23 hiR-V5

(i) Influence of Serum on Intracellular Uptake of MB23 hiR-V5

To determine the impact of the presence of serum on intracellular uptake, intracellular uptake of a dilution series of cationized Alphabody MB23_hiR-V5 (SEQ ID NO: 2) in human glioblastoma cells (U87.MG) was studied. Alphabody was incubated 2 h with cells in presence and absence of 10% serum at 37° C. After PBS washing, fixing and permeabilizing the cells, intracellular Alphabody was visualized with a primary anti-V5 antibody and a secondary goat anti-mouse antibody labeled to Alexa 488. The nucleus was stained with DAPI. In summary, there were only minor differences in uptake efficacy between the serum free and 10% serum conditions. Difference in uptake was the most pronounced at the highest concentration of Alphabody (1250 nM) (data not shown).

(ii) Influence of Heparansulfate and Chondroitinsulfate on Intracellular Uptake of MB23 hiR-V5

The potential influence of heparansulfate and chondroitinsulfate was studied by using CHO.pgsA-745 cells deficient in heparansulfate synthesis. These cells (CHO.pgsA-745) are defective in xylosyltransferase and do no express heparansulfates and chondroitinsulfates at their cell surface. Intracellular uptake of a dilution series of cationized Alphabody MB23_hiR-V5 in CHO-K1 and CHO.pgsA-745 cells was studied. Alphabody was incubated 2 h with cells in presence of 10% serum at 37° C. After PBS washing, fixing and permeabilizing the cells, intracellular Alphabody was visualized with a primary anti-V5 antibody and a secondary goat anti-mouse antibody labeled to Alexa 488. The nucleus was stained with DAPI. The results showed that intracellular uptake in heparin/chondroitinsulfate (HS/CS) deficient cells is not completely abrogated (data not shown). Yet, the uptake was clearly less efficient in HS/CS deficient cells. This suggests that uptake of cationized Alphabodies is partially, but not fully dependent on the presence of the negatively charged HS/CS moieties.

(iii) Influence of Temperature on Intracellular Uptake of MB23 hiR-V5

Uptake of cationized Alphabody was also studied at 4° C. to determine whether cell penetration of cationized Alphabodies is an energy dependent or energy independent process. For this purpose, intracellular uptake of a dilution series of cationized Alphabody MB23_hiR-V5 in human glioblastoma cells (U87.MG) was studied. Alphabody was incubated 2 h with cells in presence of 10% serum at 37° C. and 4° C. After PBS washing, fixing and permeabilizing the cells, intracellular Alphabody was visualized with a primary anti-V5 antibody and a secondary goat anti-mouse antibody labeled to Alexa 488. The nucleus was stained with DAPI. Only minor differences in uptake were observed when comparing Alphabody cell penetration at 37° C. and 4° C. (data not shown). These data indicate a substantially energy independent Alphabody cell penetration mechanism, which relies primarily on direct penetration of the Alphabodies through the membranes.

1.2.3 Kinetics of Intracellular Uptake of MB23 hiR-V5

To obtain insights in the kinetics of uptake of cationized Alphabodies and the fate of the intracellular Alphabodies after prolonged incubation times, experiments with short (240 min, 120 min, 60 min, 30 min, 15 min, 7.5 min, 3.5 min) and long (48 h, 24 h and 12 h) Alphabody incubation times with human glioblastoma cells (U87.MG) were performed at two different Alphabody concentrations (1250 nM and 500 nM) (data not shown).

The kinetics of the intracellular uptake were identical for both concentrations of Alphabody. After 3.5 minutes, Alphabody was already detected in the cell. These data suggest that the uptake of Alphabodies into cells is a fast process. Prolonged incubation of cationized Alphabodies on cells resulted in loss of intracellular Alphabody, in particular after 48 hours.

1.2.4 Effects of Heparin Washing on Binding of Alphabody to the Extracellular Cell Membrane Heparin washes (100 U/ml) of cells were performed after Alphabody incubation to analyze whether (1) heparin washes removed Alphabody from the extracellular membrane and (2) to ensure that observed intracellular Alphabody was not an artefact of the staining procedure (extracellular Alphabody entering the cells due to the staining treatment (i.e. fixation and permeabilization of the cells). After Alphabody incubation, cells were washed with PBS or heparin and were fixed and permeabilized or fixed only without permeabilization (=extracellular Alphabody staining). Two different concentrations of Alphabody (1250 nM and 500 nM) were studied in these experiments:

Intracellular uptake of 1250 nM and 500 nM cationized Alphabody MB23_hiR-V5 (SEQ ID NO: 2) in human glioblastoma cells (U87.MG). Alphabody was incubated for 2 h with U87.MG cells in presence of 10% serum at 37° C. After PBS or heparin washing, fixing and permeabilizing/not permeabilizing the cells, intracellular Alphabody was visualized with a primary anti-V5 antibody and a secondary goat anti-mouse antibody labeled to Alexa 488. The nucleus was stained with DAPI (data not shown).

Whereas intracellular Alphabody was observed for both heparin and PBS washed cells, membrane bound Alphabody was only visible on the PBS washed cells. When cells were not permeabilized resulting in visualization of extracellular Alphabody, weaker Alphabody staining was observed for the heparin washed cells compared to the PBS washed cells.

These results demonstrate that heparin removes extracellular membrane bound Alphabody albeit removal was not complete and intracellular Alphabody detected after permeabilization of the cells is not a technical artifact of extracellular Alphabody being internalized due to the experimental procedure.

1.2.5 Kinetics of Uptake MB23 hiR-V5 after Removing Extracellularly Bound Alphabody From previous experiments, it followed that heparin removes a large fraction of the extracellularly bound Alphabody. Therefore, kinetics of uptake of MB23_hiR-V5 (SEQ ID NO: 2) were studied using heparin washes. This protocol allowed to evaluate the evolution in intracellular Alphabody while discarding the majority of extracellularly bound Alphabody. Images of intracellular uptake were recorded on multiple cells but also on single cells providing a more detailed image of the time dependent intracellular uptake (FIG. 5).

After 3.5 min, there was intracellular Alphabody visible when compared to the control image (cells without Alphabody). The increase of fluorescent signal (increase in intracellular Alphabody) in function of time was more visible when cells were washed with heparin.

When analyzing the single cell images, an evolution in the fluorescent pattern in function of time became obvious. At the earlier time points, the intracellular membrane staining was clearly visible (up to 30 min). After 30 minutes, membrane staining faded and vesicles were present in the cytoplasm, moving further away from the membrane (FIG. 5).

1.3 Conclusions

The results of the present Example showed that cationized Alphabody MB23_hiR-V5 (with charges in the B helix) penetrates in a dose dependent manner in different cell types including cancer and non-cancer cell lines. The uptake efficacy and the uptake pattern is cell type dependent.

Alphabody concentrations as low as 5 to 10 nM resulted after 2 h cell incubation in intracellular uptake of Alphabodies.

Intracellular uptake of cationized Alphabodies is not abrogated at 4° C., indicating that Alphabody uptake is driven primarily by an energy independent mechanism probably relying on direct penetration of the cell membrane.

These findings suggest that cationized Alphabodies follow different routes of intracellular uptake.

The uptake process of cationized Alphabodies is a fast process. After 3.5 min, Alphabody was present inside the cell.

Heparin removes a large fraction of extracellular bound Alphabody. Kinetic uptake experiments using heparin washes were performed to discard the staining of extracellularly bound Alphabody. The results were essentially similar to the results obtained with PBS washes, but the increase in intracellular Alphabody concentration over time was more pronounced. Analysis of single cells demonstrated an evolution in the fluorescence pattern, indicating the movement (i.e. diffusion) of the Alphabody from the inner cell membrane into the intracellular space.

Example 2. Intracellular Uptake of CPAB Alphabodies Directed Against MCL-1

This example describes the intracellular uptake of Alphabodies AB1_hiKR1-V5 (SEQ ID NO: 4) and AB1_A2aF_hiKR3-V5 (SEQ ID NO: 6), two Alphabodies directed against the intracellular target MCL-1. These Alphabodies were designed for intracellular uptake by cationization (i.e., by decoration with Arg/Lys amino acid residues). It was shown, as described below, that these Alphabodies were capable of inducing cell death after 48 h in viability assays, in particular of T cell leukemia cells (MT4).

2.1 Methods Used

Intracellular uptake of the Alphabodies AB1_hiKR1-V5 (SEQ ID NO: 4) and AB1_A2aF_hiKR3-V5 (SEQ ID NO: 6) was studied in a panel of cancer and non-cancer cell lines in function of Alphabody concentration. The uptake was studied by confocal microscopy and intracellular Alphabody was visualized using an anti-V5 antibody recognizing the C-terminal V5 tag of the Alphabody. All experiments were performed on fixed and permeabilized cells. Control experiments with non-permeabilized experiments were included.

These Alphabodies contained the MCL-1 binding site in the B helix and displayed different cationization patterns as shown in FIG. 6. Lys and Arg residues were used to decorate the Alphabodies, resulting in net charges of +11 and +19 for AB1_hiKR1-V5 (SEQ ID NO: 4) and AB1_A2aF_hiKR3-V5 (SEQ ID NO: 6), respectively. The Alphabody AB1_A2aF_hiKR3-V5 was designed to present a better core packing. Additional differences between AB1_A2aF_hiKR3-V5 and AB1_hiKR3-V5 were a shorter loop 1 sequence and a longer His-tag for the A2aF variant (FIG. 6).

Cell penetration in function of concentration was studied in 8 different cell lines comprising 6 cancer cell lines and 2 non-cancer cell lines.

2.1.1 Expression and Purification of AB1_hiKR1-V5 and AB1_A2aF_hiKR3-V5

Cationized Alphabodies AB1_hiKR1-V5 (SEQ ID NO: 4) and AB1_A2aF_hiKR3-V5 (SEQ ID NO: 6) were expressed in the soluble fraction of *E. coli* bacteria. Proteins were purified by Ni-NTA chromatography followed by desalting and buffer exchange procedures. Proteins were solubilized in 20 mM citric acid pH 3.0 (2.8 mg/ml for AB1_hiKR1-V5 and 3.9 mg/ml for AB1_A2aF_hiKR3-V5).

2.1.2 Intracellular Uptake of Cationized Alphabodies AB1_hiKR1-V5 and AB1_A2aF_hiKR3-V5

Intracellular uptake was studied in 6 different cancer cell lines (U87.MG, BxPC-3, H1437, SW872, MT-4 and Jurkat) and 2 non-cancer cell lines (HEK, CHO-K1) (Table 3).

Adherent cell lines (U87.MG, BxPC-3, H1437, SW872, HEK, CHO-K1 and CHO.pgSA) were cultured in DMEM+ 10% Foetal Bovine Serum (FBS) and seeded in LabTek chambers at 10.000 cells/chamber and incubated overnight at 37° C. and 5% CO$_2$. The next day, cationized Alphabody (dilution series or single concentration) was incubated with the seeded cells for 2 h or different time periods ranging from 3.5 min to 48 h at 37° C. and 5% CO$_2$. After incubation with the Alphabodies, cells were washed 4 times (5 min/wash) with PBS (containing Mg and Ca (DPBS)).

TABLE 3

Cell lines used for intracellular uptake studies

| Cell line | Description |
|---|---|
| U87.MG | Human glioblastoma cells |
| BxPC-3 | Human pancreatic cancer cells |
| H1437 | Human non-small cell lung cancer cells |
| SW872 | Human liposarcoma cells |
| MT-4 | Human T cell leukemia cells |
| Jurkat | Human T cell leukemia cells |
| HEK | Human Embryonic Kidney cells |
| CHO-K1 | Chinese Hamster Ovary cells |

Suspension cell lines (MT4 and Jurkat) were cultured in RPMI+10% FBS and seeded in 96-well plates at 100.000 cells/well. Dilution series of cationized Alphabodies were added for 2 h to the cells in the 96-well plates at 37° C. and 5% CO$_2$. In parallel, poly-Lysine was added to the LabTek chambers for 2 h at room temperature (RT) to prepare the glass slides of the LabTek chambers for cell attachment. After 2 h cells were washed two times (5 min/wash) and added to the poly-Lys coated LabTek chambers for 1 h at RT (=cell attachment).

To visualize intracellular Alphabodies, cells were fixed with 4% formaldehyde at 4° C. for 10 min followed by permeabilization with 0.1% Triton X-100 at RT for 15 min. Cells were washed twice (10 min/wash) with glycine (0.75 g/100 ml) to stop the crosslinking of formaldehyde followed by a wash with DPBS (5 min/wash).

Cells were blocked with blocking buffer (DPBS+1% BSA) for 10 min at RT followed by incubation with the primary antibody directed against the V5 tag of the Alphabody (mouse anti-V5 Ab, Invitrogen, 46-0705) diluted at 1/400 in blocking buffer for 1 h at RT. Cells were washed 3 times (5 min/wash) with blocking buffer followed by addition of the secondary antibody, goat anti-mouse antibody labeled to Alexa488 (Invitrogen, A-10680) diluted 1/300 in blocking buffer and DAPI (4',6-Diamidino-2-Phenylindole, dihydrochloride) (nuclear staining) (1/100) for 30 min at RT. Finally, cells were washed 3 times (5 min/wash) with blocking buffer, 150 ul of DPBS was added and plates were read on a Zeiss Axiovert 200, LSM 510 Meta confocal microscope.

2.2 Results 2.2.1 Intracellular Uptake of AB1_hiKR1-V5 and AB1_A2aF_hiKR3-V5 in Human Glioblastoma Cells U87.MG Intracellular uptake of a concentration series of AB1_hiKR1-V5 (SEQ ID NO: 4) and AB1_A2aF_hiKR3-V5 (SEQ ID NO: 6) was studied in human glioblastoma cells. After 2 hours of incubation of Alphabody with cells, intracellular Alphabody was detected with an anti-V5 antibody and a secondary Alexa488 labeled antibody.

A dose response dependent uptake was observed for both cationized AB1 Alphabodies (FIG. 7).

The lower concentration limit of intracellular uptake of AB1_hiKR1-V5 (SEQ ID NO: 4) and AB1_A2aF_hiKR3-V5 (SEQ ID NO: 6) was determined qualitatively on images of single cells and corresponded to 39.1 nM and 19.5 nM, respectively. At these concentrations, a fluorescent signal higher than the control signal (cells without Alphabody) was still visible.

2.2.2 Intracellular Uptake of AB1_hiKR1-V5 and AB1_A2aF_hiKR3-V5 in Different Cell Lines Dose dependent uptake of AB1_hiKR1-V5 (SEQ ID NO: 4) and AB1_A2aF_hiKR3-V5 (SEQ ID NO: 6) (1250 nM, 312.5 nM, 156.3 nM, 78.1 nM, 39.1 nM, 19.5 nM and 9.8 nM) was studied in two non-cancer cell lines (HEK, CHO-K1) and in 6 additional cancer cell lines (U87.MG, BxPC-3, H1437, SW872, MT-4, Jurkat) (FIG. 7 and Table 4). The intracellular uptake of AB1_A2aF_hiKR3-V5 was compared to the intracellular uptake of MB23_hiR-V5 (SEQ ID NO: 2) at the same concentration in the same cells in a qualitative manner (visual comparison of the confocal microscopy images).

A dose dependent intracellular uptake was observed for all tested cell types. Very efficient uptake was observed in human glioblastoma (U87.MG) (FIG. 7) and liposarcoma cells (SW872) cells (data not shown).

The uptake efficacy of AB1_A2aF_hiKR3-V5 and MB23_hiR-V5 (SEQ ID NO: 2) varied between certain tested cell types. The lower concentration limit for intracellular uptake of AB1_A2aF_hiKR3-V5 was determined qualitatively by analysis of single cell images. The results are summarized in Table 4. It became clear that only low concentrations of Alphabody (9.8 nM) were needed to observe intracellular protein for SW872 and HEK cells. Higher concentrations of Alphabody were required to obtain a fluorescent signal above background for U87.MG, BxPC-3, H1437, MT4, CHO-K1 cells, and Jurkat T cell leukemia cells (Table 4).

TABLE 4

Lower concentration limit for intracellular uptake of cationized Alphabodies MB23_hiR-V5 and AB1_A2aF_hiKR3-V5 in 8 different cell lines

| Cell type | MB23_hiR-V5 Lower concentration limit for uptake | AB1_A2aF_hiKR3-V5 Lower concentration limit for uptake |
| --- | --- | --- |
| Glioblastoma cells (U87) | 4.9 nM | 19.5 nM |
| Pancreatic cancer (BxPC3) | 9.8 nM | 78.1 nM |
| Non small cell lung cancer (H1437) | 9.8 nM | 39.1 nM |
| Liposarcoma cells (SW872) | 19.5 nM | 9.8 nM |
| T cell leukemia (Jurkat) | 1250 nM | 1250 nM |
| T cell leukemia (MT4) | 156 nM | 78.1 nM |
| Chinese Hamster Ovary cells (CHO.K1) | 9.8 nM | 78.1 nM |
| HEK cells | 39.1 nM | 9.8 nM |

2.2.3 Effect of Heparin Washes on Intracellular Uptake of AB1_A2aF_hiKR3-V5

Intracellular uptake of AB1_A2aF_hiKR3-V5 (SEQ ID NO: 6) was studied in 3 different cancer cell lines using heparin washes to remove extracellularly bound Alphabody. Data were compared to the intracellular uptake results with PBS washes for the same cell lines.

Depending on the cell type, membrane staining disappeared partially or completely after washing with heparin, which indicates that the excess Alphabody present on the extracellular cell surface could be removed (data not shown).

2.2.4 Effect of Heparin Washes and Kinetics of Uptake of AB1_A2aF_hiKR3-V5

Kinetics of intracellular uptake of AB1_A2aF_hiKR3-V5 in human glioblastoma cells was performed using heparin washes. After 3.5 min, Alphabody was present inside the cell and fluorescent signal was maximal after 180 min (longest incubation time measured) (FIG. 8). The evolution of the intracellular uptake was most visible when analyzing the single cell images (data not shown). An increase in fluorescent signal was observed in function of incubation time. At short incubation times, Alphabody was mainly present near the intracellular membrane and moving away from the membrane when incubation times were prolonged.

2.3 Conclusions

Cationized MCL-1 Alphabodies (with charges in the A and C helix) penetrate in a dose dependent manner in different cell types including cancer and non-cancer cell lines.

Data obtained on uptake of MB23_hiR-V5 (SEQ ID NO: 2) and the 2 MCL-1 Alphabodies (AB1_hiKR1-V5 and AB1_A2aF_hiKR3-V5) in human glioblastoma cells indicated that the uptake efficiency of AB1_A2aF_hiKR3-V5 was greater than the uptake efficiency of MB23_hiR-V5, which in its turn was greater than the uptake efficiency of AB1_hiKR1-V5. These data indicate that uptake efficiency is not solely determined by the number of charges. Indeed, MB23_hiR-V5 has a net charge of 9 whereas AB1_hiKR1-V5 has a net charge of 11.

Intracellular uptake of AB1_A2aF_hiKR3-V5 appeared to be cell type dependent. Indeed, although the Alphabody was internalized by almost all tested cell types, the efficiency varied. As observed for MB23_hiR-V5, intracellular uptake was lower in human T cell leukemia cells. On the other hand, uptake in the cancer cell lines SW872 and U87.MG was highly efficient.

Similarly, the uptake efficacy of MB23_hiR-V5 appeared to be cell type dependent. These data confirm that uptake efficiency is not only related to net positive charges but also to the distribution of charges on the Alphabody Similar to the cellular uptake of MB23_hiR-V5, the uptake process of cationized MCL-1 Alphabodies is a fast process. After 3.5 min, Alphabody was present inside the cell. Analysis of single cells demonstrated an evolution in the fluorescent pattern suggesting the spreading or diffusion of the Alphabody away from the inner cell membrane into the intracellular space.

Example 3. Tumor Cell Viability Studies with CPAB Alphabodies Specifically Directed Against MCL-1

This Example describes the effect of MCL-1 Alphabodies on viability of cancer and non-cancer cell lines. In general, inhibition of interactions between MCL-1 and BAK results in the liberation of BAK and the formation of Mitochondrial Outer Membrane Pores (MOMP) via BAK/BAX homo- and/or heterodimerization and finally apoptosis of the cell. A panel of cancer cell lines was treated with Alphabodies directed against MCL-1 and control Alphabodies lacking a binding site to MCL-1 and cell viability was monitored using MTT (3-(4,5-Dimethylthiazol-2-YI)-2,5-Diphenyltetrazolium Bromide).

3.1 Methods Used

For the impact of Alphabodies on cancer cell viability, we focused on two MCL1 binding Alphabodies, i.e. AB1_hiKR1-V5 (SEQ ID NO: 4) and AB1_A2aF_hiKR3-V5 (SEQ ID NO: 6). These Alphabodies contained the MCL-1 binding site in the B helix and displayed different cationization patterns as shown in FIG. 6. Lys and Arg residues were used to decorate the Alphabodies, resulting in net charges of +11 and +19 for AB1_hiKR1-V5 and AB1_A2aF_hiKR3-V5, respectively.

Cell viability in function of concentration was studied in 7 different cell lines, including 6 cancer cell lines (MT4, Jurkat, SW872, H1437, BxPC3, U87.MG). The induction of cell death by Alphabodies was also studied on primary cells (PBMC).

3.1.1 Expression and Purification of AB1_hiKR1-V5 and AB1_A2aF_hiKR3-V5

Cationized Alphabodies AB1_hiKR1-V5 (SEQ ID NO: 4) and AB1_A2aF_hiKR3-V5 (SEQ ID NO: 6) were expressed and purified as described in Example 2.

3.1.2 Cell Viability Assays

Cell viability was studied in 6 different cancer cell lines (U87.MG, BxPC-3, H1437, SW872, MT-4 and Jurkat) (Table 5). Effects of Alphabodies on viability were also studied in primary cells (PBMC) obtained from a healthy donor.

Adherent cell lines (U87.MG, BxPC-3, H1437, SW872) were cultured in DMEM or RPMI+10% Foetal Bovine Serum (FBS), seeded in 96 well plates and incubated overnight at 37° C. and 5% $CO_2$. The next day cationized Alphabody (dilution series) was incubated with the seeded cells for 2 h in Opti-MEM cell culture medium without Foetal Bovine Serum (FBS). Suspension cell lines (MT4 and Jurkat) were seeded in 96-well plates in Opti-MEM cell culture medium without FBS and containing serial dilutions of Alphabody and incubated for 2 h at 37° C. and 5% $CO_2$. PBMC were isolated from a healthy donor and cultured in RPMI containing 10% FBS and IL-2.

After 2 h, Opti-MEM with FBS was added to obtain a final concentration of 10% FBS and cells were incubated for 48 h at 37° C. and 5% $CO_2$. Cell viability was monitored using MTT. MTT is reduced to formazan by living cells. Solubilization of the formazan crystals results in a colored product that can be measured by spectrophotometry at 540 nm. Cell viability was expressed as percentage of viability of non-treated cells (=100% viability). All experiments were performed in triplicate. Data are presented as mean values with standard deviations.

TABLE 5

Cell lines used for cell viability studies

| Cell line | Description |
| --- | --- |
| U87.MG | Human glioblastoma cells |
| BxPC-3 | Human pancreatic cancer cells |
| H1437 | Human non-small cell lung cancer cells |
| SW872 | Human liposarcoma cells |
| MT-4 | Human T cell leukemia cells |
| Jurkat | Human T cell leukemia cells |

3.2 Results 3.2.1 Effects on Cell Viability of Hematological Cancer Cell Lines by MCL-1 Alphabodies Effects on cell viability of cationized MCL-1 Alphabodies AB1_hiKR1-V5 (SEQ ID NO: 4) and AB1_A2aF_hiKR3-V5 (SEQ ID NO: 6) was studied in human T cell leukemia cell lines MT4 and Jurkat.

Cationized Alphabody AB1_A2aF_hiKR3-V5 induced dose dependent cell death of MT4 cells with nearly complete abolishment of cell viability at 10 microM Alphabody. The AB1_hiKR1-V5 Alphabody was less potent. Control Alphabodies KLPVM-scAB013-V5 and MB23_hiR-V5 had no effect on cell viability, i.e. 100% of cells were viable even at the highest concentrations (FIG. 9). On Jurkat cells, both MCL-1 Alphabodies were somewhat less potent. Treatment with the highest concentration of Alphabody resulted in 60% and 40% of cell death for AB1_A2aF_hiKR3-V5 and AB1_hiKR1-V5, respectively (FIG. 10). Viability data were in agreement with the intracellular uptake efficacy of AB1_A2aF_hiKR3-V5 for MT4 and Jurkat cells. This Alphabody showed a more pronounced intracellular uptake in MT4 cells compared to Jurkat cells (data not shown).

3.2.2 Effects on Cell Viability of Different Cancer Cell Lines by MCL-1 Alphabodies (i) Human Liposarcoma Cells (SW872)

Alphabodies AB1_A2aF_hiKR3-V5 (SEQ ID NO: 4) and AB1_hiKR1-V5 (SEQ ID NO: 6) induced dose dependent cell death in human liposarcoma cells albeit at low percentages (data not shown). At the highest concentrations of Alphabody tested, 40% and 30% cell death was measured for AB1_A2aF_hiKR3-V5 (SEQ ID NO: 6) and AB1_hiKR1 (SEQ ID NO: 4), respectively. Control Alphabody MB23_hiR-V5 induced 10% cell death at 10 microM. Both AB1_A2aF_hiKR3-V5 and the control Alphabody MB23_hiR-V5 were taken up by the SW872 cells (data not shown and FIG. 4).

(ii) Human Non-Small Cell Lung Cancer Cells (H1437)

Alphabody AB1_A2aF_hiKR3-V5 induced dose dependent cell death in non-small cell lung cancer cells (H1437) (data not shown). The highest concentration of Alphabody tested (10 microM) induced 50% cell death. Control Alphabody (MB23_hiR-V5) and AB1_hiKR1-V5 induced 15% cell death at 10 microM. AB1_A2aF_hiKR3-V5 was taken up less efficiently in H1437 cells compared to the control MB23_hiR-V5 (FIG. 4).

(iii) Human Pancreatic Cancer Cells (BxPC-3)

Alphabody AB1_A2aF_hiKR3-V5 induced dose dependent cell death in human pancreatic cancer cells (BxPC-3) (data not shown). The highest concentration of Alphabody tested (10 microM) induced 60% cell death. 10 microM control Alphabody (KLPVM-scAB013-V5) and AB1_hiKR1-V5 induced 30% and 35% cell death, respectively. Alphabody A2aF_hiKR3-V5 was taken up in BxPC-3 cells (data not shown).

(iv) Human Glioblastoma Cells (U87.MG)

Alphabodies AB1_A2aF_hiKR3-V5 (SEQ ID NO: 6) and AB1_hiKR1-V5 (SEQ ID NO: 4) induced dose dependent cell death human glioblastoma cells (U87.MG) (data not shown). The highest concentration of both Alphabodies tested (10 microM) induced 35% cell death. Control Alphabody KLPVM-scAB013-V5 had little effect on cell viability. Alphabody A2aF_hiKR3-V5 was taken up efficiently in U87.MG cells (FIG. 7).

3.2.3 Effects on Cell Viability of Non-Cancer Cell Lines by MCL-1 Alphabodies (i) PBMC Alphabody AB1_A2aF_hiKR3-V5 induced 35% cell death of PBMC at 10 microM (FIG. 11). Other tested Alphabodies induced no cell death in PBMC.

3.3 Conclusions

The induction of cell death by MCL-1 binding Alphabodies appeared to be cell type dependent and the effect was most pronounced on the hematological cancer cell line MT4. For that cell line, 10 microM AB1_A2aF_hiKR3-V5 induced complete cell death after 48 h. The Alphabody AB1_A2aF_hiKR3-V5 (SEQ ID NO: 6) had greater effects on cell viability compared to the other MCL-1 Alphabody, AB1_hiKR1-V5 (SEQ ID NO: 4).

Although MT4 and Jurkat cells are both T cell leukemia cells, the behavior of MCL-1 Alphabodies on these cells differed: Alphabodies were more potent on MT4 cells compared to Jurkat cells. These data suggest a different survival mechanism for these cancer cell lines.

When comparing the susceptibility of the different cell lines to the cell death inducing effects of AB1_A2aF_hiKR3-V5 the following order of sensitivity of MCL-1 Alphabodies can be established: MT4>Jurkat=BxPC-3>H1437=SW872>U87.MG, with MT4 cells being the most susceptible.

Uptake efficacy is not correlated to cell death induction. The control Alphabody MB23_hiR-V5 (SEQ ID NO: 2), which was taken up very efficiently in different cell lines, did not induce cell death, suggesting that internalized Alphabody is not toxic to the cells. On the other hand, AB1_A2aF_hiKR3-V5 was taken up efficiently in U87.MG cells, while this did not result in the best cell killing activity.

Example 4. CPAB Alphabody AB1_Pan_hiKR3-V5 Specifically Directed Against Different Members of the BCL-2 Family of Proteins This example describes the design and binding properties of Alphabody AB1_pan_hiKR3-V5 (SEQ ID NO: 10), the protein sequence of which is specified in FIG. 12. This Alphabody was designed for intracellular uptake by cationization (i.e. by decoration with Arg/Lys amino acid residues) and to specifically bind to three different intracellular target proteins, namely MCL-1, BCL-XL and BCL-2a.

4.1 Methods Used
4.1.1 Production and Purification of Recombinant Intracellular Target Proteins
Recombinant human BCL-2 family proteins were produced in E. coli as Glutathione S Transferase (GST) fusion proteins with the GST tag at the N-terminus of the proteins. For all proteins the C-terminal Tm (transmembrane) region was removed. The following recombinant proteins were produced: BCL-XL with a C terminal deletion of 24 amino acids, isoform alpha of BCL-2 (BCL-2a) with a C-terminal deletion of 32 amino acids. To produce MCL-1 the N-terminal PEST region (region containing signal for rapid degradation of proteins) and the C-terminal Tm region were deleted and recombinant MCL-1 corresponded to residues 172 to 327 of human MCL-1. All proteins were purified using the GST-tag.
4.1.2 ELISA Assays
Maxisorp Nunc plates were coated with 100 microl anti-V5 antibody (5 microg/ml) in carbonate buffer pH 9.6 overnight at 4° C. The next day, plates were washed 3 times with Tris Buffered Saline containing 0.05% Tween 20 (TBST) and blocked with TBS containing 0.1% BSA and 0.5% gelatin for 2 h at 37° C. After washing plates 5 times with TBST, 500 nM AB1_pan_hiKR3-V5 Alphabody was added to the plates for 2 h at RT while shaking. Plates were washed 10 times with TBST and five-fold dilutions of Glutathione S transferase (GST) tagged recombinant BCL-2 family proteins (MCL-1, BCL-XL and BCL-2a) were added and further incubated for 2 h at RT while shaking. Binding of GST-tagged recombinant BCL-2 family proteins was detected using an anti-GST antibody conjugated to Horse Radish Peroxidase. Signals were developed by reacting with ortho-phenylenediamine and the reaction was stopped with 4M $H_2SO_4$ when OD reached a value between 2 and 3. Signals indicative for specific binding of AB1_pan_hiKR3-V5 to the particular BCL-2 family recombinant protein were read at 492 nm and 630 nm.

4.2 Results
It is clear from FIGS. 13 and 14 that Alphabody AB1_pan_hiKR3-V5 is able to specifically bind to different types of BCL-2 family members in a dose-dependent fashion. Indeed, AB1_pan_hiKR3-V5 specifically binds to MCL-1 with a binding affinity of approximately 1.9 nM (FIGS. 13 and 14A). As also shown in FIG. 14A, Alphabody AB1_A2aF_hiKR3-V5, which was described in the previous examples, is also directed against MCL-1 and specifically binds to this intracellular protein with a binding affinity of 1.0 nM. Control Alphabody MB23-hiR-V5, directed against IL-23, which is not an intracellular protein, does not show binding to MCL-1.

As further exemplified in FIGS. 13 and 14, AB1_pan_hiKR3-V5 specifically binds in a dose-dependent way to two other intracellular proteins, namely BCL-XL and BCL-2a, with a binding affinity of approximately 4.5 and 18.7 nM, respectively (FIGS. 14B and 14C). On the contrary, both Alphabody AB1_A2aF_hiKR3-V5, which was described in the previous examples and specifically designed against MCL-1, as well as control Alphabody MB23-hiR-V5, directed against IL-23, do not show specific binding to either one of BCL-XL or BCL-2a (FIGS. 14B and 14C). These results demonstrate the specific binding in a dose-dependent manner of Alphabody AB1_pan_hiKR3-V5 to three different intracellular proteins with high affinity.

Example 5. Intracellular Uptake of CPAB Alphabody AB1_Pan_hiKR3-V5

5.1 Methods Used
Intracellular uptake of Alphabody AB1_pan_hiKR3-V5 (SEQ ID NO: 10) was studied in human glioblastoma cells (U87.MG) in function of Alphabody concentration. The uptake was studied by confocal microscopy and intracellular Alphabody was visualized using an anti-V5 antibody recognizing the C-terminal V5 tag of the Alphabody. All experiments were performed on fixed and permeabilized cells. Control experiments with non-permeabilized cells were included.

This Alphabody binds to three different intracellular proteins of the BCL-2 family through a binding site present on its B helix and displays different cationization patterns as shown in FIG. 12. Indeed, Lys and Arg residues were used to decorate the Alphabody and to design positively charged internalization regions.
5.1.1 Expression and Purification of Cationized Alphabody AB1_pan_hiKR3-V5
Cationized Alphabody AB1_pan_hiKR3-V5 (SEQ ID NO: 10) was expressed in the soluble fraction of E. coli bacteria. Proteins were purified by Ni-NTA chromatography followed by desalting and buffer exchange procedures. Proteins were solubilized in 20 mM citric acid pH 3.0.
5.1.2 Intracellular Uptake of Cationized Alphabody AB1_pan_hiKR3-V5
Intracellular uptake of AB1_pan_hiKR3-V5 (SEQ ID NO: 10) was studied in human glioblastoma cells (U87.MG), which were cultured in DMEM+10% Foetal Bovine Serum (FBS) and seeded in LabTek chambers at 10.000 cells/chamber and incubated overnight at 37° C. and 5% $CO_2$. The next day, cationized Alphabody (dilution series) was incubated with the seeded cells for 2 h at 37° C. and 5% $CO_2$. After incubation with the Alphabody, cells were washed 4 times (5 min/wash) with PBS (containing Mg and Ca (DPBS)).

To visualize intracellular Alphabody, cells were fixed with 4% formaldehyde at 4° C. for 10 min followed by permeabilization with 0.1% Triton X-100 at RT for 15 min. Cells were washed twice (10 min/wash) with glycine (0.75 g/100 ml) to stop the crosslinking of formaldehyde followed by a wash with DPBS (5 min/wash).

Cells were blocked with blocking buffer (DPBS+1% BSA) for 10 min at RT followed by incubation with the primary antibody directed against the V5 tag of the Alphabody (mouse anti-V5 Ab, Invitrogen, 46-0705) diluted at 1/400 in blocking buffer for 1 h at RT. Cells were washed 3 times (5 min/wash) with blocking buffer followed by addition of the secondary antibody, goat anti-mouse antibody labeled to Alexa488 (Invitrogen, A-10680) diluted 1/300 in blocking buffer and DAPI (4',6-Diamidino-2-Phenylindole, dihydrochloride) (nuclear staining) (1/100) for 30 min at RT. Finally, cells were washed 3 times (5 min/wash) with blocking buffer, 150 microl of DPBS was added and plates were read on a Zeiss Axiovert 200, LSM 510 Meta confocal microscope.

5.2 Results 5.2.1 Intracellular Uptake of AB1_pan_hiKR3-V5 in Human Glioma Cells U87.MG Intracellular uptake of a concentration series of AB1_pan_hiKR3-V5 (SEQ ID NO: 10) was studied in human glioblastoma cells. After 2 hours of incubation of Alphabody with cells, intracellular Alphabody was detected with an anti-V5 antibody and a secondary Alexa488 labeled antibody.

A dose response dependent uptake was observed (data not shown). The lower concentration limit of intracellular uptake of AB1_pan_hiKR3-V5 was determined qualitatively on images of single cells and corresponded to 156 nM, respectively. At these concentrations, a fluorescent signal higher than the control signal (cells without Alphabody) was still visible.

5.3 Conclusion

Cationized Alphabody AB1_pan_hiKR3-V5 (SEQ ID NO: 10) (with positive charges in the A and C helix) binds specifically and with high affinity to three different intracellular proteins and is able to penetrate cells in a dose dependent manner.

Example 6. Demonstration of Cytoplasmic Presence of a CPAB Alphabody

To demonstrate that the CPAB polypeptides envisaged herein are able to access the cytosolic compartment of cells, a cell lysis protocol was elaborated which allows selective plasma membrane permeabilization without affecting vesicles from the endosomal or lysosomal compartments. This protocol to obtain a cellular cytosolic fraction is based on the use of a lysis buffer that contains digitonin (well established for its use in cell fractionation. For each cell type, the digitonin concentration and incubation time can be optimized to allow selective permeabilization without affecting the endosomal compartment. Proper cell fractionation can be confirmed by checking for the presence of cytosolic and endosomal markers in the resulting cellular fractions. In this protocol for cellular fractionation of Jurkat cells, we use a very conservative digitonin-treatment protocol (low digitonin concentration, short digitonin incubation time) in order to make sure that the endosomes remain intact. By doing so, a cytosolic fraction (CF) is obtained that contains the digitonin-released cytosolic content, while sacrificing a part of the cytosolic content to the digitonin-resistant rest fraction (RF).

The digitonin cell lysis protocol was applied as follows. Jurkat cells were seeded in a 24 well plate in Optimem (Life Technologies) containing 10% foetal bovine serum (FBS) overnight at 37° C. and 5% CO2. A CPAB polypeptide (MB23 hiR_no tag; MGHHHHHHHHHHSSGHIEGRHM-SIEQIQKEITTIQEVIAAIQKYIYTMTGGSGGSGGM-SIQQIQAAI RRIQRAIRRIQRAIRRMTGSGGGSGM-SIEEIQKQIAAIQEQIVAIYKQIMAMAS, SEQ ID NO: 33) was added to the cells at a final concentration of 1 uM in Optimem+10% FBS. After a 2 h incubation at 37° C., the cells were washed 2 times with ice-cold Optimem followed by centrifugation. All centrifugation steps in this protocol were performed for 10 min at 1000 g at 4° C. unless stated otherwise. To remove extracellularly bound Alphabody, cell pellets were incubated with trypsine for 15 min at 37° C. and after trypsin inactivation by FBS addition, cell pellets were washed 2 times for 5 min at room temperature with heparin (100 ug/ml heparin (Sigma-Aldrich) in ice-cold PBS+0.1% BSA+5 mM glucose). After an additional wash step with Optimem, cell lysis was performed by resolubilizing the cell pellet in 30 µl digitonin cell lysis buffer (15 ug/ml digitonin (Sigma-Aldrich) in 1% BSA+0.3 M sucrose+0.1 M KCl+2.5 mM MgCl2+1 mM EDTA+10 mM HEPES, pH7.4) followed by a 10 minute shaking incubation on ice. The digitonin lysis buffer allows a mild and selective permeabilization of the plasma membrane while maintaining integrity of the endosomes and other membrane compartments within the cell. The supernatant obtained after centrifugation of the digitonin-treated cells (10 min 16000 g at 4° C.) corresponds to the cytosolic contents that are released upon digitonin treatment (cytosolic fraction, CF). The remaining pellet is washed 2 times with PBS and after resuspension of the pellet in a 1% Triton-X100 containing cell lysis buffer (Cell Lysis Buffer, Cell Signaling Technology) the digitonin-resistant rest fraction (RF) is obtained.

The digitonin cell lysis protocol was applied to Jurkat cells after a 2 h incubation with 1 µM CPAB MB23_hiR_no tag and washing away possible extracellularly bound Alphabody by trypsine/heparin washes. Resulting cellular cytosolic and rest fractions (CF and RF) were blotted with anti-His antibody, together with calibration samples containing known amounts of Alphabody.

FIG. 15 shows the result of this experiment. A band corresponding to the correct molecular weight of MB23_hiR_no tag is visible in the Jurkat CF and RF. This clearly demonstrates the presence of MB23_hiR_no tag in the cytosolic compartment of Jurkat cells.

Based on the calibration samples that were run on the same gels, intracellular CPAB concentrations can be roughly estimated. Based on an estimated cytosolic volume of 1 pl for a Jurkat cell, the estimated intracellular CPAB concentrations range from 0.1 to 3 uM after an incubation time of 2 hours.

To demonstrate that the performed cellular fractionation method resulted in a partial release of cytosolic contents in the CF while membranous organelles and structures were found in the RF, the CF and RF were tested for the presence of cytosolic (GAPDH and LDH), endosomal (NAG, Lamp-1, Flotillin-1) and membrane (Flotillin-1) markers. FIGS. 16 and 17 demonstrate that NAG, Flotillin-1 and Lamp-1 are exclusively present within the RF fractions. LDH and GAPDH are found in both CF and RF fractions, indicating that the CF contains the partial cytosolic content, with some cytosolic content going into the RF.

GENERAL CONCLUSION

As will be clear from the results obtained in Examples 1 to 6, the CPAB polypeptides and CPAB Alphabodies are taken up rapidly by a variety of tumor cell lines at low nM range concentrations. This uptake is dose dependent, and to a large extent energy independent (i.e. by direct transduction). The polypeptides with anti-MCL1 activity as disclosed herein effectively penetrate cancer cells, bind to the intracellular target molecule MCL-1, and provoke a significant biological effect, namely induction of apoptosis. In addition, the AB1_pan_hiKR3-V5 Alphabody was shown to bind with high affinity to a broader panel of BCL-2 family proteins and was also efficiently taken up in human glioblastoma (U87.MG) cells. These results indicate that the polypeptides of the present invention exhibit clear competitive advantages over other known approaches to address intracellular targets.

The invention claimed is:

1. A polypeptide comprising at least one Alphabody structure sequence having the general formula HRS1-L1-HRS2-L2-HRS3, wherein each of HRS1, HRS2 and HRS3 is independently a heptad repeat sequence (HRS) comprising 2 to 7 consecutive heptad repeat units, at least 50% of all heptad a- and d-positions are occupied by isoleucine residues, each HRS ends with a partial heptad abc or defga such that each HRS starts and ends with an aliphatic or aromatic amino acid residue located at either a heptad a- or d-position, and HRS1, HRS2 and HRS3 together form a triple-stranded, alpha-helical, coiled coil structure; and each of L1 and L2 is independently a linker fragment, which covalently connects HRS1 to HRS2 and HRS2 to HRS3, respectively, wherein said structure sequence comprises at least one positively charged internalization region ensuring internalization of said polypeptide into a cell, wherein said internalization region extends between two positively charged amino acid residues, consists of a fragment of not more than 16 amino acid residues and is characterized by the presence of at least six positively charged amino acid residues of which at least 50% are comprised within said structure sequence and wherein said internalization region comprises at least 4 arginine residues or at least 5 lysine residues.

2. The polypeptide according to claim 1, wherein at least one positively charged internalization region is fully comprised within said structure sequence.

3. The polypeptide according to claim 1, wherein at least one positively charged internalization region is fully comprised within one alpha-helix of said at least one structure sequence.

4. The polypeptide according to claim 1, wherein said positively charged internalization region comprises between 6 and 12 Arginine residues.

5. The polypeptide according to claim 1, wherein said positively charged internalization region comprises a motif selected from the group consisting of: ZZXXZXXZZXXX, ZXXZXXZZXXZXXZ, ZXXZZXXZXXZ, ZXXZXXZXXXZXXZZ, ZXXXZXXZXXZZXXZ, ZXXZZXXZXXZZ, ZXXZZXXZZXXZ, ZZXXXXXZZXXXXXZZ, wherein Z represents a positively charged amino acid and X represents any amino acid residue.

6. The polypeptide according to claim 5, wherein in said motif, between 75 and 100% of said Z are Arginine.

7. The polypeptide according to claim 1, wherein said positively charged internalization region comprises a motif according to any one of SEQ ID NOs: 13 to 32.

8. The polypeptide according to claim 1, wherein at least one structure sequence further comprises at least one binding site to an intracellular target molecule.

9. A pharmaceutical composition comprising the polypeptide according to claim 1, and one or more pharmaceutically acceptable carriers.

10. A method for producing a polypeptide comprising at least one triple-stranded, alpha-helical, coiled coil amino acid structure sequence having the general formula HRS1-L1-HRS2-L2-HRS3, wherein the method at least comprises the step of synthesizing and/or constructing the polypeptide, wherein each of HRS1, HRS2 and HRS3 is independently a heptad repeat sequence (HRS) comprising 2 to 7 consecutive heptad repeat units, at least 50% of all heptad a- and d-positions are occupied by isoleucine residues, each HRS ends with a partial heptad abc or defga such that each HRS starts and ends with an aliphatic or aromatic amino acid residue located at either a heptad a- or d-position, and HRS1, HRS2 and HRS3 together form a triple-stranded, alpha-helical, coiled coil structure; and each of L1 and L2 is independently a linker fragment, which covalently connects HRS 1 to HRS2 and HRS2 to HRS3, respectively;

wherein said method comprises providing in said structure sequence at least one positively charged internalization region, wherein said internalization region extends between two positively charged amino acid residues, consists of a fragment of not more than 16 amino acid residues and is characterized by the presence of at least six positively charged amino acid residues of which at least 50% are comprised within said structure sequence and wherein said internalization region comprises at least 4 arginine residues or at least 5 lysine residues so as to obtain an internalization region comprised at least in part within said structure sequence having the general formula HRS1-L1-HRS2-L2-HRS3.

11. The method according to claim 10, wherein the method further comprises selecting at least one structure sequence for its specific binding affinity to an intracellular target molecule of interest.

* * * * *